United States Patent
Mukherjee et al.

(10) Patent No.: US 10,912,799 B2
(45) Date of Patent: *Feb. 9, 2021

(54) COMPOSITIONS AND METHODS FOR INHIBITION OF LINEAGE SPECIFIC ANTIGENS

(71) Applicant: The Trustees of Columbia University in the City of New York, New York, NY (US)

(72) Inventors: Siddhartha Mukherjee, New York, NY (US); Florence Borot, New York, NY (US); Abdullah Mahmood Ali, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/877,932

(22) Filed: May 19, 2020

(65) Prior Publication Data

US 2020/0276244 A1 Sep. 3, 2020

Related U.S. Application Data

(63) Continuation of application No. 16/174,089, filed on Oct. 29, 2018, now Pat. No. 10,660,919, which is a continuation of application No. 15/655,432, filed on Jul. 20, 2017, now Pat. No. 10,137,155, which is a continuation of application No. PCT/US2016/057339, filed on Oct. 17, 2016.

(60) Provisional application No. 62/242,685, filed on Oct. 16, 2015.

(51) Int. Cl.
| | |
|---|---|
| *A61K 35/28* | (2015.01) |
| *C07K 16/30* | (2006.01) |
| *C12N 5/0789* | (2010.01) |
| *A61P 35/00* | (2006.01) |
| *A61P 43/00* | (2006.01) |
| *A61P 35/02* | (2006.01) |
| *A61K 35/17* | (2015.01) |
| *C07K 14/725* | (2006.01) |
| *C07K 14/705* | (2006.01) |
| *C07K 16/28* | (2006.01) |
| *A61K 39/00* | (2006.01) |
| *A61K 35/12* | (2015.01) |

(52) U.S. Cl.
CPC ........... *A61K 35/28* (2013.01); *A61K 35/17* (2013.01); *A61P 35/00* (2018.01); *A61P 35/02* (2018.01); *A61P 43/00* (2018.01); *C07K 14/7051* (2013.01); *C07K 14/70517* (2013.01); *C07K 14/70521* (2013.01); *C07K 16/2803* (2013.01); *C07K 16/30* (2013.01); *C07K 16/3061* (2013.01); *C12N 5/0647* (2013.01); *A61K 2035/124* (2013.01); *A61K 2039/505* (2013.01); *C07K 2317/24* (2013.01); *C07K 2317/622* (2013.01); *C07K 2319/02* (2013.01); *C07K 2319/03* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | |
|---|---|---|
| 10,137,155 B2 | 11/2018 | Mukherjee et al. |
| 2010/0172882 A1 | 1/2010 | Glazer et al. |
| 2014/0286973 A1 | 9/2014 | Powell, Jr. |
| 2014/0322212 A1 | 10/2014 | Brogdon et al. |
| 2015/0283178 A1 | 10/2015 | June et al. |
| 2015/0283255 A1 | 10/2015 | McDonagh et al. |
| 2016/0096892 A1 | 4/2016 | Brogdon |
| 2016/0144026 A1 | 5/2016 | Lutteropp et al. |
| 2017/0044500 A1 | 2/2017 | Cooper |
| 2017/0145094 A1 | 5/2017 | Galetto |
| 2018/0282762 A1 | 10/2018 | Gori |
| 2019/0046580 A1 | 2/2019 | Mukherjee et al. |
| 2019/0314418 A1 | 10/2019 | Mukerjee |
| 2019/0321410 A1 | 10/2019 | Mukerjee |

FOREIGN PATENT DOCUMENTS

| | | |
|---|---|---|
| EP | 3025719 | 6/2016 |
| EP | 16166854.6 | 11/2017 |
| EP | 16166856.1 | 11/2017 |
| EP | 16166857.9 | 11/2017 |
| EP | 16196856.5 | 11/2017 |
| EP | 16196858.1 | 11/2017 |
| EP | 16196856.7 | 11/2017 |
| EP | 17197820.8 | 5/2018 |
| WO | 2009/052431 | 4/2009 |
| WO | 2011048350 | 4/2011 |
| WO | 2012012667 | 1/2012 |

(Continued)

OTHER PUBLICATIONS

Gill et al., Preclinical targeting of human acute myeloid leukemia and myeloablation using chimeric antigen receptor-modified T cells, Blood, 123(15): 2343-2354, Apr. 10, 2014.

(Continued)

*Primary Examiner* — Michail A Belyavskyi
(74) *Attorney, Agent, or Firm* — Leason Ellis LLP

(57) ABSTRACT

Disclosed herein are methods of administering an agent targeting a lineage-specific cell-surface antigen and a population of hematopoietic cells that are deficient in the lineage-specific cell-surface antigen for immunotherapy of hematological malignancies.

20 Claims, 20 Drawing Sheets

Specification includes a Sequence Listing.

(56) References Cited

FOREIGN PATENT DOCUMENTS

| WO | 2014059173 | 4/2014 |
|----|------------|--------|
| WO | 2014130635 | 5/2014 |
| WO | 2014144622 | 9/2014 |
| WO | 2014191128 | 12/2014 |
| WO | 2015090229 | 6/2015 |
| WO | 2015/150526 | 10/2015 |
| WO | 2015/164740 | 10/2015 |
| WO | 2016/014576 | 1/2016 |
| WO | 2016/182959 | 11/2016 |
| WO | 2016176651 | 11/2016 |
| WO | 2017/066760 | 4/2017 |
| WO | 2017079400 | 5/2017 |
| WO | 2017/172981 | 10/2017 |
| WO | 2017186718 | 11/2017 |
| WO | 2018083071 | 5/2018 |
| WO | 2018/160768 | 9/2018 |
| WO | 2019046285 | 3/2019 |

OTHER PUBLICATIONS

Henig & Zuckerman, Hematopoietic Stem Cell Transplantation—50 Years of Evolution and Future perspectives; Rambam Maimonides Med J. 5(4):e0028, Oct. 2014.
Schendel and Frankenberger, Limitations for TCR gene therapy by MHC-restricted fracticide and TCR-mediated hematopoietic stem cell technology, OncoImmunology 2:1, 322410, Jan. 2013.
Kebriaei et al., Infusing CD-19-directed T cells to augment disease control in patients undergoing autologous hematopoietic stem-cell transplantation for advanced B-lymphoid malignancies, Human Gene Therapy 23:444-450, May 2012.
Kuijpers et al., CD20 deficiency in humans results in impaired T cell-independent antibody responses, J Clin Invest. 120(1):214-222.
Kolb, Graft-versus-leukemia effects of transplantation and donor lymphocytes; Blood. 112(12): 4371-4383, 2008.
Falkenburg et al., T cell therapy in allogeneic stem cell transplantation, Biol Blood Marrow Transplant. 14(1 Suppl 1):136-141, Jan. 2008.
Shono et al., Bone marrow graft-versus-host disease : early destruction of hematopoietic niche after MHC-mismatched hematopoietic stem cell transplantation, Blood. 115(26):5401-11, 2010.
Ukena et al., Human regulatory T cells in allogeneic stem cell transplantation, Blood. 118(13):e82-92, 2011.
Belicha-Villanueva et al., What is the role of alternate splicing in antigen presentation by major histocompatibility complex class I molecules, Immunol Res. 46(1-3):32-44, 2010.
Zernich et al., Natural HLA Class I Polymorphism Controls the Pathway of Antigen Presentation and Susceptibility to Viral Evasion, J Exp Med. 200(1):13-24, 2004.
Anurathapan et al., Engineered T cells for cancer treatment; Cytotherapy ; 16(6) : 713-733, Jun. 2014.
Bubien et al., Transfection of the CD20 cell surface molecule into ectopic cell types generates a Ca2+ conductance found constitutively in B lymphocytes, J Cell Biol, vol. 121, No. 5, 1121-1132, Jun. 1993.
Roberts et al., CD45-deficient severe combined immunodeficiency caused by uniparental disomy; PNAS, vol. 109, No. 26, Jun. 26, 2012.
U.S. Appl. No. 62/250,561, filed Nov. 4, 2015.
Laurent Poirot et al. Multiplex Genome-Edited T-cell Manufacturing Platform for "Off-the-Shelf" Adoptive T-cell Immunotherapies, Cancer Research, vol. 75, No. 18, 2015, pp. 3853-3864.
Saydaminova K et al., Efficient genome editing in hematopoietic stem cells with helper-dependent Ad5/35 vectors expressing site-specific endonucleases under microRNA regulation, Molecular Therapy—Methods & Clinical Develop, Nature Publishing Group, GB, vol. 2, No. Suppl. C, 2015, pp. 1-11.
European Search Report dated Mar. 26, 2019 corresponding to European Patent Application No. EP16856410.2, 9 pages.
Larson et al. "Tracking the global spread of vaccine sentiments: The global response to Japan's suspension of its HPV vaccine recommendation" (Human Vaccines & Immunotherapy, 2014, 10:982-985).
Mandal et al., Efficient ablation of genes in human hematopoietic stem and effector cells using CRISPR/Cas9, Cell Stem Cell 15, 643-652, Nov. 6, 2014.
Kim et al "Genetic Inactivation of CD33 in Hematopoietic Stem Cells to Enable CAR T Cell Immunotherapy for Acute Myeloid Leukemia" 2018, Cell 173, 1439-1453.
Humbert et al., "Engineering resistance to CD33-targeted immunotherapy in normal hematopoiesis by CRISPR/Cas9-deletion of CD33 exon 2" 2018, Leukemia, https://doi.org/10.1038/s41375-018-0277-8.
Borot et al., "Gene-edited stem cells enable CD33-directed immune therapy for myeloid malignancies" 2019, PNAS 116:24 11978-11987.
Ehniger et al. "Distribution and levels of cell surface expression of CD33 and CD123 in acute myeloid leukemia" (Blood Cancer Journal, 2014, 4:e218.
Sulem et al "Identification of a large set of rare compete human knockouts" (Nature Genetics, 2015, 47:448-453).
Angata et al. "Large-scale sequencing of the CD33-related Siglec gene cluster in five mammalian species reveals rapid evolution by multiple mechanisms" (PNAS, 2004, 101:13251-13256).
Vitale et al. (PNAS, 1999, 96:15091-15096).
AABB (http://www.aabb.org/aabbcct/therapyfacts/Pages/hsc.aspx?PF=1; 2020, Hematopoietic Stem Cell).
Kim et al. Blood, 2016, 128:1000.
De Oliveira et al., Human Gene Therapy, 2013, 24:824-839.
ATCC (ATCC CCL-86, 2017).
Walter RB, et al., Acute myeloid leukemia stem cells and CD33-targeted immunotherapy. Blood. 2012, 119 (26):6198-6208.
Kenderian SS et al. CD33 Specific Chimeric Antigen Receptor T Cells Exhibit Potent Preclinical Activity against Humar II.cute Myeloid Leukemia. Leukemia. 2015, 29(8):1637-47.
Ritchie OS, et al. Persistence and efficacy of second generation CART cell against the LeY antigen in acute myeloid eukemia. Mol. Ther. 2013, 21(11):2122-9.
Burnett A, et al., Therapeutic advances in acute myeloid leukemia, J Clin Oncol, 2011, vol. 29/Issue 5; pp. 487-494.
Buckley SA, et al., Update on Antigen-Specific Immunotherapy of Acute Myeloid Leukemia. Curr. Hemalol. Malig. Rep., 2015; 10(2): 65-75.
Zhao, Y et al. Extrathymic Generation of Tumor-Specific T Cell from Genetically Engineered Human Hematopoietic Stem Cells via Notch Signaling. Cancer Research. 2007, vol. 67, No. 6; pp. 2425-2429.
International Search Report and Written Opinion dated Jan. 24, 2017, corresponding to International PCT Application No. PCT/US2016/060273; 12 pages.
Brinkman-Van Der Linden et al. "CD33/Siglec-3 Binding Specificity, Expression Pattern, and Consequences of Gene Deletion in Mice," Molecular and Cellular Biology, 2003, vol. 23, No. 12, pp. 4199-4206.
Abrahimi et al. "Efficient Gene Disruption in Cultured Primary Human Endothelial Cells by CRISPR/Cas9," Circulation Research, 2015, vol. 117, Iss. 2, pp. 121-128.
Doench et al. "Rational design of highly active sgRNAs for CRISPR-Cas9-mediated gene inactivation," Nature Biotechnology, 2014, vol. 32, pp. 1262-1267 (pp. 1-17 for citations).
Kim et al. "Abstract 273: Genome Editing Using CRISPR-Cas9 to Increase the Therapeutic Index of Antigen-Specific Immunotherapy in Acute Myeloid Leukemia," American Society of Gene & Cell Therapy 19th Annual Meeting, Molecular Therapy, May 4, 2016 (May 4, 2016), vol. 24, Suppl. 1, p. S108.
Sotillo et al. "Convergence of Acquired Mutations and Alternative Splicing of CD19 Enables Resistance to CART-19 Immunotherapy," Cancer Discovery, 2015, vol. 5, Iss. 12, pp. 1282-1295.
Kim et al. "Engineering Resistance to Antigen-Specific Immunotherapy in Normal Hematopoietic Stem Cells by Gene Editing to Enable Targeting of Acute Myeloid Leukemia," American Society of Heamatology 58th Annual Meeting & Exposition, Dec. 5, 2016 (Dec. 5,

(56) References Cited

OTHER PUBLICATIONS

2016), pp. 1-2. Retrieved from the Internet: <https://ash.confex.com/ash/2016/webprogram/Paper89763.html> on Dec. 28, 2016 (Dec. 28, 2016).
International Search Report and Written Opinion dated Jan. 9, 2017, corresponding to International PCT Application No. PCT/US2016/057339; 26 pages.
Supplementary European Search Report dated Apr. 25, 2019 corresponding to European Patent Application No. EP16856410.2, 9 pages.
Lajaunias et al. (European Journal of Immunology, 2005, 35:243-251) (Year: 2005).

Stain with anti-CD3TCRz, ab
Epitope: C-term CD3z

| Construct | MW kDa |
|---|---|
| CART1 | 55.3AAAA |
| CART2 | 56.3 |
| CART3 | 61 |

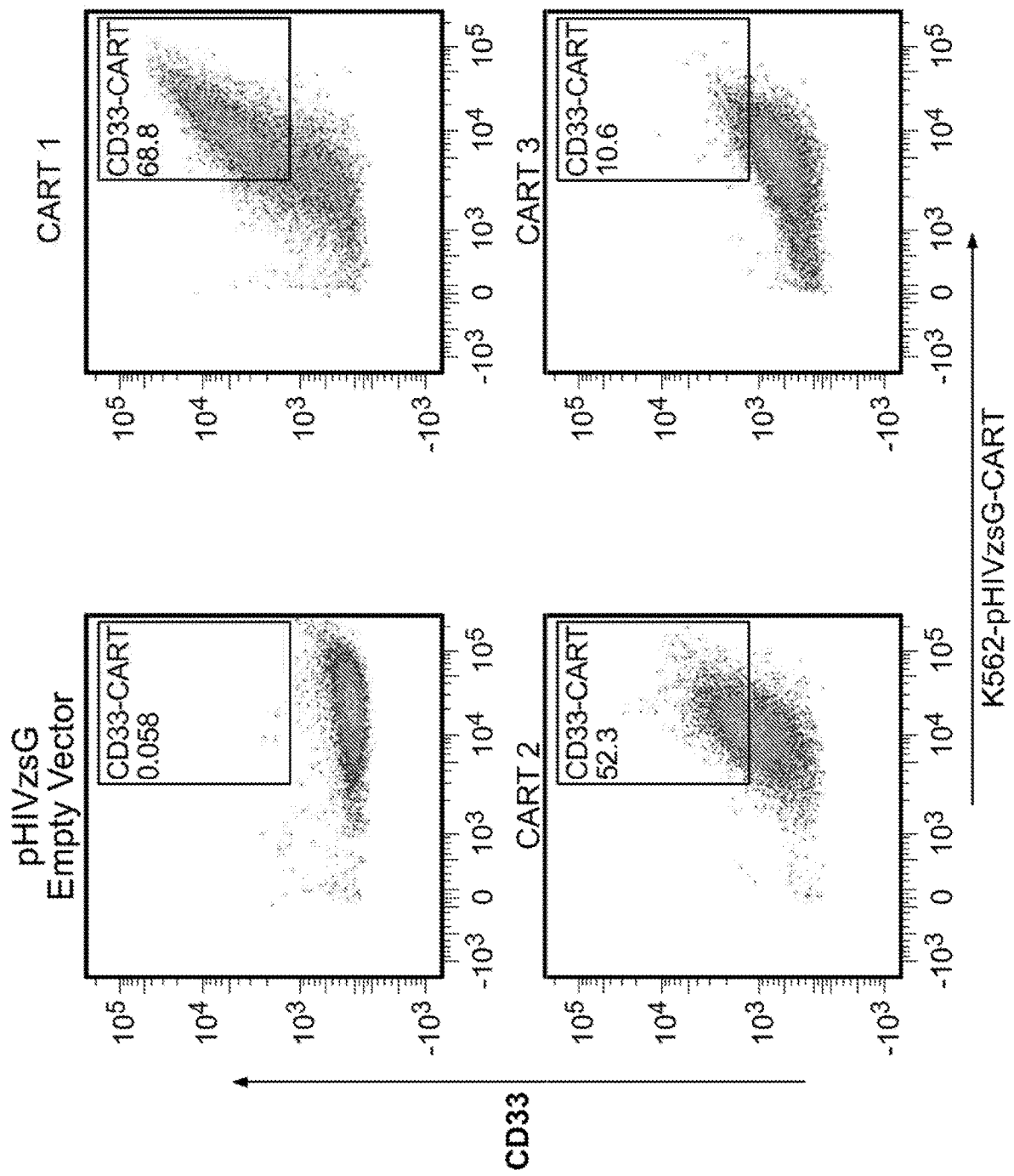

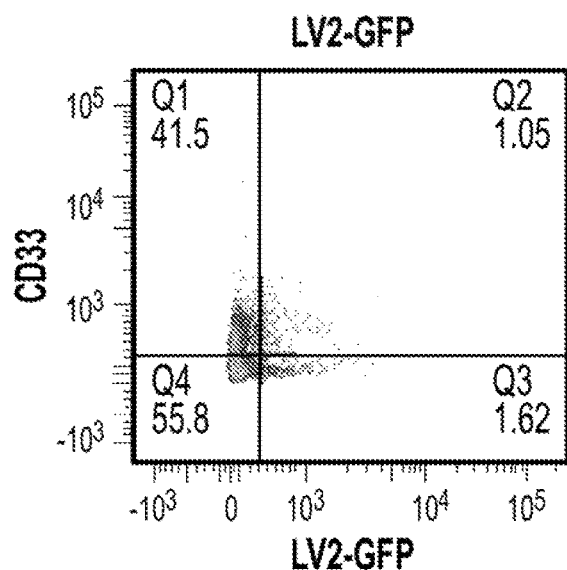
FIG. 17A
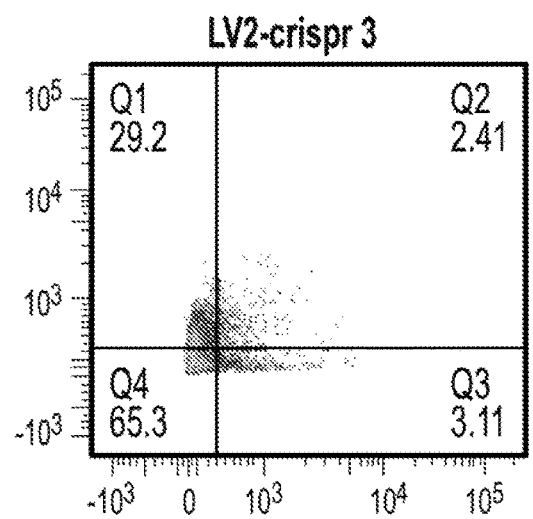 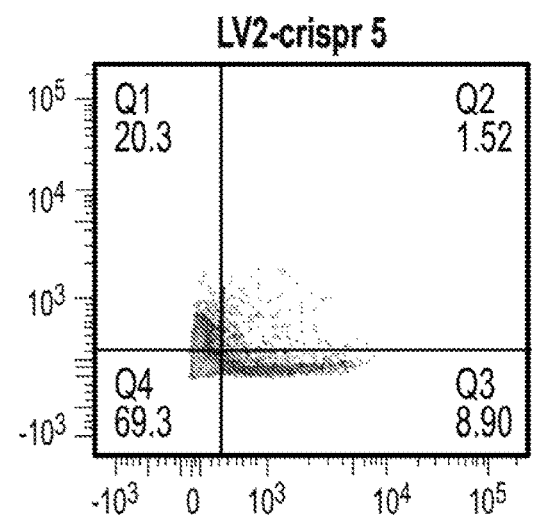
FIG. 17B                    FIG. 17C

COMPOSITIONS AND METHODS FOR INHIBITION OF LINEAGE SPECIFIC ANTIGENS

CROSS REFERENCE TO RELATED APPLICATIONS

This application is a continuation of U.S. patent Ser. No. 16/174,089, filed Oct. 29, 2018, now U.S. Pat. No. 10,660,919, issued May 26, 2020, which is a continuation of U.S. patent Ser. No. 15/655,432 filed Jul. 20, 2017, now U.S. patent Ser. No. 10/137,155, issued Nov. 27, 2018, which is a continuation of International Patent Application No. PCT/US2016/057339 filed Oct. 17, 2016, which claims benefit of U.S. Provisional Application No. 62/242,685 filed Oct. 16, 2015, all of which are incorporated by reference, as if expressly set forth in their respective entireties herein.

INCORPORATION-BY-REFERENCE OF SEQUENCE LISTING

A sequence listing, filed as the ASCII text file "01001_004965-US3_SeqListing.txt" having a file size of 66,369 bytes, is incorporated herein by reference in its entirety.

BACKGROUND OF DISCLOSURE

Despite decades of attempts, curative immunological therapy against cancer has been very difficult to achieve, with the fundamental basis being antigen-recognition capacity, either by antibodies or through T cells (via the T cell receptor) (Cousin-Frankel, Science (2013) 342:1432). Antibody-based immunotherapies have been used extensively against cancer in instances where the target antigen is up-regulated in tumor cells as compared to normal cells (e.g., Her-2 in Her-2 amplified breast cancer), or in cases where the tumor cells express an antigen that can be recognized by the antibody or an antibody-toxin conjugate (e.g., Rituximab against CD20) (Baselga et al., *Annals Oncology* (2001) 12:S35). While clinical trials using antibody-based immunotherapies have shown improved patient survival in a limited number of cancer types (usually when combined with standard chemotherapy), these effects are often accompanied by significant safety and efficacy concerns (Cousin-Frankel Cancer, *Science* (2013) 342:1432).

Effective T cell therapies against cancers have been even more difficult to achieve clinically (Schmitt et al., *Hum. Gene Ther*. (2009) 20(11):1240). An effective T cell therapy against cancer relies on a T cell with a high affinity binding directed against an antigen on a cancer cell. Chimeric antigen receptor T cells (CAR T cells) are widely used to recognize antigens on cells with both high affinity and specificity and without the requirement for accessory recognition molecules, such as HLA antigens to "present" peptides. The T cell receptor of a CAR T cells is "swapped" with an antigen-binding heavy and light chains, thereby obviating the need for HLA accessory molecules. The recombinant CAR T receptor is fused to signaling domains leading to activation of the T cell upon binding of the CAR T receptor to the target antigen.

The clinical use of CAR T cells has been limited to targeting a narrow range of cell surface antigens, further supporting the need for improved and novel approaches in the treatment of cancer. In particular, new approaches are needed for diseases such as acute myeloid leukemia (AML) in which the outcomes in older patients who are unable to receive intensive chemotherapy, the current standard of care, remains very poor, with a median survival of only 5 to 10 months (Dohner et al., *NEJM* (2015) 373:1136).

Described herein are novel approaches to cancer immunotherapy that targets certain classes of lineage-specific cell-surface antigens on tumor cells. The CAR T cell treatment is then combined with replacement of the non-tumor cells by infusion or reinfusion of a modified population of cells that are deficient for the lineage-specific cell-surface antigen. Recurrence of the tumor is prevented or decreased by maintaining surveillance of the patient in vivo with the CAR T cells.

SUMMARY OF DISCLOSURE

The present disclosure is based, at least in part, on the discovery that agents comprising an antigen-binding fragment that binds a lineage-specific cell-surface antigen (e.g., immune cells expression a chimeric receptor that targets CD33) selectively cause cell death of cells expressing the lineage-specific cell-surface antigen, whereas cells that are deficient for the antigen (e.g., genetically engineered hematopoietic cells) evade cell death caused thereby. Based on such findings, it would have been expected that immunotherapies involving the combination of an agent targeting a lineage-specific cell-surface antigen, for example, CAR-T cells targeting CD33, and hematopoietic cells that are deficient in the lineage-specific cell-surface antigens (e.g., CD33) would provide an efficacious method of treatment for hematopoietic malignancies.

One aspect of the present disclosure provides methods for treating a hematopoietic malignancy, the method comprising administering to a subject in need thereof (i) an effective amount of an agent targeting a lineage-specific cell-surface antigen, wherein the agent comprises an antigen-binding fragment that binds the lineage-specific cell-surface antigen; and (ii) a population of hematopoietic cells that are deficient in the lineage-specific cell-surface antigen. In some embodiments, the agent can be an immune cell (e.g., a T cell) expressing a chimeric receptor that comprises the antigen-binding fragment that binds the lineage-specific cell-surface antigen. In some embodiments, the immune cells, the hematopoietic cells, or both, are allogeneic or autologous. In some embodiments, the hematopoietic cells are hematopoietic stem cells (e.g., CD34$^+$/CD33$^-$ HSCs). In some embodiments, the hematopoietic stem cells can be obtained from bone marrow cells or peripheral blood mononuclear cells (PBMCs).

In some embodiments, the antigen-binding fragment binds a lineage-specific cell-surface antigen that is a type 2 lineage-specific cell-surface antigen (e.g., CD33). In some embodiments, the antigen-binding fragment binds a lineage-specific cell-surface antigen that is a type 1 lineage-specific cell-surface antigen (e.g., CD19).

In some embodiments, the antigen-binding fragment in the chimeric receptor is a single-chain antibody fragment (scFv) that specifically binds the lineage-specific cell-surface antigen, which can be a human protein, such as human CD33 or CD19. In some embodiments, the scFv binds to human CD33 and comprises a heavy chain variable region, which has the same complementary determining regions (CDRs) as those in SEQ ID NO: 12, and a light chain variable region, which has the same CDRs as those in SEQ ID NO: 13. In one example, the scFv comprises a heavy chain variable domain having the amino acid sequence of SEQ ID NO: 12 and a light chain variable domain having the amino acid sequence of SEQ ID NO: 13.

The chimeric receptors may further comprise (a) a hinge domain, (b) a transmembrane domain, (c) at least one co-stimulatory domain, (d) a cytoplasmic signaling domain, or (e) a combination thereof. In some embodiments, the chimeric receptor comprises at least one co-stimulatory signaling domain, which can be derived from a co-stimulatory receptor of CD27, CD28, 4-1BB, OX40, CD30, CD40, PD-1, ICOS, lymphocyte function-associated antigen-1 (LFA-1), CD2, CD7, LIGHT, NKG2C, B7-H3, GITR, HVEM, or a combination thereof. In some embodiments, the at least one co-stimulatory signaling domain is a hybrid co-stimulatory domain comprising a signaling domain of CD28 and a signaling domain of ICOS. In one example, the at least one co-stimulatory signaling domain is from CD28 and the chimeric receptor further comprises a second co-stimulatory signaling domain from 4-1BB or ICOS.

In some embodiments, the chimeric receptor comprises a cytoplasmic signaling domain, which is from CD3'. In some embodiments, the chimeric receptor comprises a hinge domain, which is from CD8α or CD28α. In some embodiments, the chimeric receptor comprises a transmembrane domain, which is from CD8, CD28, or ICOS.

In some embodiments, the chimeric receptor comprises, from N terminus to C terminus, (i) a scFv that binds to the lineage-specific cell-surface antigen (e.g., CD33 or CD19), a hinge domain from CD8α, a transmembrane domain from CD, a costimulatory domain from 4-1BB, and a cytoplasmic signaling domain from CD3ζ; (ii) a scFv that binds to the lineage-specific cell-surface antigen (e.g., CD33 or CD19), a hinge domain from CD8α, a transmembrane domain from CD28, a costimulatory domain from CD28, and a cytoplasmic signaling domain from CD3ζ; or (iii) a scFv that binds to the lineage-specific cell-surface antigen (e.g., CD33 or CD19), a hinge domain from CD8α, a transmembrane domain from CD28, a first costimulatory domain from CD28, a second costimulatory domain from 4-1BB, and a cytoplasmic signaling domain from CD3ζ.

In any of the methods described herein, the subject may have Hodgkin's lymphoma, non-Hodgkin's lymphoma, leukemia, or multiple myeloma. In some examples, the subject has leukemia, which is acute myeloid leukemia, chronic myelogenous leukemia, acute lymphoblastic leukemia, or chronic lymphoblastic leukemia.

In another aspect, the present disclosure provides a nucleic acid comprising a nucleotide sequence encoding any of the chimeric receptors as described herein. The chimeric receptor may comprise an antigen-binding fragment that binds CD33, a transmembrane domain, and a cytoplasmic signaling domain, such as a cytoplasmic signaling domain from CD3ζ. The antigen-binding fragment (e.g., a scFv fragment) comprises a heavy chain variable region having the same CDRs as those in SEQ ID NO: 12, and a light chain variable region having the same CDRs as those in SEQ ID NO: 13. In some embodiments, the scFv comprises a heavy chain variable domain having the amino acid sequence of SEQ ID NO: 12 and a light chain variable domain having the amino acid sequence of SEQ ID NO: 13.

Other aspects of the present disclosure provide vectors comprising any of the nucleic acids provided herein. Also within the scope of the present disclosure are chimeric receptors encoded by the nucleic acids described herein and immune cells (e.g., T cells) expressing such a chimeric receptor. In some embodiments, the immune cells can be obtained from a patient having a hematopoietic malignancy.

Another aspect of the present disclosure provides genetically engineered hematopoietic cells (e.g., HSCs) that are deficient in a lineage-specific cell-surface antigen (e.g., CD33, CD19), which presents on the hematopoietic cell before genetic engineering. In some embodiments, the whole or a portion of an endogenous gene encoding the lineage-specific cell-surface antigen is deleted, for example by genome editing (e.g., involving a zinc finger nuclease (ZFN), a transcription activator-like effector-based nuclease (TALEN), or a CRISPR-Cas system). In some embodiments, the lineage-specific cell-surface antigen is CD33 and a portion of the immunoglobulin constant (IgC) domain of the CD33 is deleted. In some embodiments, the hematopoietic cell is a hematopoietic stem cell (e.g., CD34$^+$/CD33$^-$ cell).

In some embodiments, the hematopoietic stem cells can be obtained from bone marrow cells or peripheral blood mononuclear cells (PBMCs).

Also provided herein are methods of producing a cell that is deficient in a lineage-specific cell-surface antigen as described herein. The methods comprises providing a cell, and introducing into the cell (i) a nucleic acid that comprises a nucleotide sequence of a CRISPR-Cas system guide RNA (gRNA), which hybridizes to a portion of the nucleotide sequence that encodes the lineage-specific cell-surface antigen (e.g., CD33, CD19), and (ii) a Cas endonuclease (e.g., Cas9 or Cpf1). The nucleic acid that comprises a nucleotides sequence of a CRISPR-Cas system gRNA and a Cas nuclease may, for example, be encoded on the same nucleic acid or on different nucleic acids, or introduced into the cell as a pre-formed ribonucleoprotein complex. In some embodiments, the portion of the nucleotide sequence to which the gRNA hybridizes consists of 18-22 nucleotides. In some examples, the gRNA comprises the nucleotide sequence of SEQ ID NO: 11 or 28-31.

In some embodiments, the cell is a hematopoietic cell, such as a hematopoietic stem cell (e.g., CD34$^+$).

Also within the scope of the present disclosure are kits comprising (i) an immune cell of claim B13 an agent that target a lineage-specific, cell-surface antigen, which comprises an antigen binding fragment that binds the lineage-specific cell-surface antigen; and (ii) a population of hematopoietic cells (e.g., hematopoietic stem cells) that are deficient in the lineage-specific cell-surface antigen. In some embodiments, the agent that targets the lineage-specific, cell-surface antigen is an immune cell expressing a chimeric receptor, which comprises the antigen-binding fragment the lineage-specific cell-surface antigen.

Further, the present disclosure provides pharmaceutical compositions comprising any of the immune cells targeting a lineage-specific cell-surface antigen and/or any of the hematopoietic cells that are deficient in the lineage-specific cell-surface antigen for use in treating a hematopoietic malignancy; as well as uses of the immune cells and hematopoietic cells for manufacturing a medicament for use in treating a hematopoietic malignancy.

The details of one of more embodiments of the disclosure are set forth in the description below. Other features or advantages of the present disclosure will be apparent from the detailed description of several embodiments and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 7A: a generic chimeric receptor targeting CD33 comprising an anti-CD33 scFv, hinge domain, transmembrane domain, co-stimulatory domain, and signaling domain. FIG. 7B: a chimeric receptor targeting CD33 comprising an anti-CD33 scFv, hinge domain from CD8, transmembrane domain from CD8, and intracellular domains from CD28 and CD3ζ. FIG. 7C: a chimeric receptor targeting CD33 comprising an anti-CD33 scFv, hinge domain from CD8, transmembrane domain from CD8, and intracellular domains from ICOS (or CD27, 4-1BB, or OX-40) and CD3ζ. FIG. 7D: a chimeric receptor targeting CD33 comprising an anti-CD33 scFv, hinge domain from CD8, transmembrane domain from CD8, and intracellular domains from OX40, CD28, and CD3ζ.

FIG. 9A: Western blot using a primary antibody that recognizes CD3ζ. The table provides the estimated molecular weight of each of the chimeric receptors tested. FIG. 9B: Flow cytometric analysis showing an increase in the population of cells that stain positive for the anti-CD33 chimeric receptor.

FIGS. 10A-10C show the anti-CD33 chimeric receptors bind to CD33. FIG. 10A: Ponceau stained protein gel. Lanes 1, 3, 5: CD33 molecule. Lanes 2, 4, 6: CD33 mol+APC Conjugate. FIG. 10B: Western blot using a primary antibody that recognizes CD3ζ. Lanes 1, 3, and 5 contain the chimeric receptors co-incubated with CD33 molecules, and lanes 2, 4, and 6 contain the chimeric receptors co-incubated with a CD33-APC conjugate. FIG. 10C: Flow cytometric analysis showing an increase in the population of cells that express anti-CD33 chimeric receptors and bind CD33.

FIG. 11A: CART1 and CART2 compared to empty HIVzsG vector. FIG. 11B: CART3 compared to empty HIVzsG vector.

FIG. 12A: unsorted population of K562 cells pretreated with CD33-targeting CRISPR/Cas reagents. FIG. 12B: single clones of K562 cells deficient in CD33. The columns, from left to right, correspond to empty HIVzsG vector, CART1, CART2, and CART3.

FIG. 13A: sorting of cells based on expression of T cell markers C4$^+$, CD8$^+$, or both CD4$^+$ CD8$^+$. FIG. 13B: relative expression of CD33 on the indicated populations of primary T cells.

FIG. 14A: CD4$^+$ T cells. FIG. 14B: CD4$^+$/CD8$^+$ (CD 4/8) and CD8$^+$ (CD8).

FIG. 16A: flow cytometric analysis of the indicated cell populations at day 1+50 μM hemin. FIG. 16B: flow cytometric analysis of the indicated cell populations at day 9. FIG. 16C: MTT cell proliferation assay.

FIGS. 17A-17C show flow cytometric analysis of CD33 editing in human CD34$^+$ cells using the CRISPR/Cas9 system and two different gRNAs (crispr3, bottom left panel, and crispr5, bottom right panel). FIG. 17A: flow cytometric analysis of CD33 editing in human CD34$^+$ cells using the CRISPR/Cas9 system. FIG. 17B: crispr3. FIG. 17C: crispr5.

DETAILED DESCRIPTION OF DISCLOSURE

Figure 1:
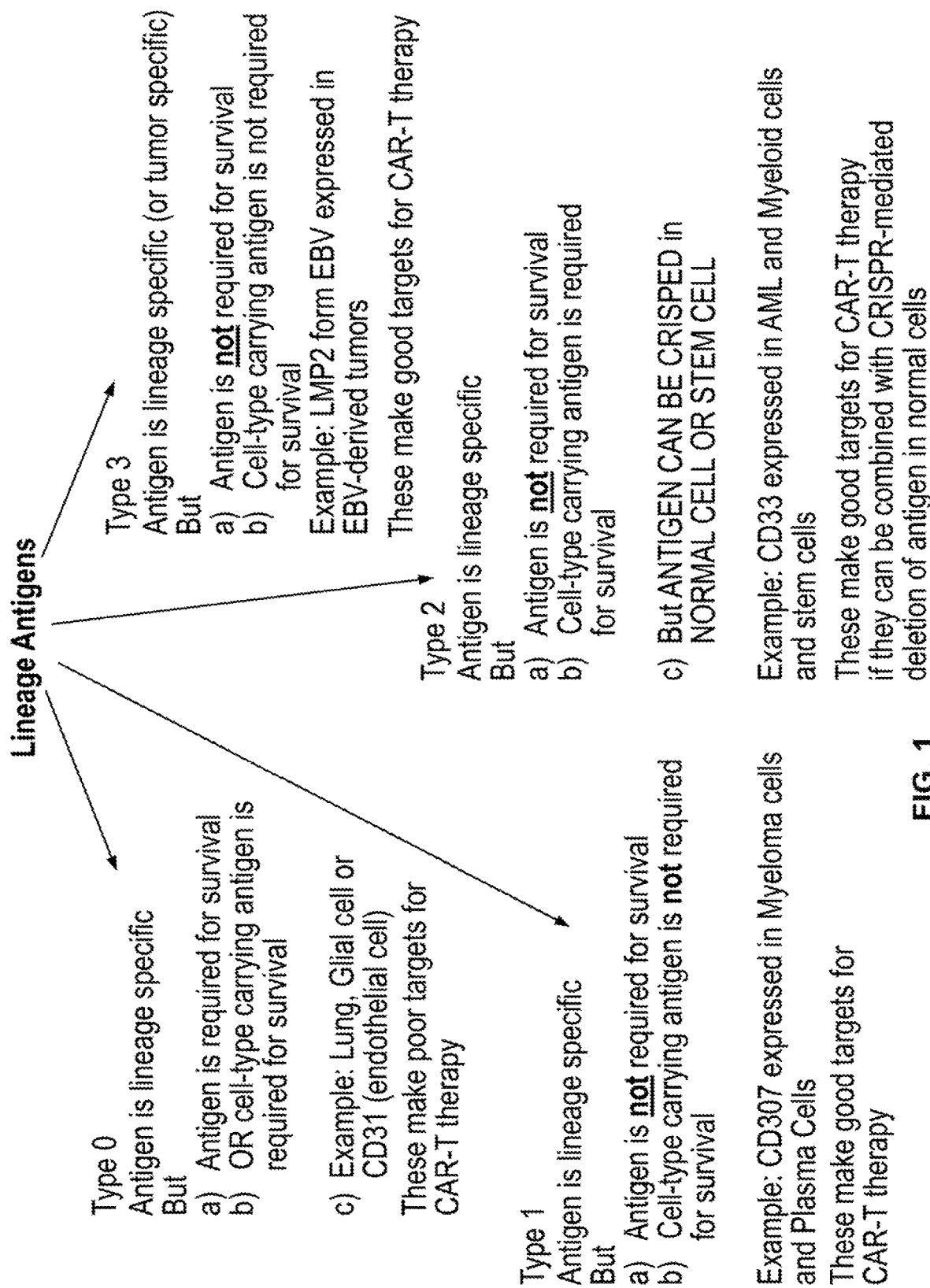
FIG. 1 presents an exemplary illustration of type 0, type 1, type 2, and type 3 lineage-specific antigens.

Cancer immunotherapies targeting antigens present on the cell surface of a cancer cell is particularly challenging when the target antigen is also present on the cell surface of normal, non-cancer cells that are required or critically involved in the development and/or survival of the subject. Targeting these antigens may lead to deleterious effects in the subject due to cytotoxic effects of the immunotherapy toward such cells in addition to the cancer cells.

The methods, nucleic acids, and cells described herein allow for targeting of antigens (e.g., type 1 or type 2 antigens) that are present not only on cancer cells but also cells critical for the development and/or survival of the subject. The method involves: (1) reducing the number of cells carrying the target lineage-specific cell-surface antigen using an agent that targets such an antigen; and (2) replacement of the normal cells (e.g., non-cancer cells) that present the antigen and thus can be killed due to administration of the agent with hematopoietic cells that are deficient for the lineage-specific cell-surface antigen. The methods described herein can maintain surveillance for target cells, including cancer cells, that express a lineage-specific cell-surface antigen of interest and also maintain the population of non-cancer cells expressing the lineage-specific antigen, which may be critical for development and/or survival of the subject.

Accordingly, described herein are the co-use of immune cells expressing chimeric receptors comprising an antigen-binding fragment that targets a lineage-specific cell-surface antigen such as CD33 or CD19 and hematopoietic cells such as hematopoietic stem cells (HSCs) that are deficient in the lineage-specific cell-surface antigen for treating a hematopoietic malignancy. Also provided herein are the chimeric receptors, nucleic acids encoding such, vectors comprising such, and immune cells (e.g., T cells) expressing such a chimeric receptor. The present disclosure also provides genetically engineered hematopoietic cells that are deficient in a lineage-specific antigen such as those described herein, as well as methods (e.g., genome editing methods) for making such.

Definitions

The terms "subject," "individual," and "patient" are used interchangeably, and refer to a vertebrate, preferably a mammal such as a human. Mammals include, but are not limited to, human primates, non-human primates or murine, bovine, equine, canine or feline species. In the context of the present disclosure, the term "subject" also encompasses tissues and cells that can be cultured in vitro or ex vivo or manipulated in vivo. The term "subject" can be used interchangeably with the term "organism".

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Examples of polynucleotides include, but are not limited to, coding or non-coding regions of a gene or gene fragment, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. One or more nucleotides within a polynucleotide can further be modified. The sequence of nucleotides may be interrupted by non-nucleotide components. A polynucleotide may also be modified after polymerization, such as by conjugation with a labeling agent.

The term "hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi-stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the present disclosure are not naturally-occurring as a whole. Parts of the vectors can be naturally-occurring. The non-naturally occurring recombinant expression vectors of the present disclosure can comprise any type of nucleotides, including, but not limited to DNA and RNA, which can be single-stranded or double-stranded, synthesized or obtained in part from natural sources, and which can contain natural, non-natural or altered nucleotides.

"Transfection," "transformation," or "transduction," as used herein, refer to the introduction of one or more exogenous polynucleotides into a host cell by using physical or chemical methods.

"Antibody," "fragment of an antibody," "antibody fragment," "functional fragment of an antibody," or "antigen-binding portion" are used interchangeably to mean one or more fragments or portions of an antibody that retain the ability to specifically bind to a specific antigen (Holliger et al., *Nat. Biotech.* (2005) 23(9): 1126). The present antibodies may be antibodies and/or fragments thereof. Antibody fragments include Fab, F(ab')2, scFv, disulfide linked Fv, Fc, or variants and/or mixtures. The antibodies may be chimeric, humanized, single chain, or bi-specific. All antibody isotypes are encompassed by the present disclosure, including, IgA, IgD, IgE, IgG, and IgM. Suitable IgG subtypes include IgG1, IgG2, IgG3 and IgG4. An antibody light or heavy chain variable region consists of a framework region interrupted by three hypervariable regions, referred to as complementarity determining regions (CDRs). The CDRs of the present antibodies or antigen-binding portions can be from a non-human or a human source. The framework of the present antibodies or antigen-binding portions can be human, humanized, non-human (e.g., a murine framework modified to decrease antigenicity in humans), or a synthetic framework (e.g., a consensus sequence).

The present antibodies or antigen-binding portions can specifically bind with a dissociation constant ($K_D$) of less than about $10^{-7}$ M, less than about $10^{-8}$ M, less than about $10^{-9}$ M, less than about $10^{-10}$ M, less than about $10^{-11}$ M, or less than about $10^{-12}$ M. Affinities of the antibodies according to the present disclosure can be readily determined using conventional techniques (see, e.g., Scatchard et al., *Ann. N.Y. Acad. Sci.* (1949) 51:660; and U.S. Pat. Nos. 5,283,173, 5,468,614, or the equivalent).

The terms "chimeric receptor," "Chimeric Antigen Receptor," or alternatively a "CAR" are used interchangeably throughout and refer to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below, Lee et al., *Clin. Cancer Res.* (2012) 18(10):2780; Jensen et al., *Immunol Rev.* (2014) 257(1):127: www.cancer.gov/about-cancer/treatment/research/car-t-cells. In one embodiment, the stimulatory molecule is the zeta chain associated with the T cell receptor complex. In one aspect, the cytoplasmic signaling domain further comprises one or more functional signaling domains derived from at least one costimulatory molecule as defined below. The costimulatory molecule may also be 4-1BB (i.e., CD137), CD27 and/or CD28 or fragments of those molecules. In another aspect, the CAR comprises a chimeric fusion protein comprising an extracellular antigen recognition domain, a transmembrane domain and an intracellular signaling domain comprising a functional signaling domain derived from a stimulatory molecule. The CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. Alternatively, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. The CAR can also comprise a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. The antigen recognition moiety of the CAR encoded by the nucleic acid sequence can contain any lineage specific, antigen-binding antibody fragment. The antibody fragment can comprise one or more CDRs, the variable region (or portions thereof), the constant region (or portions thereof), or combinations of any of the foregoing.

The term "signaling domain" refers to the functional portion of a protein which acts by transmitting information within the cell to regulate cellular activity via defined signaling pathways by generating second messengers or functioning as effectors by responding to such messengers.

The term "zeta" or alternatively "zeta chain", "CD3-zeta" or "TCR-zeta" is defined as the protein provided as GenBank accession numbers NP_932170, NP_000725, or XP_011508447; or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation.

The term "genetically engineered" or "genetically modified" refers to cells being manipulated by genetic engineering, for example by genome editing. That is, the cells contain a heterologous sequence which does not naturally occur in said cells. Typically, the heterologous sequence is introduced via a vector system or other means for introducing nucleic acid molecules into cells including liposomes. The heterologous nucleic acid molecule may be integrated into the genome of the cells or may be present extra-chromosomally, e.g., in the form of plasmids. The term also includes embodiments of introducing genetically engineered, isolated CAR polypeptides into the cell.

The term "autologous" refers to any material derived from the same individual to whom it is later to be re-introduced into the same individual.

The term "allogeneic" refers to any material derived from a different animal of the same species as the individual to whom the material is introduced. Two or more individuals are said to be allogeneic to one another when the genes at one or more loci are not identical.

The term "cell lineage" refers to cells with a common ancestry and developing from the same type of identifiable cell into specific identifiable/functioning cells. The cell lineages used herein include, but are not limited to, respiratory, prostatic, pancreatic, mammary, renal, intestinal, neural, skeletal, vascular, hepatic, hematopoietic, muscle or cardiac cell lineages.

The term "inhibition" when used in reference to gene expression or function of a lineage specific antigen refers to a decrease in the level of gene expression or function of the lineage specific antigen, where the inhibition is a result of interference with gene expression or function. The inhibition may be complete, in which case there is no detectable expression or function, or it may be partial. Partial inhibition can range from near complete inhibition to a near absence of inhibition. By eliminating particular target cells, CAR T cells may effectively inhibit the overall expression of particular cell lineage.

Cells such as hematopoietic cells that are "deficient in a lineage-specific antigen" refers to cells having a substantially reduced expression level of the lineage-specific antigen as compared with their naturally-occurring counterpart, e.g., endogenous hematopoietic cells of the same type, or cells that do not express the lineage-specific antigen, i.e., not detectable by a routine assay such as FACS. In some instances, the express level of a lineage-specific antigen of cells that are "deficient in the antigen" can be lower than about 40% (e.g., 30%, 20%, 15%, 10%, 5% or lower) of the expression level of the same lineage-specific antigen of the naturally-occurring counterpart. As used herein, the term "about" refers to a particular value +/−5%. For example, an expression level of about 40% may include any amount of expression between 35%-45%.

Agents Targeting Lineage-Specific Cell-Surface Antigens

Aspects of the disclosure provide agents targeting a lineage-specific cell-surface antigen, for example on a target cancer cell. Such an agent may comprise an antigen-binding fragment that binds and targets the lineage-specific cell-surface antigen. In some instances, the antigen-binding fragment can be a single chain antibody (scFv) specifically binding to the lineage-specific antigen.

A. Lineage-Specific Cell-Surface Antigens

As used herein, the terms "lineage-specific cell-surface antigen" and "cell-surface lineage-specific antigen" may be used interchangeably and refer to any antigen that is sufficiently present on the surface of a cell and is associated with one or more populations of cell lineage(s). For example, the antigen may be present on one or more populations of cell lineage(s) and absent (or at reduced levels) on the cell-surface of other cell populations.

In general, lineage-specific cell-surface antigens can be classified based on a number of factors such as whether the antigen and/or the populations of cells that present the antigen are required for survival and/or development of the host organism. A summary of exemplary types of lineage-specific antigens is provide in Table 1 below. See also FIG. 1.

TABLE 1

Classification of Lineage Specific Antigens

| Type of Lineage Specific Antigen | Characteristics of the Lineage Specific Antigen |
|---|---|
| Type 0 | a) antigen is required for survival of an organism and<br>b) cell type carrying type 0 antigen is required for survival of an organism and is not unique to a tumor, or tumor-associated virus |
| Type 1 | a) antigen is not required for survival of an organism and<br>b) cell type carrying type 1 antigen is not required for survival of an organism |
| Type 2 | a) antigen is not required for survival of an organism and<br>b) cell type carrying type 2 antigen is required for the survival of an organism |
| Type 3 | a) antigen is not required for the survival of an organism and<br>b) cell type carrying antigen is not required for survival of an organism<br>c) The antigen is unique to a tumor, or a tumor associated virus<br>An example is the LMP-2 antigen in EBV infected cells, including EBV infected tumor cells (Nasopharyngeal carcinoma, and Burkitts Lymphoma) |

As shown in Table 1 and FIG. 1, type 0 lineage-specific cell-surface antigens are necessary for the tissue homeostasis and survival, and cell types carrying type 0 lineage-specific cell-surface antigen may be also necessary for survival of the subject. Thus, given the importance of type 0 lineage-specific cell-surface antigens, or cells carrying type 0 lineage-specific cell-surface antigens, in homeostasis and survival, targeting this category of antigens may be challenging using conventional CAR T cell immunotherapies, as the inhibition or removal of such antigens and cell carrying such antigens may be detrimental to the survival of the subject. Consequently, lineage-specific cell-surface antigens (such as type 0 lineage-specific antigens) and/or the cell types that carry such antigens may be required for the survival, for example because it performs a vital non-redundant function in the subject, then this type of lineage specific antigen may be a poor target for CAR T cell based immunotherapy.

Figure 2:
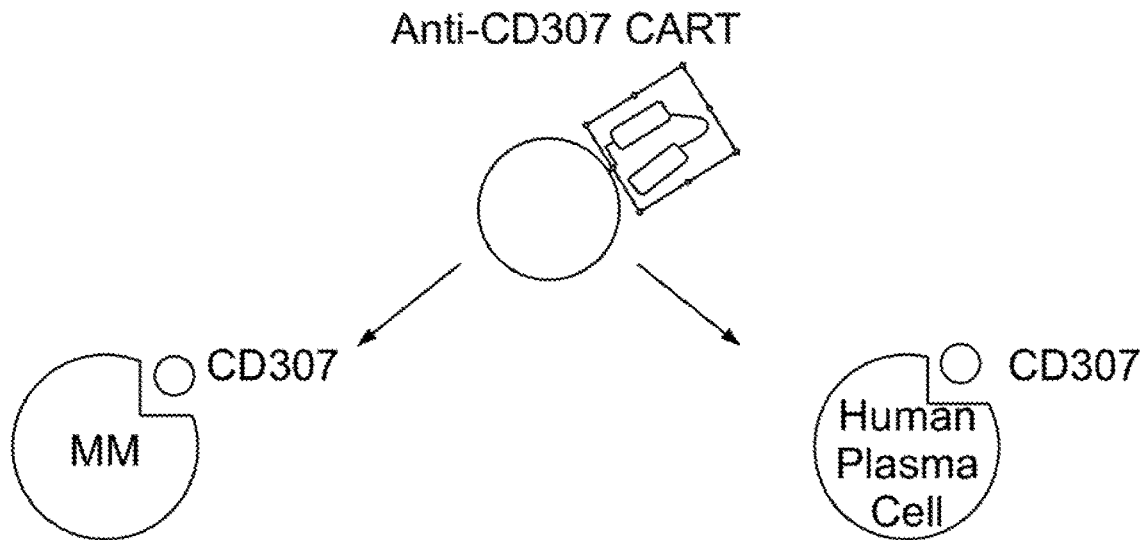
FIG. 2 is a schematic showing an immune cell expressing a chimeric receptor that targets the type 0 lineage-specific cell-surface antigen, CD307. Multiple myeloma (MM) cells expressing CD307 as well other cells expressing CD307, such as plasma cells, are targeted by the immune cells expressing the anti-CD307 chimeric receptor.

In contrast to type 0 antigens, type 1 cell-surface lineage-specific antigens and cells carrying type 1 cell-surface lineage-specific antigens are not required for tissue homeostasis or survival of the subject. Targeting type 1 cell-surface lineage-specific antigens is not likely to lead to detrimental consequences in the subject. For example, a CAR T cell engineered to target CD307, a type 1 antigen expressed uniquely on both normal plasma cells and multiple myeloma (MM) cells would lead to elimination of both cell types (FIG. 2) (Elkins et al., *Mol Cancer Ther.* 10:2222 (2012)). However, since the plasma cell lineage is expendable for the survival of the organism, CD307 and other type 1 lineage specific antigens are antigens that are suitable for CAR T cell based immunotherapy. Lineage specific antigens of type 1 class may be expressed in a wide variety of different tissues, including, ovaries, testes, prostate, breast, endometrium, and pancreas. In some embodiments, the agent targets a cell-surface lineage-specific antigen that is a type 1 antigen.

Figure 3:
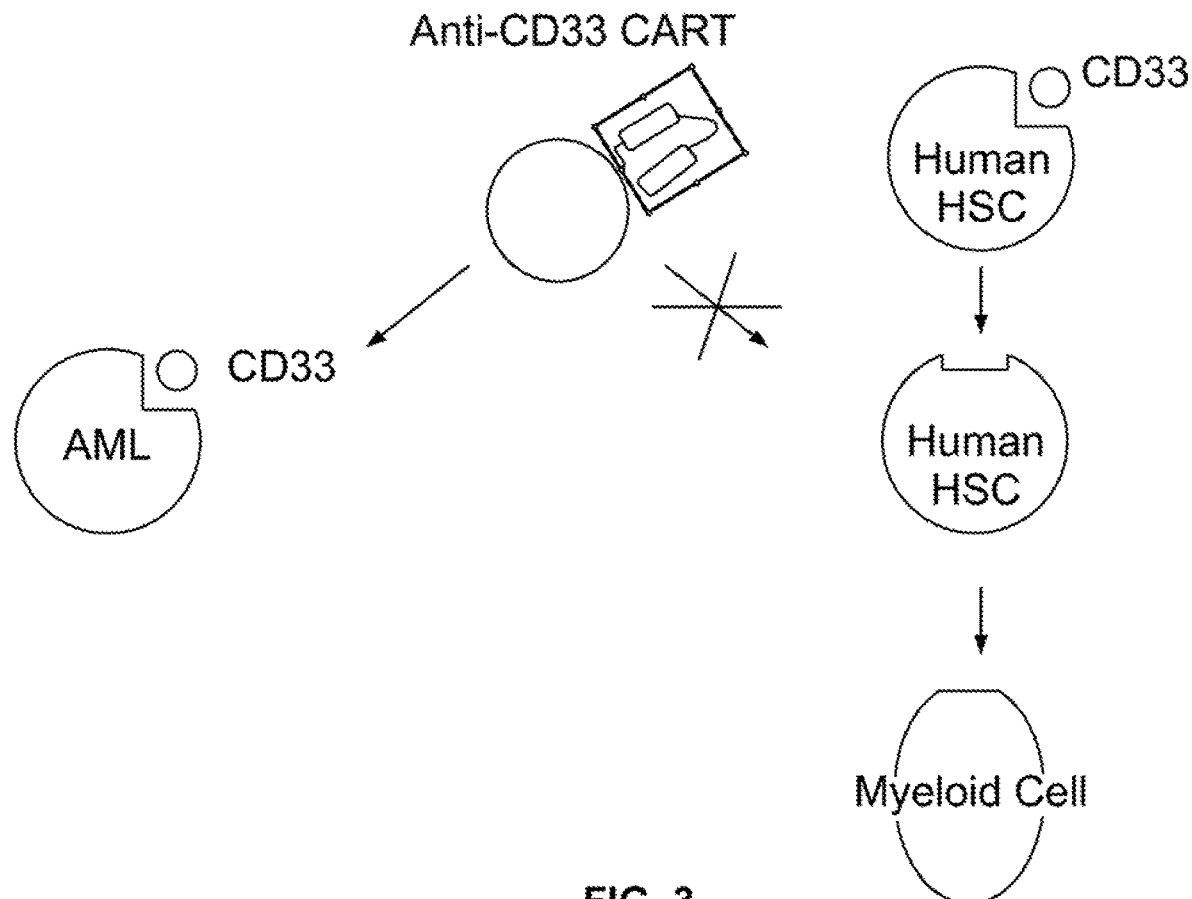
FIG. 3 is a schematic showing an immune cell expressing a chimeric receptor that targets the type 2 lineage-specific cell-surface antigen, CD33. Acute myeloid leukemia (AML) cells expressing CD33. Human hematopoietic stem cells (HSC) are genetically engineered to be deficient in CD33 and therefore not recognized by the immune cells expressing the anti-CD33 chimeric receptor. The HSC are able to give rise to myeloid cells.

Targeting type 2 antigens presents a significant difficulty as compared to type 1 antigens. Type 2 antigens are those characterized where: (1) the antigen is dispensable for the survival of an organism (i.e., is not required for the survival), and (2) the cell lineage carrying the antigen is indispensable for the survival of an organism (i.e., the particular cell lineage is required for the survival). For example, CD33 is a type 2 antigen expressed in both normal myeloid cells as well as in Acute Myeloid Leukemia (AML) cells (Dohner et al., *NEJM* 373:1136 (2015)). As a result, a CAR T cell engineered to target CD33 antigen could lead to the killing of both normal as well as AML cells, which may be incompatible with survival of the subject (FIG. 3). In some embodiments, the agent targets a cell-surface lineage-specific antigen that is a type 2 antigen.

A wide variety of antigens may be targeted by the methods and compositions of the present disclosure. Monoclonal antibodies to these antigens may be purchased commercially or generated using standard techniques, including immunization of an animal with the antigen of interest followed by conventional monoclonal antibody methodologies e.g., the standard somatic cell hybridization technique of Kohler and Milstein, *Nature* (1975) 256: 495, as discussed above. The antibodies or nucleic acids encoding for the antibodies may be sequenced using any standard DNA or protein sequencing techniques.

In some embodiments, the cell-surface lineage-specific antigen that is targeted using the methods and cells described herein is a cell-surface lineage-specific antigen of leukocytes or a subpopulation of leukocytes. In some embodiments, the cell-surface lineage-specific antigen is an antigen that is associated with myeloid cells. In some embodiments, the cell-surface lineage-specific antigen is a cluster of differentiation antigens (CDs). Examples of CD antigens include, without limitation, CD1a, CD1b, CD1c, CD1d, CD1e, CD2, CD3, CD3d, CD3e, CD3g, CD4, CD5S, CD6, CD7, CD8a, CD8b, CD9, CD10, CD11a, CD11b, CD11c, CD1d, CDw12, CD13, CD14, CD15, CD16, CD16b, CD17, CD18, CD19, CD20, CD21, CD22, CD23, CD24, CD25, CD26, CD27, CD28, CD29, CD30, CD31, CD32a, CD32b, CD32c, CD33, CD34, CD35, CD36, CD37, CD38, CD39, CD40, CD41, CD42a, CD42b, CD42c, CD42d, CD43, CD44, CD45, CD45RA, CD45RB, CD45RC, CD45RO, CD46, CD47, CD48, CD49a, CD49b, CD49c, CD49d, CD49e, CD49f, CD50, CD51, CD52, CD53, CD54, CD5, CD56, CD57, CD58, CD59, CD60a, CD61, CD62E, CD62L, CD62P, CD63, CD64a, CD65, CD65s, CD66a, CD66b, CD66c, CD66F, CD68, CD69, CD70, CD71, CD72, CD73, CD74, CD75, CD75S, CD77, CD79a, CD79b, CD80, CD81, CD82, CD83, CD84, CD85A, CD85C, CD85D, CD85E, CD85F, CD85G, CD85H, CD85I, CD85J, CD85K, CD86, CD87, CD88, CD59, CD90, CD91, CD92, CD93, CD94, CD95, CD96, CD97, CD98, CD99, CD99R, CD100, CD101, CD102, CD103, CD104, CD105, CD106, CD107a, CD107b, CD108, CD109, CD110, CD111, CD112, CD113, CD114, CD115, CD11.6, CD117, CD118, CD119, CD120a, CD120b, CD121a, CD121b, CD121a, CD121b, CD122, CD123, CD124, CD125, CD126, CD127, CD129, CD130, CD1131, CD132, CD133, CD134, CD135, CD136, CD137, CD138, CD139, CD140a, CD140b, CD141, CD142, CD143, CD144, CDw145, CD146, CD147, CD148, CD150, CD152, CD152, CD153, CD154, CD155, CD156a, CD156b, CD156c, CD157, CD158b1, CD158b2, CD158d, CD158e1/e2, CD158f, CD158g, CD158h, CD158i, CD158j, CD158k, CD159a, CD159c, CD160, CD161, CD163, CD164, CD165, CD166, CD167a, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD194, CD195, CD196, CD197, CDw198, CDw199, CD200, CD201, CD202b, CD203c, CD204, CD205, CD206, CD207, CD208, CD209, CD210a, CDw210b, CD212, CD213a1, CD213a2, CD215, CD217, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240, CD241, CD242, CD243, CD244, CD24S, CD246, CD247, CD248, CD249, CD252, CD253, CD254, CD256, CD257, CD258, CD261I, CD262, CD263, CD264, CD265, CD266, CD267, CD268, CD269, CD270, CD271, CD272, CD273, CD274, CD275. CD276, CD277, CD278, CD279, CD280, CD281, CD282, CD283, CD284, CD286, CD288, CD289, CD290, CD292, CDw293, CD294, CD295, CD296, CD297, CD298, CD299, CD300a, CD300c, CD300e, CD301, CD302, CD303, CD304, CD305, 306, CD307a, CD307b, CD307c, D307d, CD307e, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD35K, CD359, CD360, CD361, CD362 and CD363. See www.bdbiosciences.com/documents/BD_Reagents_CDMarkerHuman_Poster.pdf.

In some embodiments, the cell-surface lineage-specific antigen is CD19, CD20, CD11, CD123, CD56, CD34, CD14, CD33, CD66b, CD41, CD61, CD62, CD23Sa, CD146, CD326, LMP2, CD22, CD52, CD10, CD3/TCR, CD79/BCR, and CD26. In some embodiments, the cell-surface lineage-specific antigen is CD33 or CD19.

Alternatively or in addition, the cell-surface lineage-specific antigen may be a cancer antigen, for example a cell-surface lineage-specific antigen that is differentially present on cancer cells. In some embodiments, the cancer antigen is an antigen that is specific to a tissue or cell lineage. Examples of cell-surface lineage-specific antigen that are associated with a specific type of cancer include, without limitation, CD20, CD22 (Non-Hodgkin's lymphoma. B-cell lymphoma, chronic lymphocytic leukemia (CLL)), CD52 (B-cell CLL), CD33 (Acute myelogenous leukemia (AML)), CD10 (gp100) (Common (pre-B) acute lymphocytic leukemia and malignant melanoma), CD3/T-cell receptor (TCR) (T-cell lymphoma and leukemia), CD79/B-cell receptor (BCR) (B-cell lymphoma and leukemia), CD26 (epithelial and lymphoid malignancies), human leukocyte antigen (HLA)-DR, HLA-DP, and HLA-DQ (lymphoid malignancies), RCAS1 (gynecological carcinomas, biliary adenocarcinomas and ductal adenocarcinomas of the pancreas) as well as prostate specific membrane antigen. In some embodiments, the cell-surface antigen CD33 and is associated with AML cells.

B. Antigen-Binding Fragment

Any antibody or an antigen-binding fragment thereof can be used for constructing the agent that targets a lineage-specific cell-surface antigen as described herein. Such an antibody or antigen-binding fragment can be prepared by a conventional method, for example, the hybridoma technology or recombinant technology.

For example, antibodies specific to a lineage-specific antigen of interest can be made by the conventional hybridoma technology. The lineage-specific antigen, which may be coupled to a carrier protein such as KLH, can be used to immunize a host animal for generating antibodies binding to that complex. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., in Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the TCR-like monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of binding to a lineage-specific antigen. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the lineage-specific antigen. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and. Alternatively, the phage display technology (McCafferty et al., (1990) Nature 348: 552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81,6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA., 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704, 692) can be adapted to produce a phage or yeast scFv library and scFv clones specific to a lineage-specific antigen can be identified from the library following routine procedures. Positive clones can be subjected to further screening to identify those that bind lineage-specific antigen.

In some instances, lineage-specific antigen of interest is CD33 and the antigen-binding fragment specifically binds CD33, for example, human CD33. Amino acid and nucleic acid sequences of an exemplary heavy chain variable region and light chain variable region of an anti-human CD33 antibody are provided below. The CDR sequences are shown Amino acid sequence of anti-CD33 Heavy Chain
Variable Region
(SEQ ID NO: 12)
QVQLQQPGAEVVKPGASVKMSCKASGYTFTSYYIHWIKQTPGQGLEWV

GVIYPGNDDISYNQKFQGKATLTADKSSTTAYMQLSSLTSEDSAVYYC

AREVRLRYFDVWGQGTTVTVSS

Nucleic acid sequence of anti-CD33 Heavy Chain
Variable Region
(SEQ ID NO: 2)
CAGGTGCAGCTGCAGCAGCCCGGCGCCGAGGTGGTGAAGCCCGGCGCC

AGCGTGAAGATGAGCTGCAAGGCCAGCGGCTACACCTTCACCAGCTAC

TACATCCACTGGATCAAGCAGACCCCCGGCCAGGGCCTGGAGTGGGTG

GGCGTGATCTACCCCGGCAACGACGACATCAGCTACAACCAGAAGTTC

CAGGGCAAGGCCACCCTGACCGCCGACAAGAGCAGCACCACCGCCTAC

ATGCAGCTGAGCAGCCTGACCAGCGAGGACAGCGCCGTGTACTACTGC

GCCAGGGAGGTGAGGCTGAGGTACTTCGACGTGTGGGGCCAGGGCACC

ACCGTGACCGTGAGCAGC

-continued

Amino acid sequence of anti-CD33 Light Chain
Variable Region (SEQ ID NO: 13)
EIVLTQSPGSLAVSPGERVTMSCKSSQSVFFSSSQKNYLAWYQQIPGQ

SPRLLIYWASTRESGVPDRFTGSGSGTDFTLTISSVQPEDLAIYYCHQ

YLSSRTFGQGTKLEIKR

Nucleic acid sequence of anti-CD33 Heavy Chain
Variable Region (SEQ ID NO: 1)
GAGATCGTGCTGACCCAGAGCCCCGGCAGCCTGGCCGTGAGCCCCGGC

GAGAGGGTGACCATGAGCTGCAAGAGCAGCCAGAGCGTGTTCTTCAGC

AGCAGCCAGAAGAACTACCTGGCCTGGTACCAGCAGATCCCCGGCCAG

AGCCCCAGGCTGCTGATCTACTGGGCCAGCACCAGGGAGAGCGGCGTG

CCCGACAGGTTCACCGGCAGCGGCAGCGGCACCGACTTCACCCTGACC

ATCAGCAGCGTGCAGCCCGAGGACCTGGCCATCTACTACTGCCACCAG

TACCTGAGCAGCAGGACCTTCGGCCAGGGCACCAAGCTGGAGATCAAG

AGG

The anti-CD33 antibody binding fragment for use in constructing the agent that targets CD33 as described herein may comprise the same heavy chain and/or light chain CDR regions as those in SEQ ID NO:12 and SEQ ID NO:13. Such antibodies may comprise amino acid residue variations in one or more of the framework regions. In some instances, the anti-CD33 antibody fragment may comprise a heavy chain variable region that shares at least 70% sequence identity (e.g., 75%, 80%, 85%, 90%, 95%, or higher) with SEQ ID NO: 12 and/or may comprise a light chain variable region that shares at least 70% sequence identity (e.g., 75%, 80%, 85%, 90%, 95%, or higher) with SEQ ID NO: 13.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. *J. Mol. Biol* 215:403-10, 1990. BLAST protein searches can be performed with the XBLAST program, score=50, word-length=3 to obtain amino acid sequences homologous to the protein molecules of the present disclosure. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

C. Immune Cells Expressing Chimeric Receptors

In some embodiments, the agent that targets a lineage-specific cell-surface antigen as described herein is an immune cell that expresses a chimeric receptor, which comprises an antigen-binding fragment (e.g., a single-chain antibody) capable of binding to the lineage-specific antigen (e.g., CD33 or CD19). Recognition of a target cell (e.g., a cancer cell) having the lineage-specific antigen on its cell surface by the antigen-binding fragment of the chimeric receptor transduces an activation signal to the signaling domain(s) (e.g., co-stimulatory signaling domain and/or the cytoplasmic signaling domain) of the chimeric receptor, which may activate an effector function in the immune cell expressing the chimeric receptor.

As used herein, a chimeric receptor refers to a non-naturally occurring molecule that can be expressed on the surface of a host cell and comprises an antigen-binding fragment that binds to a cell-surface lineage-specific antigen. In general, chimeric receptors comprise at least two domains that are derived from different molecules. In addition to the antigen-binding fragment described herein, the chimeric receptor may further comprise one or more of a hinge domain, a transmembrane domain, at least one co-stimulatory domain, and a cytoplasmic signaling domain. In some embodiments, the chimeric receptor comprises from N terminus to C terminus, an antigen-binding fragment that binds to a cell-surface lineage-specific antigen, a hinge domain, a transmembrane domain, and a cytoplasmic signaling domain. In some embodiments, the chimeric receptor further comprises at least one co-stimulatory domain.

In some embodiments, the chimeric receptors described herein comprise a hinge domain, which may be located between the antigen-binding fragment and a transmembrane domain. A hinge domain is an amino acid segment that is generally found between two domains of a protein and may allow for flexibility of the protein and movement of one or both of the domains relative to one another. Any amino acid sequence that provides such flexibility and movement of the antigen-binding fragment relative to another domain of the chimeric receptor can be used.

The hinge domain may contain about 10-200 amino acids, e.g., 15-150 amino acids, 20-100 amino acids, or 30-60 amino acids. In some embodiments, the hinge domain may be of about 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is of CD8α or CD28α. In some embodiments, the hinge domain is a portion of the hinge domain of CD8α, e.g., a fragment containing at least 15 (e.g., 20, 25, 30, 35, or 40) consecutive amino acids of the hinge domain of CD8α or CD28 α.

Hinge domains of antibodies, such as an IgG, IgA, IgM, IgE, or IgD antibody, are also compatible for use in the chimeric receptors described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Also within the scope of the present disclosure are chimeric receptors comprising a hinge domain that is a non-naturally occurring peptide. In some embodiments, the hinge domain between the C-terminus of the extracellular ligand-binding domain of an Fc receptor and the N-terminus of the transmembrane domain is a peptide linker, such as a (GlyxSer)n linker, wherein x and n, independently can be an integer between 3 and 12, including 3, 4, 5, 6, 7, 8, 9, 10, 11, 12, or more.

Additional peptide linkers that may be used in a hinge domain of the chimeric receptors described herein are known in the art. See, e.g., Wriggers et al. *Curren Trends in Peptide Science* (2005) 80(6): 736-746 and PCT Publication WO 2012/088461.

In some embodiments, the chimeric receptors described herein may comprise a transmembrane domain. The transmembrane domain for use in the chimeric receptors can be in any form known in the art. As used herein, a "transmembrane domain" refers to any protein structure that is thermodynamically stable in a cell membrane, preferably a eukaryotic cell membrane. Transmembrane domains compatible for use in the chimeric receptors used herein may be obtained from a naturally occurring protein. Alternatively, the transmembrane domain may be a synthetic, non-naturally occurring protein segment, e.g., a hydrophobic protein segment that is thermodynamically stable in a cell membrane.

Transmembrane domains are classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, S, 6, 7 or more times). In some embodiments, the transmembrane domain is a single-pass transmembrane domain. In some embodiments, the transmembrane domain is a single-pass transmembrane domain that orients the N terminus of the chimeric receptor to the extracellular side of the cell and the C terminus of the chimeric receptor to the intracellular side of the cell. In some embodiments, the transmembrane domain is obtained from a single pass transmembrane protein. In some embodiments, the transmembrane domain is of CD8α. In some embodiments, the transmembrane domain is of CD28. In some embodiments, the transmembrane domain is of ICOS.

In some embodiments, the chimeric receptors described herein comprise one or more costimulatory signaling domains. The term "co-stimulatory signaling domain," as used herein, refers to at least a portion of a protein that mediates signal transduction within a cell to induce an immune response, such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils.

In some embodiments, the chimeric receptor comprises more than one (at least 2, 3, 4, or more) co-stimulatory signaling domains. In some embodiments, the chimeric receptor comprises more than one co-stimulatory signaling domains obtained from different costimulatory proteins. In some embodiments, the chimeric receptor does not comprise a co-stimulatory signaling domain.

In general, many immune cells require co-stimulation, in addition to stimulation of an antigen-specific signal, to promote cell proliferation, differentiation and survival, and to activate effector functions of the cell. Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory protein may be compatible for use in the chimeric receptors described herein. The type(s) of co-stimulatory signaling domain is selected based on factors such as the type of the immune cells in which the chimeric receptors would be expressed (e.g., primary T cells, T cell lines, NK cell lines) and the desired immune effector function (e.g., cytotoxicity). Examples of co-stimulatory signaling domains for use in the chimeric receptors can be the cytoplasmic signaling domain of co-stimulatory proteins, including, without limitation, CD27, CD28, 4-1BB, OX40, CD30, Cd40, PD-1, ICOS, lymphocyte function-associated antigen-1 (LFA-1), CD2, CD7, LIGHT, NKG2C, B7-H3. In some embodiments, the co-stimulatory domain is derived from 4-1BB, CD28, or ICOS. In some embodiments, the costimulatory domain is derived from CD28 and chimeric receptor comprises a second co-stimulatory domain from 4-1BB or ICOS.

In some embodiments, the costimulatory domain is a fusion domain comprising more than one costimulatory domain or portions of more than one costimulatory domains. In some embodiments, the costimulatory domain is a fusion of costimulatory domains from CD28 and ICOS.

In some embodiments, the chimeric receptors described herein comprise a cytoplasmic signaling domain. Any cytoplasmic signaling domain can be used in the chimeric receptors described herein. In general, a cytoplasmic signaling domain relays a signal, such as interaction of an extracellular ligand-binding domain with its ligand, to stimulate a cellular response, such as inducing an effector function of the cell (e.g., cytotoxicity).

As will be evident to one of ordinary skill in the art, a factor involved in T cell activation is the phosphorylation of immunoreceptor tyrosine-based activation motif (ITAM) of a cytoplasmic signaling domain. Any ITAM-containing domain known in the art may be used to construct the chimeric receptors described herein. In general, an ITAM motif may comprise two repeats of the amino acid sequence YxxL/I separated by 6-8 amino acids, wherein each x is independently any amino acid, producing the conserved motif YxxL/Ix(6-8)YxxL/I. In some embodiments, the cytoplasmic signaling domain is from CD3ζ.

Exemplary chimeric receptors are provided in Tables 2 and 3 below.

TABLE 2

Exemplary components of a chimeric receptor

| Chimeric receptor component | Amino acid sequence |
|---|---|
| Antigen-binding fragment | Light chain- GSTSSGSGKPGSGEGSTKG (SEQ ID NO: 14)-Heavy chain |

TABLE 2-continued

Exemplary components of a chimeric receptor

| Chimeric receptor component | Amino acid sequence |
| --- | --- |
| CD28 costimulatory domain | IEVMYPPPYLDNEKSNGTIIHVKGKHLCPSP LFPGPSKPFWVLVVVGGVLACYSLLVTVA FIIFWVRSKRSRLLHSDYMNMTPRRPGPTR KHYQPYAPPRDFAAYS (SEQ ID NO: 6) |
| ICOS costimulatory domain (boldface), ICOS transmembrane domain (italics) and a portion of the extracellular domain of ICOS (underlined) | LSIFDPPPFKVTLTGGYLHIYESQLCCQLKF *WLPIGCAAFVVVCILGCILI*CWLTKKKYSSS VHDPNGEYMFMRAVNTAKKSRLTDVTL (SEQ ID NO: 7) |
| ICOS costimulatory domain | CWLTKKKYSSSVHDPNGEYMFMRAVNTA KKSRLTDVTL (SEQ ID NO: 47) |
| CD28/ICOS chimera (the ICOS portion shown in underline) including the hinge domain (italics) and transmembrane domain (bold) from CD28 | *IEVMYPPPYLDNEKSNGTIIHVKGKHLCPSPL FPGPS*KPFWVLVVVGGVLACYSLLVTVA FIIFWVRSKRSRLLHSDYM_FMRAVNTAKK SRLTDVTL_ (SEQ ID NO: 8) |
| CD3ζ cytoplasmic signaling domain | RVKFSRSADAPAYQQGQNQLYNELNLGRR EEYDVLDKRRGRDPEMGGKPQRRKNPQE GLYNELQKDKMAEAYSEIGMKGERRRGK GHDGLYQGLSTATKDTYDALHMQALPPR (SEQ ID NO: 15) |

The nucleic acid sequence of exemplary components for construction of a chimeric receptor are provided below.

CD28 intracellular signaling domain-DNA-Human
(SEQ ID NO: 3)
ATTGAAGTTATGTATCCTCCTCCTTACCTAGACAATGAGAAGAGCAAT

GGAACCATTATCCATGTGAAAGGGAAACACCTTTGTCCAAGTCCCCTA

TTTCCCGGACCTTCTAAGCCCTTTTGGGTGCTGGTGGTGGTTGGTGGA

GTCCTGGCTTGCTATAGCTTGCTAGTAACAGTGGCCTTTATTATTTTC

TGGGTGAGGAGTAAGAGGAGCAGGCTCCTGCACAGTGACTACATGAAC

ATGACTCCCCGCCGCCCCGGGCCCACCCGCAAGCATTACCAGCCCTAT

GCCCCACCACGCGACTTCGCAGAACCAGCTCTATAACGAGCTCAATCT

AGGACGAAGAGAGGAGTACGATGTTTTGGACAAGAGACGTGGCCGGGA

CCCTGAGATGGGGGGAAAGCCGAGAAGGAAGAACCCTCAGGAAGGCCT

GTACAATGAACTGCAGAAAGATAAGATGGCGGAGGCCTACAGTGAGAT

TGGGATGAAAGGCGAGCGCCGGAGGGGCAAGGGGCACGATGGCCTTTA

CCAGGGTCTCAGTACAGCCACCAAGGACACCTACGACGCCCTTCACAT

GCAGGCCCTGCCCCCTCGC

ICOS intracellular signaling domain-DNA-Human
(SEQ ID NO: 4)
CTATCAATTTTTGATCCTCCTCCTTTTAAAGTAACTCTTACAGGAGGA

TATTTGCATATTTATGAATCACAACTTTGTTGCCAGCTGAAGTTCTGG

TTACCCATAGGATGTGCAGCCTTTGTTGTAGTCTGCATTTTGGGATGC

ATACTTATTTGTTGGCTTACAAAAAAGAAGTATTCATCCAGTGTGCAC

GACCCTAACGGTGAATACATGTTCATGAGAGCAGTGAACACAGCCAAA

AAATCTAGACTCACAGATGTGACCCTAAGAGTGAAGTTCAGCAGGAGC

GCAGACGCCCCCGCGTACCAGCAGGGCCAGAACCAGCTCTATAACGAG

CTCAATCTAGGACGAAGAGAGGAGTACGATGTTTTGGACAAGAGACGT

GGCCGGGACCCTGAGATGGGGGGAAAGCCGAGAAGGAAGAACCCTCAG

GAAGGCCTGTACAATGAACTGCAGAAAGATAAGATGGCGGAGGCCTAC

AGTGAGATTGGGATGAAAGGCGAGCGCCGGAGGGGCAAGGGGCACGAT

GGCCTTTACCAGGGTCTCAGTACAGCCACCAAGGACACCTACGACGCC

CTTCACATGCAGGCCCTGCCCCCTCGC

CD28/ICOS COSTIMULATORY SIGNALING REGION-DNA-Human
(SEQ ID NO: 5)
ATTGAAGTTATGTATCCTCCTCCTTACCTAGACAATGAGAAGAGCAAT

GGAACCATTATCCATGTGAAAGGGAAACACCTTTGTCCAAGTCCCCTA

TTTCCCGGACCTTCTAAGCCCTTTTGGGTGCTGGTGGTGGTTGGTGGA

GTCCTGGCTTGCTATAGCTTGCTAGTAACAGTGGCCTTTATTATTTTC

TGGGTGAGGAGTAAGAGGAGCAGGCTCCTGCACAGTGACTACATGTTC

ATGAGAGCAGTGAACACAGCCAAAAAATCTAGACTCACAGATGTGACC

CTAAGAGTGAAGTTCAGCAGGAGCGCAGACGCCCCCGCGTACCAGCAG

GGCCAGAACCAGCTCTATAACGAGCTCAATCTAGGACGAAGAGAGGAG

TACGATGTTTTGGACAAGAGACGTGGCCGGGACCCTGAGATGGGGGGA

AAGCCGAGAAGGAAGAACCCTCAGGAAGGCCTGTACAATGAACTGCAG

AAAGATAAGATGGCGGAGGCCTACAGTGAGATTGGGATGAAAGGCGAG

CGCCGGAGGGGCAAGGGGCACGATGGCCTTTACCAGGGTCTCAGTACA

GCCACCAAGGACACCTACGACGCCCTTCACATGCAGGCCCTGCCCCCT

CGC

In some embodiments, the nucleic acid sequence encodes an antigen binding fragment that binds to CD33 and comprises a heavy chain variable region which has the same CDRs as the CDRs in SEQ ID NO. 12 and a light chain variable region which has the same CDRs as the CDRs in SEQ ID NO: 13. In some embodiments, the antigen-binding fragment comprises a heavy chain variable region as provided by SEQ ID NO: 12 and a light chain variable region as provided by SEQ ID NO: 13. In some embodiments, the chimeric receptor further comprises at least a transmembrane domain and a cytoplasmic signaling domain. In some embodiments, the chimeric receptor further comprises a hinge domain and/or a co-stimulatory signaling domain.

Table 3 provides exemplary chimeric receptors described herein. The exemplary constructs have from N-terminus to C-terminus, the antigen-binding fragment, the transmembrane domain, and a cytoplasmic signaling domain. In some examples, the chimeric receptor further comprises a hinge domain located between the antigen-binding fragment and the transmembrane domain. In some example, the chimeric receptor further comprises one or more co-stimulatory domains, which may be located between the transmembrane domain and the cytoplasmic signaling domain.

TABLE 3

Exemplary chimeric receptors

| Constructs | Vector | Antigen-binding fragment specificity | Hinge domain | Transmembrane domain | Signaling domain 1 | Signaling domain 2 | Signaling domain 3 |
|---|---|---|---|---|---|---|---|
| CART1 (SEQ ID NO: 20) | HIVzs-Gfp | CD33 | CD8α | CD8 | 4-1BB | CD3ζ | None |
| CART2 (SEQ ID NO: 21) | HIVzs-Gfp | CD33 | CD8α | CD28 | CD28 | CD3ζ | None |
| CART3 (SEQ ID NO: 22) | HIVzs-Gfp | CD33 | CD8α | CD28 | CD28 | 4-1BB | CD3 ζ |
| CART8 (SEQ ID NO: 23) | HIVzs-Gfp | CD33 | CD8α | ICOS | ICOS | 4-1BB | CD3 ζ |
| CART4dual (SEQ ID NO: 24) | HIVzs-dT | CD19 | CD8α | CD28 | CD3 ζ | — | — |
| CART5dual (SEQ ID NO: 25) | HIVzs-Gfp | CD33 | CD8α | CD28 | CD28 | — | — |
| CART6 (SEQ ID NO: 26) | HIVzs-dT | CD19 | CD8α | CD28 | CD28 | CD3 ζ | — |
| CART7 (SEQ ID NO: 27) | HIVzs-Gfp | CD33 | CD28hge | CD28 | CD28 | CD3 ζ | — |

Amino acid sequences of the example chimeric receptors listed in Table 3 above are provided below:

```
cart1 amino acid sequence
                                          (SEQ ID NO: 20)
MWLQSLLLLGTVACSISEIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYLSSRTFGQGTKLEIKRGS

TSGSGKPGSGEGSTKGQVQLQQPGAEVVKPGASVKMSCKASGYTFTSYYIHWIKQTPGQGLEWVGV

IYPGNDDISYNQKFQGKATLTADKSSTTAYMQLSSLTSEDSAVYYCAREVRLRYFDVWGQGTTVTV

SSALSNSIMYFSHFVPVFLPAKPTTTPAPRPPTPAPTIASQPLSLRPEASRPAAGGAVHTRGLDIY

IWAPLAGTCGVLLLSLVITKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAEAY

SEIGMKGERRRGKGHDGLYQGLSTATKDTYDALHMQALPPR

CART2 amino acid sequence
                                          (SEQ ID NO: 21)
MWLQSLLLLGTVACSISEIVLTQSPGLSAVSPGERVTMSCKSSQSVFFSSSQKNYLAWYQQIPGQS

PRLLIYWASTRESGVPDRFTGSGSGTDFTLTISSVQPEDLAIYYCHQYLSSRTFGQGTKLEIKRGS

TSGSGKPGSGEGSTKGQVQLQQPGAEVVKPGASVKMSCKASGYTFTSYYIHWIKQTPGQGLEWVGV

IYPGNDDISYNQKFQGKATLTADKSSTTAYMQLSSLTSEDSAVYYCAREVRLRYFDVWGQGTTVTV

SALSNSIMYFSHFVPVFLPAKPTTTPAPRPPTPAPTIASQPLSLRPEASRPAAGGAVHTRGLDKPF

WVLVVVGGVLACYSLLVTVAFIIFWVRSKRSRLLHSDYMNMTPRRPGPTRKHYQPYAPPRDFAAYR

SRVKFSRSADAPAYQQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR
```

CART3 amino acid sequence
(SEQ ID NO: 22)
MWLQSLLLLGTVACSISEIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYLSSRTFGQGTKLEIKRGS

TSGSGKPGSGEGSTKGQVQLQQPGAEVVKPGASVKMSCKASGYTFTSYYIHWIKQTPGQGLEWVGV

IYPGNDDISYNQKFQGKATLTADKSSTTAYMQLSSLTSEDSAVYYCAREVRLRTFDVWGQGTTVTV

SSALSNSIMYFSHFVPVFLPAKPTTTPAPRPPTPAPTIASQPLSLRPEASRPAAGGAVHTRGLDKP

FWVLVVVGGVLACYSLLVTVAFIIFWVRSKRSRLLHSDYMNMTPRRPGPTRKHYQPYAPPRDFAAY

RSKRGRKKLLYIFKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIGMKGERRRGKGHDG

LYQGLSTATKDTYDALHMQALPPR

CART8 amino acid sequence
(SEQ ID NO: 23)
MWLQSLLLLGTVACSISEIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYLSSRTFGQGTKLEIKRGS

TSGSGKPGSGEGSTKGQVQLQQPGAEVVKPGASVKMSCKASGYTFTSYYIHWIKQTPGQGLEWVGV

IYPGNDDISYNQKFQGKATLTADKSSTTAYMQLSSLTSEDSAVYYCAREVRLRYFDVWGQGTTVTV

SSALSNSIMYFSHFVPVFLPAKPTTTPAPRPPTPAPTIASQPLSLRPEASRPAAGGAVHTRGLDFW

LPIGCAAFVVVCILGCILICWLTKKKYSSSVHDPNGEYMFMRAVNTAKKSRLTDVTLTKRGRKKLL

YIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATK

DTYDALHMQALPPR

CART4dual amino acid sequence
(SEQ ID NO: 24)
MWLQSLLLLGTVACSISIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGGGTKLEIGSTSGSGKPG

SGEGSTKGLQESGPGLVAPSQSLSVTCTVSGVSLPDYGVSWIRQPPRKGLEWLGVIWGSETTYYNS

ALKSRLTIIKDNSKSQVFLKMNSLQTDDTAIYYCAKHYYYGGSYAMDYWGQGTSVTVSALSNSIMY

FSHFVPVFLPAKPTTTPAPRPPTPAPTIASQPLSLRPEASRPAAGGAVHTRGLDKPFWVLVVVGGV

LACYSLLVTVAFIIFWVRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQALPPR

CART5dual amino acid sequence
(SEQ ID NO: 25)
MWLQSLLLLGTVACSISEIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYLSSRTFGQGTKLEIKRGS

TSGSGKPGSGEGSTKGQVQLQQPGAEVVKPGASVKMSCKASGYTFTSYYIHWIKQTPGQGLEWVGV

IYPGNDDISYNQKFQGKATLTADKSSTTAYMQLSSLTSEDSAVYYCAREVRLRYFDVWGQGTTVTV

SSALSNSIMYFSHFVPVFLPAKPTTTPAPRPPTPAPTIASQPLSLRPEASRPAAGGAVHTRGLDKP

FWVLVVVGGVLACYSLLVTVAFIIFWVRSKRSRLLHSDYMNMTPRRPGPTRKHYQPYAPPRDFAAY

RS

CART6 amino acid sequence
(SEQ ID NO: 26)
MWLQSLLLLGTVACSISIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGGGTKLEIGSTSGSGKPG

SGEGSTKGLQESGPGLVAPSQSLSVTCTVSGVSLPDYGVSWIRQPPRKGLEWLGVIWGSETTYYNS

ALKSRLTIIKDNSKSQVFLKMNSLQTDDTAIYYCAKHYYYGGSYAMDYWGQGTSVTVSALSNSIMY

-continued

FSHFVPVFLPAKPTTTPAPRPPTPAPTIASQPLSLRPEASRPAAGGAVHTRGLDKPFWVLVVVGGV
LACYSLLVTVAFIIFWVRSKRSRLLHSDYMNMTPRRPGPTRKHYQPYAPPRDFAAYRSRVKFSRSA
DAPAYQQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

CART7 amino acid sequence
(SEQ ID NO: 27)
MWLQSLLLLGTVACSISEIVLTQSPGLSAVSPGERVTMSCKSSQSVFFSSSQKNYLAWYQQIPGQS
PRLLIYWASTRESGVPDRFTGSGSGTDFTLTISSVQPEDLAIYYCHQYLSSRTFGQGTKLEIKRGS
TSGSGKPGSGEGSTKGQVQLQQPGAEVVKPGASVKMSCKASGYTFTSYYIHWIKQTPGQGLEWVGV
IYPGNDDISYNQKFQGKATLTADKSSTTAYMQLSSLTSEDSAVYYCAREVRLRYFDVWGQGTTVTV
SSIEVMYPPPYLDNEKSNGTIIHVKGKHLCPSPLFPGPSKPFWVLVVVGGVLACYSLLVTVAFIIF
WVRSKRSRLLHSDYMNMTPRRPGPTRKHYQPYAPPRDFAAYRSRVKFSRSADAPAYQQGQNQLYNE
LNLGRREEYDVLDKRRGRDPEMGGKPRRKNPQEGLYNELQKDKMAEAYSEIGMGERRRGKGHDGLY
QGLSTATKDTYDALHMQALPPR Nucleic acid sequences of the example chimeric receptors listed in
Table 3 above are provided below:
CART1 nucleic acid sequence
(SEQ ID NO: 38)
GGTGTCGTGAGCGGCCGCTGAACTGGCCACCATGTGGCTGCAGTCTCTGCTGCTGCTGGGCACCGT
GGCCTGTAGCATCAGCGAGATCGTGCTGACCCAGAGCCCTGGCTCTCTGGCTGTGTCTCCTGGCGA
GCGCGTGACCATGAGCTGCAAGAGCAGCCAGAGCGTGTTCTTCAGCAGCTCCCAGAAGAACTACCT
GGCCTGGTATCAGCAGATCCCCGGCCAGAGCCCCAGACTGCTGATCTACTGGGCCAGCACCAGAGA
AAGCGGCGTGCCCGATAGATTCACCGGCAGCGGCTCTGGCACCGACTTCACCCTGACAATCAGCAG
CGTGCAGCCCGAGGACCTGGCCATCTACTACTGCCACCAGTACCTGAGCAGCCGGACCTTTGGCCA
GGGCACCAAGCTGGAAATCAAGCGGGGCAGCACAAGCGGCAGCGGAAAGCCTGGATCTGGCGAGGG
CTCTACCAAGGGCCAGGTGCAGCTGCAGCAGCCTGGCGCCGAAGTCGTGAAACCTGGCGCCTCCGT
GAAGATGTCCTGCAAGGCCAGCGGCTACACCTTCACCAGCTACTACATCCACTGGATCAAGCAGAC
CCCTGGACAGGGCCTGGAATGGGTGGGAGTGATCTACCCCGGCAACGACGACATCAGCTACAACCA
GAAGTTCCAGGGCAAGGCCACCCTGACCGCCGACAAGTCTAGCACCACCGCCTACATGCAGCTGTC
CAGCCTGACCAGCGAGGACAGCGCCGTGTACTACTGCGCCAGAGAAGTGCGGCTGCGGTACTTCGA
TGTGTGGGGCCAGGGAACCACCGTGACCGTGTCTAGCGCCCTGAGCAACAGCATCATGTACTTCAG
CCACTTCGTGCCCGTGTTTCTGCCCGCCAAGCCTACCACAACCCCTGCCCCTAGACCTCCTACCCC
AGCCCCTACAATCGCCAGCCAGCCTCTGTCTCTGAGGCCCGAGGCTTCTAGACCAGCTGCTGGCGG
AGCCGTGCACACCAGAGGCCTGGATATCTACATCTGGGCCCCACTGGCCGGCACCTGTGGCGTGCT
GCTGCTGTCTCTCGTGATCACCAAGAGAGGCCGGAAGAAGCTGCTGTACATCTTCAAGCAGCCCTT
CATGCGGCCCGTGCAGACCACCCAGGAAGAGGACGGCTGTAGCTGCCGGTTCCCCGAGGAAGAAGA
AGGGGGCTGCGAGCTGAGAGTGAAGTTCAGCAGAAGCGCCGACGCCCCTGCCTATCAGCAGGGCCA
GAACCAGCTGTACAACGAGCTGAACCTGGGCAGACGGGAAGAGTACGACGTGCTGGACAAGCGGAG
AGGCAGGGACCCTGAGATGGGCGGCAAGCCCAGACGGAAGAACCCTCAGGAAGGCCTGTATAACGA
ACTGCAGAAAGACAAGATGGCCGAGGCCTACTCCGAGATCGGAATGAAGGGCGAGCGGAGAAGAGG
CAAGGGCCACGATGGACTGTACCAGGGCCTGAGCACCGCCACCAAGGACACCTATGACGCCCTGCA
CATGCAGGCCCTGCCCCCCAGATGAAATTCATCGACGTTAACTATTCTAG -continued CART2 nucleic acid sequence (SEQ ID NO: 39)
GGTGTCGTGAGCGGCCGCTGAACTGGCCACCATGTGGCTGCAGTCTCTGCTGCTGCTGGGCACCGT

GGCCTGTAGCATCAGCGAGATCGTGCTGACCCAGAGCCCTGGCTCTCTGGCTGTGTCTCCTGGCGA

GCGCGTGACCATGAGCTGCAAGAGCAGCCAGAGCGTGTTCTTCAGCAGCTCCCAGAAGAACTACCT

GGCCTGGTATCAGCAGATCCCCGGCCAGAGCCCCAGACTGCTGATCTACTGGGCCAGCACCAGAGA

AAGCGGCGTGCCCGATAGATTCACCGGCAGCGGCTCTGGCACCGACTTCACCCTGACAATCAGCAG

CGTGCAGCCCGAGGACCTGGCCATCTACTACTGCCACCAGTACCTGAGCAGCCGGACCTTTGGCCA

GGGCACCAAGCTGGAAATCAAGCGGGGCAGCACAAGCGGCAGCGGAAAGCCTGGATCTGGCGAGGG

CTCTACCAAGGGCCAGGTGCAGCTGCAGCAGCCTGGCGCCGAAGTCGTGAAACCTGGCGCCTCCGT

GAAGATGTCCTGCAAGGCCAGCGGCTACACCTTCACCAGCTACTACATCCACTGGATCAAGCAGAC

CCCTGGACAGGGCCTGGAATGGGTGGGAGTGATCTACCCCGGCAACGACGACATCAGCTACAACCA

GAAGTTCCAGGGCAAGGCCACCCTGACCGCCGACAAGTCTAGCACCACCGCCTACATGCAGCTGTC

CAGCCTGACCAGCGAGGACAGCGCCGTGTACTACTGCGCCAGAGAAGTGCGGCTGCGGTACTTCGA

TGTGTGGGGCCAGGGAACCACCGTGACCGTGTCTGCCCTGAGCAACAGCATCATGTACTTCAGCCA

CTTCGTGCCCGTGTTTCTGCCCGCCAAGCCTACCACAACCCCTGCCCCTAGACCTCCTACCCCAGC

CCCTACAATCGCCAGCCAGCCTCTGTCTCTGAGGCCCGAGGCTTCTAGACCAGCTGCTGGCGGAGC

CGTGCACACCAGAGGACTGGACAAGCCCTTCTGGGTGCTGGTGGTCGTGGGCGGAGTGCTGGCCTG

TTACAGCCTGCTCGTGACAGTGGCCTTCATCATCTTTTGGGTGCGCAGCAAGCGGTATAGACTGCT

GCACAGCGACTACATGAACATGACCCCCAGAAGGCCAGGCCCCACCCGGAAGCACTATCAGCCTTA

CGCCCCTCCCAGAGACTTCGCCGCCTACCGGTCCAGAGTGAAGTTCAGCAGAAGCGCCGACGCCCC

TGCCTATCAGCAGGGCCAGAACCAGCTGTACAACGAGCTGAACCTGGGCAGACGGGAAGAGTACGA

CGTGCTGGACAAGAGAAGAGGCCGGGACCCTGAGATGGGCGGCAAGCCCAGACGGAAGAACCCTCA

GGAAGGCCTGTATAACGAACTGCAGAAAGACAAGATGGCCGAGGCCTACTCCGAGATCGGCATGAA

GGGCGAACGGCGGAGAGGCAAGGGACACGATGGACTGTACCAGGGCCTGAGCACCGCCACCAAGGA

CACCTATGACGCCCTGCACATGCAGGCCCTGCCCCCCAGATGAAATTCATCGACGTTAACTATTCT

AG

CART3 nucleic acid sequeuce (SEQ ID NO: 40)
GGTGTCGTGAGCGGCCGCTGAACTGGCCACCATGTGGCTGCAGTCTCTGCTGCTGCTGGGCACCGT

GGCCTGCAGCATCAGCATCCAGATGACCCAGACCACCAGCAGCCTGAGCGCCAGCCTGGGCGATAG

AGTGACCATCAGCTGCAGAGCCAGCCAGGACATCAGCAAGTACCTGAACTGGTATCAGCAGAAACC

CGACGGCACCGTGAAGCTGCTGATCTACCACACCAGCAGACTGCACAGCGGCGTGCCCTCTAGATT

TTCCGGCAGCGGCTCCGGCACCGACTACAGCCTGACCATCTCCAACCTGGAACAGGAAGATATCGC

TACCTACTTCTGTCAGCAAGGCAACACCCTGCCCTACACCTTCGGCGGAGGCACCAAGCTGGAAAT

CGGCAGCACAAGCGGCTCTGGCAAGCCTGGATCTGGCGAGGGCTCTACCAAGGGCCTGCAGGAATC

TGGCCCTGGACTGGTGGCCCCTAGCCAGAGCCTGTCTGTGACCTGTACCGTGTCCGGCGTGTCCCT

GCCTGACTATGGCGTGTCCTGGATCAGACAGCCCCCCAGAAAGGGCCTGGAATGGCTGGGAGTGAT

CTGGGGCAGCGAGACAACCTACTACAACAGAGCCCTGAAGTCCCGGCTGACCATCATCAAGGACAA

CTCCAAGAGCCAGGTGTTCCTGAAGATGAACAGCCTGCAGACCGACGACACCGCCATCTACTACTG

CGCCAAGCACTACTACTACGGCGGCAGCTACGCCATGGACTACTGGGGCCAGGGCACAAGCGTGAC

CGTGTCTGCCCTGAGCAACAGCATCATGTACTTCAGCCACTTCGTGCCCGTGTTTCTGCCCGCCAA

GCCTACCACAACCCCTGCCCCTAGACCTCCTACCCCAGCCCCTACAATCGCCAGCCAGCCTCTGTC

TCTGAGGCCCGAGGCTTCTAGACCAGCTGCTGGCGGAGCCGTGCACACCAGAGGACTGGACAAGCC

CTTCTGGGTGCTGGTGGTCGTGGGCGGAGTGCTGGCCTGTTATAGCCTGCTCGTGACAGTGGCCTT

CATCATCTTTTGGGTGCGCGTGAAGTTCAGCCGCAGCGCCGATGCCCCTGCCTATCAGCAGGGACA

GAACCAGCTGTACAACGAGCTGAACCTGGGCAGACGGGAAGAGTACGACGTGCTGGACAAGAGAAG

AGGCCGGGACCCTGAGATGGGCGGCAAGCCCAGAAGAAAGAACCCCCAGGAAGGCCTGTATAACGA

ACTGCAGAAAGACAAGATGGCCGAGGCCTACAGCGAGATCGGCATGAAGGGCGAACGGCGGAGAGG

CAAGGGCCACGATGGACTGTATCAGGGCCTGAGCACCGCCACCAAGGACACCTATGACGCCCTGCA

CATGCAGGCTCTGCCCCCTCGCTGAAATTCATCGACGTTAACTATTCTAG

CART4dual nucleic acid sequence
(SEQ ID NO: 41)
GGTGTCGTGAGCGGCCGCTGAACTGGCCACCATGTGGCTGCAGTCTCTGCTGCTGCTGGGCACCGT

GGCCTGCAGCATCAGCATCCAGATGACCCAGACCACCAGCAGCCTGAGCGCCAGCCTGGGCGATAG

AGTGACCATCAGCTGCAGAGCCAGCCAGGACATCAGCAAGTACCTGAACTGGTATCAGCAGAAACC

CGACGGCACCGTGAAGCTGCTGATCTACCACACCAGCAGACTGCACAGCGGCGTGCCCTCTAGATT

TTCCGGCAGCGGCTCCGGCACCGACTACAGCCTGACCATCTCCAACCTGGAACAGGAAGATATCGC

TACCTACTTCTGTCAGCAAGGCAACACCCTGCCCTACACCTTCGGCGGAGGCACCAAGCTGGAAAT

CGGCAGCACAAGCGGCTCTGGCAAGCCTGGATCTGGCGAGGGCTCTACCAAGGGCCTGCAGGAATC

TGGCCCTGGACTGGTGGCCCCTAGCCAGAGCCTGTCTGTGACCTGTACCGTGTCCGGCGTGTCCCT

GCCTGACTATGGCGTGTCCTGGATCAGACAGCCCCCAGAAAGGGCCTGGAATGGCTGGGAGTGAT

CTGGGGCAGCGACACAACCTACTACAACAGCGCCCTGAAGTCCCGGCTGACCATCATCAAGGACAA

CTCCAAGAGCCAGGTGTTCCTGAAGATGAACAGCCTGCAGACCGACGACACCGCCATCTACTACTG

CGCCAAGCACTACTACTACGGCGGCAGCTACGCCATGGACTACTGGGGCCAGGGCACAAGCGTGAC

CGTGTCTGCCCTGAGCAACAGCATCATGTACTTCAGCCACTTCGTGCCCGTGTTTCTGCCCGCCAA

GCCTACCACAACCCCTGCCCCTAGACCTCCTACCCCAGCCCCTACAATCGCCAGCCAGCCTCTGTC

TCTGAGGCCCGAGGCTTCTAGACCAGCTGCTGGCGGAGCCGTGCACACCAGAGGACTGGACAAGCC

CTTCTGGGTGCTGGTGGTCGTGGGCGGAGTGCTGGCCTGTTATAGCCTGCTCGTGACAGTGGCCTT

CATCATCTTTTGGGTGCGCGTGAAGTTCAGCCGCAGCGCCGATGCCCCTGCCTATCAGCAGGGACA

GAACCAGCTGTACAACGAGCTGAACCTGGGCAGACGGGAAGAGTACGACGTGCTGGACAAGAGAAG

AGGCCGGGACCCTGAGATGGGCGGCAAGCCCAGAAGAAAGAACCCCCAGGAAGGCCTGTATAACGA

ACTGCAGAAAGACAAGATGGCCGAGGCCTACAGCGAGATCGGCATGAAGGGCGAACGGCGGAGAGG

CAAGGGCCACGATGGACTGTATCAGGGCCTGAGCACCGCCACCAAGGACACCTATGACGCCCTGCA

CATGCAGGCTCTGCCCCCTCGCTGAAATTCATCGACGTTAACTATTCTAG

CART5dual nucleic acid sequence
(SEQ ID NO: 42)
GGTGTCGTGAGCGGCCGCTGAACTGGCCACCATGTGGCTGCAGTCTCTGCTGCTGCTGGGCACCGT

GGCCTGTAGCATCAGCGAGATCGTGCTGACCCAGAGCCCTGGCTCTCTGGCTGTGTCTCCGGGCGA

GCGCGTGACCATGAGCTGCAAGAGCAGCCAGAGCGTGTTCTTCAGCAGCTCCCAGAAGAACTACCT

GGCCTGGTATCAGCAGATCCCCGGCCAGAGCCCCAGACTGCTGATCTACTGGGCCAGCACCAGAGA

AAGCGGCGTGCCCGATAGATTCACCGGCAGCGGCTCTGGCACCGACTTCACCCTGACAATCAGCAG

CGTGCAGCCCGAGGACCTGGCCATCTACTACTGCCACCAGTACCTGAGCAGCCGGACCTTTGGCCA

GGGCACCAAGCTGGAAATCAAGCGGGGCAGCACAAGCGGCAGCGGAAAGCCTGGATCTGGCGAGGG

CTCTACCAAGGGCCAGGTGCAGCTGCAGCAGCCTGGCGCCGAAGTCGTGAAACCTGGCGCCTCCGT

-continued

GAAGATGTCCTGCAAGGCCAGCGGCTACACCTTCACCAGCTACTACATCCACTGGATCAAGCAGAC

CCCTGGACAGGGCCTGGAATGGGTGGGAGTGATCTACCCCGGCAACGACGACATCAGCTACAACCA

GAAGTTCCAGGGCAAGGCCACCCTGACCGCCGACAAGTCTAGCACCACCGCCTACATGCAGCTGTC

CAGCCTGACCAGCGAGGACAGCGCCGTGTACTACTGCGCCAGAGAAGTGCGGCTGCGGTACTTCGA

TGTGTGGGGCCAGGGAACCACCGTGACCGTGTCTAGCGCCCTGAGCAACAGCATCATGTACTTCAG

CCACTTCGTGCCCGTGTTTCTGCCCGCCAAGCCTACCACAACCCCTGCCCCTAGACCTCCTACCCC

AGCCCCTACAATCGCCAGCCAGCCTCTGTCTCTGAGGCCCGAGGCTTCTAGACCAGCTGCTGGCGG

AGCCGTGCACACCAGAGGACTGGACAAGCCCTTCTGGGTGCTGGTGGTCGTGGGCGGAGTGCTGGC

CTGTTACAGCCTGCTCGTGACAGTGGCCTTCATCATCTTTTGGGTGCGCAGCAAGCGGTCTAGACT

GCTGCACAGCGACTACATGAACATGACCCCCAGAAGGCCAGGCCCCACCCGGAAGCACTATCAGCC

TTACGCCCCTCCCAGAGACTTCGCCGCCTACAGAAGCTGAAATTCATCGACGTTAACTATTCTAG

CART6 nucleic acid sequence (SEQ ID NO: 43)

GGTGTCGTGAGCGGCCGCTGAACTGGCCACCATGTGGCTGCAGTCTCTGCTGCTGCTGGGCACCGT

GGCCTGCAGCATCAGCATCCAGATGACCCAGACCACCAGCAGCCTGAGCGCCAGCCTGGGCGATAG

AGTGACCATCAGCTGCAGAGCCAGCCAGGACATCAGCAAGTACCTGAACTGGTATCAGCAGAAACC

CGACGGCACCGTGAAGCTGCTGATCTACCACACCAGCAGACTGCACAGCGGCGTGCCCTCTAGATT

TTCCGGCAGCGGCTCCGGCACCGACTACAGCCTGACCATCTCCAACCTGGAACAGGAAGATATCGC

TACCTACTTCTGTCAGCAAGGCAACACCCTGCCCTACACCTTCGGCGGAGGCACCAAGCTGGAAAT

CGGCAGCACAAGCGGCTCTGGCAAGCCTGGATCTGGCGAGGGCTCTACCAAGGGCCTGCAGGAATC

TGGCCCTGGACTGGTGGCCCCTAGCCAGAGCCTGTCTGTGACCTGTACCGTGTCCGGCGTGTCCCT

GCCTGACTATGGCGTGTCCTGGATCAGACAGCCCCCAGAAAGGGCCTGGAATGGCTGGGAGTGAT

CTGGGGCAGCGAGACAACCTACTACAACAGCGCCCTGAAGTCCCGGCTGACCATCATCAAGGACAA

CTCCAAGAGCCAGGTGTTCCTGAAGATGAACAGCCTGCAGACCGACGACACCGCCATCTACTACTG

CGCCAAGCACTACTACTACGGCGGCAGCTACGCCATGGACTACTGGGGCCAGGGCACAAGCGTGAC

CGTGTCTGCCCTGAGCAACAGCATCATGTACTTCAGCCACTTCGTGCCCGTGTTTCTGCCCGCCAA

GCCTACCACAACCCCTGCCCCTAGACCTCCTACCCCAGCCCCTACAATCGCCAGCCAGCCTCTGTC

TCTGAGGCCCGAGGCTTCTAGACCAGCTGCTGGCGGAGCCGTGCACACCAGAGGACTGGACAAGCC

CTTCTGGGTGCTGGTGGTCGTGGGCGGAGTGCTGGCCTGTTATAGCCTGCTCGTGACAGTGGCCTT

CATCATCTTTTGGGTGCGCAGCAAGCGGAGCCGGCTGCTGCACTCCGACTACATGAACATGACCCC

CAGACGGCCAGGCCCCACCCGGAAACACTATCAGCCTTACGCCCCTCCCAGAGACTTCGCCGCCTA

CCGGTCCAGAGTGAAGTTCAGCAGATCCGCCGACGCCCCTGCCTATCAGCAGGGACAGAACCAGCT

GTACAACGAGCTGAACCTGGGCAGACGGGAAGAGTACGACGTGCTGGACAAGAGAAGAGGCCGGGA

CCCTGAGATGGCGGCAAGCCCAGAAGAAAGAACCCCAGGAAGGCCTGTATAACGAACTGCAGAA

AGACAAGATGGCCGAGGCCTACAGCGAGATCGGCATGAAGGGCGAACGGCGGAGAGGCAAGGGCCA

CGATGGACTGTATCAGGGCCTGAGCACCGCCACCAAGGACACCTATGACGCCCTGCACATGCAGGC

TCTGCCCCTCGCTGAAATTCATCGACGTTAACTATTCTAG

CART7 nucleic acid sequence (SEQ ID NO: 44)

GGTGTCGTGAGCGGCCGCTGAACTGGCCACCATGTGGCTGCAGTCTCTGCTGCTGCTGGGCACCGT

GGCCTGTAGCATCAGCGAGATCGTGCTGACCCAGAGCCCTGGCTCTCTGGCTGTGTCTCCGGGCGA

GCGCGTGACCATGAGCTGCAAGAGCAGCCAGAGCGTGTTCTTCAGCAGCTCCCAGAAGAACTACCT

GGCCTGGTATCAGCAGATCCCCGGCCAGAGCCCCAGACTGCTGATCTACTGGGCCAGCACCAGAGA

-continued

```
AAGCGGCGTGCCCGATAGATTCACCGGCAGCGGCTCTGGCACCGACTTCACCCTGACAATCAGCAG

CGTGCAGCCCGAGGACCTGGCCATCTACTACTGCCACCAGTACCTGAGCAGCCGGACCTTTGGCCA

GGGCACCAAGCTGGAAATCAAGCGGGGCAGCACAAGCGGCAGCGGAAAGCCTGGATCTGGCGAGGG

CTCTACCAAGGGCCAGGTGCAGCTGCAGCAGCCTGGCGCCGAAGTCGTGAAACCTGGCGCCTCCGT

GAAGATGTCCTGCAAGGCCAGCGGCTACACCTTCACCAGCTACTACATCCACTGGATCAAGCAGAC

CCCTGGACAGGGCCTGGAATGGGTGGGAGTGATCTACCCCGGCAACGACGACATCAGCTACAACCA

GAAGTTCCAGGGCAAGGCCACCCTGACCGCCGACAAGTCTAGCACCACCGCCTACATGCAGCTGTC

CAGCCTGACCAGCGAGGACAGCGCCGTGTACTACTGCGCCAGAGAAGTGCGGCTGCGGTACTTCGA

TGTGTGGGGCCAGGGAACCACCGTGACCGTGTCCAGCATCGAAGTGATGTACCCCCCTCCCTACCT

GGACAACGAGAAGTCCAACGGCACCATCATCCACGTGAAGGGCAAGCACCTGTGCCCCAGCCCTCT

GTTTCCTGGCCCTAGCAAGCCCTTCTGGGTGCTGGTGGTCGTGGGCGGAGTGCTGGCCTGTTACAG

CCTGCTCGTGACAGTGGCCTTCATCATCTTTTGGGTGCGCAGCAAGCGGTCTAGACTGCTGCACAG

CGACTACATGAACATGACCCCCAGAAGGCCAGGCCCCACCCGGAAGCACTATCAGCCTTACGCCCC

TCCCAGAGACTTCGCCGCCTACCGGTCCAGAGTGAAGTTCAGCAGAAGCGCCGACGCCCCTGCCTA

TCAGCAGGGCCAGAACCAGCTGTACAACGAGCTGAACCTGGGCAGACGGGAAGAGTACGACGTGCT

GGACAAGCGGAGAGGCAGGGACCCTGAGATGGGCGGCAAGCCCAGACGGAAGAACCCTCAGGAAGG

CCTGTATAACGAACTGCAGAAAGACAAGATGGCCGAGGCCTACTCCGAGATCGGCATGAAGGGCGA

GCGGAGAAGAGGCAAGGGCCACGATGGACTGTACCAGGGCCTGAGCACCGCCACCAAGGACACCTA

TGACGCCCTGCACATGCAGGCCCTGCCCCCCAGATGAAATTCATCGACGTTAACTATTCTAG
```

Any of the chimeric receptors described herein can be prepared by routine methods, such as recombinant technology. Methods for preparing the chimeric receptors herein involve generation of a nucleic acid that encodes a polypeptide comprising each of the domains of the chimeric receptors, including the antigen-binding fragment and optionally, the hinge domain, the transmembrane domain, at least one co-stimulatory signaling domain, and the cytoplasmic signaling domain. In some embodiments, a nucleic acid encoding each of the components of chimeric receptor are joined together using recombinant technology.

Sequences of each of the components of the chimeric receptors may be obtained via routine technology, e.g., PCR amplification from any one of a variety of sources known in the art. In some embodiments, sequences of one or more of the components of the chimeric receptors are obtained from a human cell. Alternatively, the sequences of one or more components of the chimeric receptors can be synthesized. Sequences of each of the components (e.g., domains) can be joined directly or indirectly (e.g., using a nucleic acid sequence encoding a peptide linker) to form a nucleic acid sequence encoding the chimeric receptor, using methods such as PCR amplification or ligation. Alternatively, the nucleic acid encoding the chimeric receptor may be synthesized. In some embodiments, the nucleic acid is DNA. In other embodiments, the nucleic acid is RNA.

Mutation of one or more residues within one or more of the components of the chimeric receptor (e.g., the antigen-binding fragment, etc), prior to or after joining the sequences of each of the components. In some embodiments, one or more mutations in a component of the chimeric receptor may be made to modulate (increase or decrease) the affinity of the component for a target (e.g., the antigen-binding fragment for the target antigen) and/or modulate the activity of the component.

Any of the chimeric receptors described herein can be introduced into a suitable immune cell for expression via conventional technology. In some embodiments, the immune cells are T cells, such as primary T cells or T cell lines. Alternatively, the immune cells can be NK cells, such as established NK cell lines (e.g., NK-92 cells). In some embodiments, the immune cells are T cells that express CD8 ($CD8^+$) or CD8 and CD4 ($CD8^+/CD4^+$). In some embodiments, the T cells are T cells of an established T cell line, for example, 293T cells or Jurkat cells.

Primary T cells may be obtained from any source, such as peripheral blood mononuclear cells (PBMCs), bone marrow, tissues such as spleen, lymph node, thymus, or tumor tissue. A source suitable for obtaining the type of immune cells desired would be evident to one of skill in the art. In some embodiments, the population of immune cells is derived from a human patient having a hematopoietic malignancy, such as from the bone marrow or from PBMCs obtained from the patient. In some embodiments, the population of immune cells is derived from a healthy donor. In some embodiments, the immune cells are obtained from the subject to whom the immune cells expressing the chimeric receptors will be subsequently administered. Immune cells that are administered to the same subject from which the cells were obtained are referred to as autologous cells, whereas immune cells that are obtained from a subject who is not the subject to whom the cells will be administered are referred to as allogeneic cells.

The type of host cells desired may be expanded within the population of cells obtained by co-incubating the cells with stimulatory molecules, for example, anti-CD3 and anti-CD28 antibodies may be used for expansion of T cells.

To construct the immune cells that express any of the chimeric receptor constructs described herein, expression vectors for stable or transient expression of the chimeric receptor construct may be constructed via conventional methods as described herein and introduced into immune host cells. For example, nucleic acids encoding the chimeric receptors may be cloned into a suitable expression vector, such as a viral vector in operable linkage to a suitable promoter. The nucleic acids and the vector may be contacted, under suitable conditions, with a restriction enzyme to create complementary ends on each molecule that can pair with each other and be joined with a ligase. Alternatively, synthetic nucleic acid linkers can be ligated to the termini of the nucleic acid encoding the chimeric receptors. The synthetic linkers may contain nucleic acid sequences that correspond to a particular restriction site in the vector. The selection of expression vectors/plasmids/viral vectors would depend on the type of host cells for expression of the chimeric receptors, but should be suitable for integration and replication in eukaryotic cells.

A variety of promoters can be used for expression of the chimeric receptors described herein, including, without limitation, cytomegalovirus (CMV) intermediate early promoter, a viral LTR such as the Rous sarcoma virus LTR, HIV-LTR, HTLV-I LTR, Maloney murine leukemia virus (MMLV) LTR, myeoloproliferative sarcoma virus (MPSV) LTR, spleen focus-forming virus (SFFV) LTR, the simian virus 40 (SV40) early promoter, herpes simplex tk virus promoter, elongation factor 1-alpha (EF1-α) promoter with or without the EF1-α intron. Additional promoters for expression of the chimeric receptors include any constitutively active promoter in an immune cell. Alternatively, any regulatable promoter may be used, such that its expression can be modulated within an immune cell.

Additionally, the vector may contain, for example, some or all of the following: a selectable marker gene, such as the neomycin gene for selection of stable or transient transfectants in host cells; enhancer/promoter sequences from the immediate early gene of human CMV for high levels of transcription; transcription termination and RNA processing signals from SV40 for mRNA stability; 5'- and 3'-untranslated regions for mRNA stability and translation efficiency from highly-expressed genes like α-globin or β-globin; SV40 polyoma origins of replication and ColE1 for proper episomal replication: internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase, an inducible caspase such as iCasp9), and reporter gene for assessing expression of the chimeric receptor. See section VI below. Suitable vectors and methods for producing vectors containing transgenes are well known and available in the an. Examples of the preparation of vectors for expression of chimeric receptors can be found, for example, in US2014/0106449, herein incorporated by reference in its entirety.

In some embodiments, the chimeric receptor construct or the nucleic acid encoding said chimeric receptor is a DNA molecule. In some embodiments, chimeric receptor construct or the nucleic acid encoding said chimeric receptor is a DNA vector and may be electroporated to immune cells (see, e.g., Till, et al. Blood (2012) 119(17): 3940-3950). In some embodiments, the nucleic acid encoding the chimeric receptor is an RNA molecule, which may be electroporated to immune cells.

Any of the vectors comprising a nucleic acid sequence that encodes a chimeric receptor construct described herein is also within the scope of the present disclosure. Such a vector may be delivered into host cells such as host immune cells by a suitable method. Methods of delivering vectors to immune cells are well known in the art and may include DNA, RNA, or transposon electroporation, transfection reagents such as liposomes or nanoparticles to delivery DNA, RNA, or transposons; delivery of DNA, RNA, or transposons or protein by mechanical deformation (see, e.g., Sharei et al. *Proc. Natl. Acad. Sci. U(SA* (2013) 110(6); 2082-2087); or viral transduction. In some embodiments, the vectors for expression of the chimeric receptors are delivered to host cells by viral transduction. Exemplary viral methods for delivery include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769: WO 93/19191; WO 94/28938; WO 95/11984 and WO 95/00655). In some embodiments, the vectors for expression of the chimeric receptors are retroviruses. In some embodiments, the vectors for expression of the chimeric receptors are lentiviruses. In some embodiments, the vectors for expression of the chimeric receptors are adeno-associated viruses.

In examples in which the vectors encoding chimeric receptors are introduced to the host cells using a viral vector, viral particles that are capable of infecting the immune cells and carry the vector may be produced by any method known in the art and can be found, for example in PCT Application No. WO 1991/002805A2, WO 1998/009271 A1, and U.S. Pat. No. 6,194,191. The viral particles are harvested from the cell culture supernatant and may be isolated and/or purified prior to contacting the viral particles with the immune cells.

The methods of preparing host cells expressing any of the chimeric receptors described herein may comprise activating and/or expanding the immune cells er vivo. Activating a host cell means stimulating a host cell into an activate state in which the cell may be able to perform effector functions (e.g., cytotoxicity). Methods of activating a host cell will depend on the type of host cell used for expression of the chimeric receptors. Expanding host cells may involve any method that results in an increase in the number of cells expressing chimeric receptors, for example, allowing the host cells to proliferate or stimulating the host cells to proliferate. Methods for stimulating expansion of host cells will depend on the type of host cell used for expression of the chimeric receptors and will be evident to one of skill in the art. In some embodiments, the host cells expressing any of the chimeric receptors described herein are activated and/or expanded ex vivo prior to administration to a subject.

In some embodiments, the agents targeting a cell-surface lineage-specific antigen is an antibody-drug conjugate (ADC). As will be evident to one of ordinary skill in the art, the term "antibody-drug conjugate" can be used interchangeably with "immunotoxin" and refers to a fusion molecule comprising an antibody (or antigen-binding fragment thereof) conjugated to a toxin or drug molecule. Binding of the antibody to the corresponding antigen allows for delivery of the toxin or drug molecule to a cell that presents the antigen on the its cell surface (e.g., target cell), thereby resulting in death of the target cell.

In some embodiments, the agent is an antibody-drug conjugate. In some embodiments, the antibody-drug conjugate comprises an antigen-binding fragment and a toxin or drug that induces cytotoxicity in a target cell. In some embodiments, the antibody-drug conjugate targets a type 2 antigen. In some embodiments, the antibody-drug conjugate targets CD33 or CD19.

In some embodiments, the antigen-bind fragment of the antibody-drug conjugate has the same heavy chain CDRs as the heavy chain variable region provided by SEQ ID NO: 12 and the same light chain CDRS as the light chain variable region provided by SEQ ID NO: 13. In some embodiments, the antigen-bind fragment of the antibody-drug conjugate has the heavy chain variable region provided by SEQ ID NO: 12 and the same light chain variable region provided by SEQ ID NO: 13.

Toxins or drugs compatible for use in antibody-drug conjugate are well known in the art and will be evident to one of ordinary skill in the art. See, e.g., Peters et al. *Biosci. Rep.* (2015) 35(4): e00225. In some embodiments, the antibody-drug conjugate may further comprise a linker (e.g., a peptide linker, such as a cleavable linker) attaching the antibody and drug molecule.

An ADC described herein may be used as a follow-on treatment to subjects who have been undergone the combined therapy as described herein.

Hematopoietic Cells Deficient in a Lineage-Specific Cell-Surface Antigen

The present disclosure also provides hematopoietic cells such as HSCs that have been genetically modified to be deficient in a lineage-specific cell-surface antigen. In some embodiments, the hematopoietic cells are hematopoietic stem cells. Hematopoietic stem cells (HSCs) are capable of giving rise to both myeloid and lymphoid progenitor cells that further give rise to myeloid cells (e.g., monocytes, macrophages, neutrophils, basophils, dendritic cells, erythrocytes, platelets, etc) and lymphoid cells (e.g., T cells, B cells, NK cells), respectively. HSCs are characterized by the expression of the cell surface marker CD34 (e.g., CD34+), which can be used for the identification and/or isolation of HSCs, and absence of cell surface markers associated with commitment to a cell lineage.

In some embodiments, the HSCs are obtained from a subject, such as a mammalian subject. In some embodiments, the mammalian subject is a non-human primate, a rodent (e.g., mouse or rat), a bovine, a porcine, an equine, or a domestic animal. In some embodiments, the HSCs are obtained from a human patient, such as a human patient having a hematopoietic malignancy. In some embodiments, the HSCs are obtained from a healthy donor. In some embodiments, the HSCs are obtained from the subject to whom the immune cells expressing the chimeric receptors will be subsequently administered. HSCs that are administered to the same subject from which the cells were obtained are referred to as autologous cells, whereas HSCs that are obtained from a subject who is not the subject to whom the cells will be administered are referred to as allogeneic cells.

HSCs may be obtained from any suitable source using convention means known in the art. In some embodiments, HSCs are obtained from a sample from a subject, such as bone marrow sample or from a blood sample. Alternatively or in addition, HSCs may be obtained from an umbilical cord. In some embodiments, the HSCs are from bone marrow or peripheral blood mononuclear cells (PBMCs). In general, bone marrow cells may be obtained from iliac crest, femora, tibiae, spine, rib or other medullary spaces of a subject. Bone marrow may be taken out of the patient and isolated through various separations and washing procedures known in the art. An exemplary procedure for isolation of bone marrow cells comprises the following steps: a) extraction of a bone marrow sample; b) centrifugal separation of bone marrow suspension in three fractions and collecting the intermediate fraction, or buffycoat: c) the buffycoat fraction from step (b) is centrifuged one more time in a separation fluid, commonly Ficoll™, and an intermediate fraction which contains the bone marrow cells is collected; and d) washing of the collected fraction from step (c) for recovery of re-transfusable bone marrow cells.

HSCs typically reside in the bone marrow but can be mobilized into the circulating blood by administering a mobilizing agent in order to harvest HSCs from the peripheral blood. In some embodiments, the subject from which the HSCs are obtained is administered a mobilizing agent, such as granulocyte colony-stimulating factor (G-CSF). The number of the HSCs collected following mobilization using a mobilizing agent is typically greater than the number of cells obtained without use of a mobilizing agent.

In some embodiments, a sample is obtained from a subject and is then enriched for a desired cell type (e.g. $CD34^+$/$CD33^-$ cells). For example, PBMCs and/or $CD34^+$ hematopoietic cells can be isolated from blood as described herein. Cells can also be isolated from other cells, for example by isolation and/or activation with an antibody binding to an epitope on the cell surface of the desired cell type. Another method that can be used includes negative selection using antibodies to cell surface markers to selectively enrich for a specific cell type without activating the cell by receptor engagement.

Populations of HSC can be expanded prior to or after genetically engineering the HSC to become deficient in a lineage specific cell-surface antigen. The cells may be cultured under conditions that comprise an expansion medium comprising one or more cytokines, such as stem cell factor (SCF), Flt-3 ligand (Flt3L), thrombopoietin (TPO), Interleukin 3 (IL-3), or Interleukin 6 (IL-6). The cell may be expanded for about 1, 2, 3, 4, 5, 6, 7, 8, 9, 10, 11, 12, 13, 14, 15, 16, 17, 18, 19, 20, 21, 22, 23, 24, 25 days or any range necessary. In some embodiments, the HSC are expanded after isolation of a desired cell population (e.g., $CD34^+$/$CD33^-$) from a sample obtained from a subject and prior to genetic engineering. In some embodiments, the HSC are expanded after genetic engineering, thereby selectively expanding cells that have undergone the genetic modification and are deficient in a lineage-specific cell-surface antigen. In some embodiments, a cell ("a clone") or several cells having a desired characteristic (e.g., phenotype or genotype) following genetic modification may be selected and independently expanded.

In some embodiments, the hematopoietic cells are genetically engineered to be deficient in a cell-surface lineage-specific antigen. In some embodiments, the hematopoietic cells are genetically engineered to be deficient in the same cell-surface lineage-specific antigen that is targeted by the agent. As used herein, a hematopoietic cell is considered to be deficient in a cell-surface lineage-specific antigen if hematopoietic cell has substantially reduced expression of the cell-surface lineage-specific antigen as compared to a naturally-occurring hematopoietic cell of the same type as the genetically engineered hematopoietic cell (e.g., is characterized by the presence of the same cell surface markers, such as CD34). In some embodiments, the hematopoietic cell has no detectable expression of the cell-surface lineage-specific antigen. The expression level of a cell-surface lineage-specific antigen can be assessed by any means known in the art. For example, the expression level of a cell-surface lineage-specific antigen can be assessed by detecting the antigen with an antigen-specific antibody (e.g., flow cytometry methods, Western blotting).

In some embodiments, the expression of the cell-surface lineage-specific antigen on the genetically engineered hematopoietic cell is compared to the expression of the cell-surface lineage-specific antigen on a naturally occurring hematopoietic cell. In some embodiments, the genetic engineering results in a reduction in the expression level of the cell-surface lineage-specific antigen by at least about 50%, 60%, 70%, 80%, 90%, 91%, 92%, 93%, 94%, 95%, 96%, 97%, 98%, or 99% as compared to the expression of the cell-surface lineage-specific antigen on a naturally occurring hematopoietic cell.

In some embodiments, the hematopoietic cell is deficient in the whole endogenous gene encoding the cell-surface lineage-specific antigen. In some embodiments, the whole endogenous gene encoding the cell-surface lineage-specific antigen has been deleted. In some embodiments, the hematopoietic cell comprises a portion of endogenous gene encoding the cell-surface lineage-specific antigen. In some embodiments, the hematopoietic cell expressing a portion (e.g. a truncated protein) of the cell-surface lineage-specific antigen. In other embodiments, a portion of the endogenous gene encoding the cell-surface lineage-specific antigen has been deleted. In some embodiments, at least 10%, 20%, 30%, 40%, 50%, 60%, 70% or more of the gene encoding the cell-surface lineage-specific antigen has been deleted.

As will be appreciated by one of ordinary skill in the art, a portion of the nucleotide sequence encoding the cell-surface lineage-specific antigen may be deleted or one or more non-coding sequences, such that the hematopoietic cell is deficient in the antigen (e.g., has substantially reduced expression of the antigen).

In some embodiments, the cell-surface lineage-specific antigen is CD33. The predicted structure of CD33 includes two immunoglobulin domains, an IgV domain and an IgC2 domain. In some embodiments, a portion of the immunoglobulin C domain of CD33 is deleted.

Any of the genetically engineering hematopoietic cells, such as HSCs, that are deficient in a cell-surface lineage-specific antigen can be prepared by a routine method or by a method described herein. In some embodiments, the genetic engineering is performed using genome editing. As used herein. "genome editing" refers to a method of modifying the genome, including any protein-coding or non-coding nucleotide sequence, of an organism to knock out the expression of a target gene. In general, genome editing methods involve use of an endonuclease that is capable of cleaving the nucleic acid of the genome, for example at a targeted nucleotide sequence. Repair of the double-stranded breaks in the genome may be repaired introducing mutations and/or exogenous nucleic acid may be inserted into the targeted site.

Genome editing methods are generally classified based on the type of endonuclease that is involved in generating double stranded breaks in the target nucleic acid. These methods include use of zinc finger nucleases (ZFN), transcription activator-like effector-based nuclease (TALEN), meganucleases, and CRISPR/Cas systems.

Figure 4:
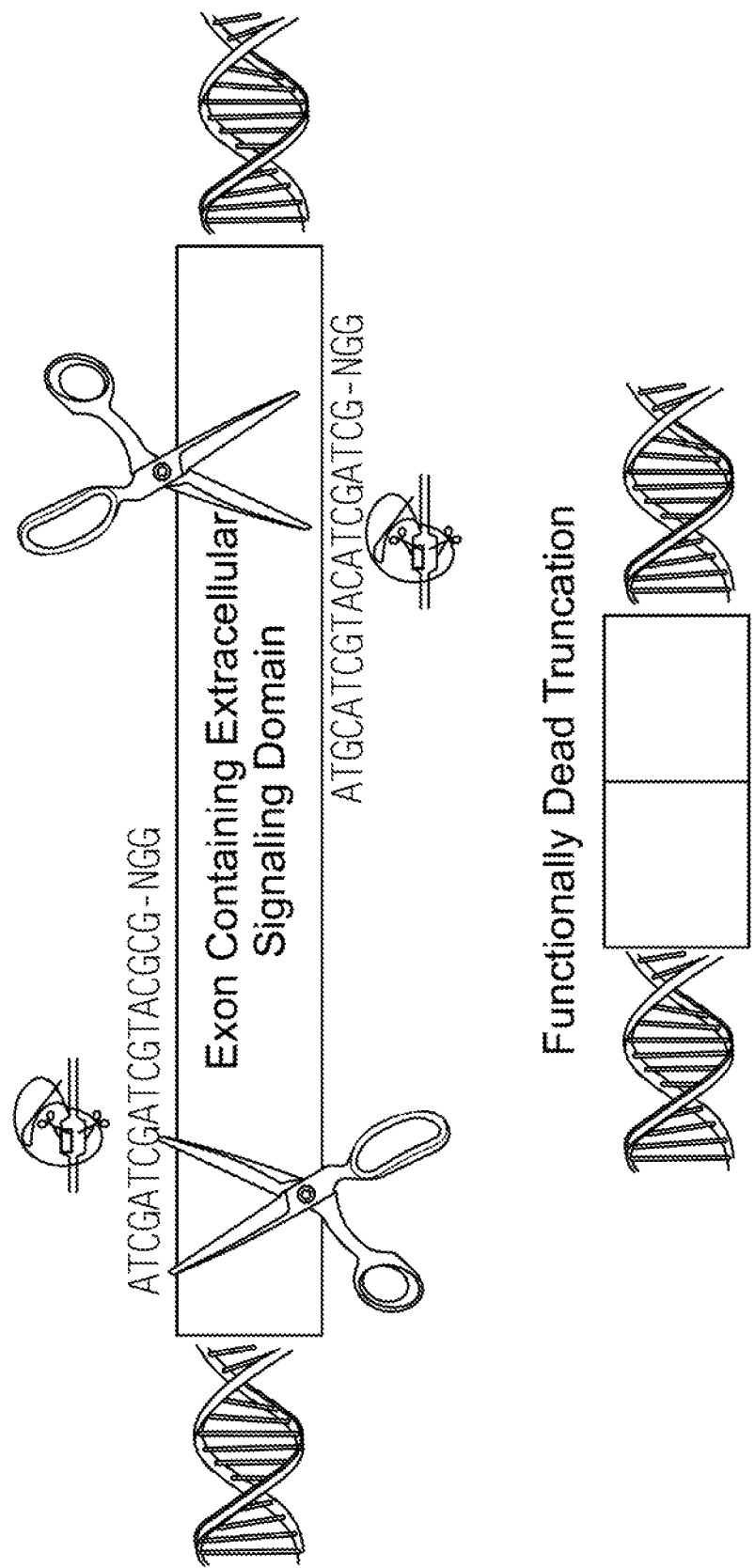
FIG. 4 is a schematic showing genome editing using a CRISPR/Cas system. A sgRNA hybridizes to a portion of an exon of a lineage-specific cell-surface antigen, and the Cas9 endonuclease cleaves upstream of the Protospacer Adjacent Motif (PAM) Sequence (5'-NGG-3'). The sequences, from top to bottom, correspond to SEQ ID NOs: 45 and 46.

In one aspect of the present disclosure, the replacement of the tumor cells by a modified population of normal cells is performed using normal cells in which a lineage-specific antigen is modified. Such modification may include the depletion or inhibition of any lineage specific antigen using a CRISPR-Cas9 system, where the Clustered Regularly Interspaced Short Palindromic Repeats (CRISPR)-Cas9 system is an engineered, non-naturally occurring CRISPR-Cas9 system (FIG. 4).

CRISPR-Cas system has been successfully utilized to edit the genomes of various organisms, including, but not limited to bacteria, humans, fruit flies, zebra fish and plants. See, e.g., Jiang et al., *Nature Bioiechnology* (2013) 31(3):233: Qi et al, *Cell* (2013) 5:1173; DiCarlo et al., *Nucleic Acids Res.* (2013) 7:4336; Hwang et al., *Nat. Biotechnol* (2013), 3:227); Gratz et al., *Genetics* (2013) 194:1029; Cong et al., *Science* (2013) 6121:819; Mali et al., *Science* (2013) 6121:823; Cho et al. *Nat. Biotechnol* (2013) 3: 230; and Jiang et al., *Nucleic Acids Research* (2013) 41(20):e188.

The present disclosure utilizes the CRISPR/Cas9 system that hybridizes with a target sequence in a lineage specific antigen polynucleotide, where the CRISPR/Cas9 system comprises a Cas9 nuclease and an engineered crRNA/tracrRNA (or single guide RNA). CRISPR/Cas9 complex can bind to the lineage specific antigen polynucleotide and allow the cleavage of the antigen polynucleotide, thereby modifying the polynucleotide.

The CRISPR/Cas system of the present disclosure may bind to and/or cleave the region of interest within a cell-surface lineage-specific antigen in a coding or non-coding region, within or adjacent to the gene, such as, for example, a leader sequence, trailer sequence or intron, or within a non-transcribed region, either upstream or downstream of the coding region. The guide RNAs (gRNAs) used in the present disclosure may be designed such that the gRNA directs binding of the Cas9-gRNA complexes to a predetermined cleavage sites (target site) in a genome. The cleavage sites may be chosen so as to release a fragment that contains a region of unknown sequence, or a region containing a SNP, nucleotide insertion, nucleotide deletion, rearrangement, etc.

Cleavage of a gene region may comprise cleaving one or two strands at the location of the target sequence by the Cas enzyme. In one embodiment, such, cleavage can result in decreased transcription of a target gene. In another embodiment, the cleavage can further comprise repairing the cleaved target polynucleotide by homologous recombination with an exogenous template polynucleotide, wherein the repair results in an insertion, deletion, or substitution of one or more nucleotides of the target polynucleotide.

The terms "gRNA," "guide RNA" and "CRISPR guide sequence" may be used interchangeably throughout and refer to a nucleic acid comprising a sequence that determines the specificity of a Cas DNA binding protein of a CRISPR/Cas system. A gRNA hybridizes to (complementary to, partially or completely) a target nucleic acid sequence in the genome of a host cell. The gRNA or portion thereof that hybridizes to the target nucleic acid may be between 15-25 nucleotides, 18-22 nucleotides, or 19-21 nucleotides in length. In some embodiments, the gRNA sequence that hybridizes to the target nucleic acid is 15, 16, 17, 18, 19, 20, 21, 22, 23, 24, or 25 nucleotides in length. In some embodiments, the gRNA sequence that hybridizes to the target nucleic acid is between 10-30, or between 15-25, nucleotides in length.

In addition to a sequence that binds to a target nucleic acid, in some embodiments, the gRNA also comprises a scaffold sequence. Expression of a gRNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gRNA may be referred to as a single guide RNA (sgRNA).

As used herein, a "scaffold sequence," also referred to as a tracrRNA, refers to a nucleic acid sequence that recruits a Cas endonuclease to a target nucleic acid bound (hybridized) to a complementary gRNA sequence. Any scaffold sequence that comprises at least one stem loop structure and recruits an endonuclease may be used in the genetic elements and vectors described herein. Exemplary scaffold sequences will be evident to one of skill in the art and can be found, for example, in Jinek, et al. Science (2012) 337(6096):816-821, Ran, et al. Nature Protocols (2013) 8:2281-2308, PCT Application No. WO2014/093694, and PCT Application No. WO2013/176772.

In some embodiments, the gRNA sequence does not comprises a scaffold sequence and a scaffold sequence is expressed as a separate transcript. In such embodiments, the gRNA sequence further comprises an additional sequence that is complementary to a portion of the scaffold sequence and functions to bind (hybridize) the scaffold sequence and recruit the endonuclease to the target nucleic acid.

In some embodiments, the gRNA sequence is at least 50%, 55%, 60%, 65%, 70%, 75%, 80%, 85%, 90%, 95%, 96%, 97%, 98%, 99%, or at least 100% complementary to a target nucleic acid (see also U.S. Pat. No. 8,697,359, which is incorporated by reference for its teaching of complementarity of a gRNA sequence with a target polynucleotide sequence). It has been demonstrated that mismatches between a CRISPR guide sequence and the target nucleic acid near the 3' end of the target nucleic acid may abolish nuclease cleavage activity (Upadhyay, et al. Genes Genome Genetics (2013) 3(12):2233-2238). In some embodiments, the gRNA sequence is at least 50%, 55%, 60%, 65%, 70%, 75%, 80%/o, 85%, 90%, 95%, 96%, 97%, 98%, 99%, or at least 100% complementary to the 3' end of the target nucleic acid (e.g., the last 5, 6, 7, 8, 9, or 10 nucleotides of the 3' end of the target nucleic acid).

The target nucleic acid is flanked on the 3' side by a protospacer adjacent motif (PAM) that may interact with the endonuclease and be further involved in targeting the endonuclease activity to the target nucleic acid. It is generally thought that the PAM sequence flanking the target nucleic acid depends on the endonuclease and the source from which the endonuclease is derived. For example, for Cas9 endonucleases that are derived from Streptococcus pyogenes, the PAM sequence is NGG. For Cas9 endonucleases derived from Staphylococcs aureus, the PAM sequence is NNGRRT. For Cas9 endonucleases that are derived from Netsseria meningitidis, the PAM sequence is NNNNGATT. For Cas9 endonucleases derived from Streptococcus thermophilus, the PAM sequence is NNAGAA. For Cas9 endonuclease derived from Treponema denticola, the PAM sequence is NAAAAC. For a Cpf1 nuclease, the PAM sequence is TTN.

In some embodiments, genetically engineering a cell also comprises introducing a Cas endonuclease into the cell. In some embodiments, the Cas endonuclease and the nucleic acid encoding the gRNA are provided on the same nucleic acid (e.g., a vector). In some embodiments, the Cas endonuclease and the nucleic acid encoding the gRNA are provided on different nucleic acids (e.g., different vectors). Alternatively or in addition, the Cas endonuclease may be provided or introduced into the cell in protein form.

In some embodiments, the Cas endonuclease is a Cas9 enzyme or variant thereof. In some embodiments, the Cas9 endonuclease is derived from Streptococcus pyrgenes, Staphylococcus aureus, Neisseria meninglitldis, Streptococcus thermophilus, or Treponema denticola. In some embodiments, the nucleotide sequence encoding the Cas endonuclease may be codon optimized for expression in a host cell. In some embodiments, the endonuclease is a Cas9 homolog or ortholog.

In some embodiments, the nucleotide sequence encoding the Cas9 endonuclease is further modified to alter the activity of the protein. In some embodiments, the Cas9 endonuclease is a catalytically inactive Cas9. For example, dCas9 contains mutations of catalytically active residues (D10 and H840) and does not have nuclease activity. Alternatively or in addition, the Cas9 endonuclease may be fused to another protein or portion thereof. In some embodiments, dCas9 is fused to a repressor domain, such as a KRAB domain. In some embodiments, such dCas9 fusion proteins are used with the constructs described herein for multiplexed gene repression (e.g. CRISPR interference (CRISPRi)). In some embodiments, dCas9 is fused to an activator domain, such as VP64 or VPR. In some embodiments, such dCas9 fusion proteins are used with the constructs described herein for gene activation (e.g., CRISPR activation (CRISPRa)). In some embodiments, dCas9 is fused to an epigenetic modulating domain, such as a histone demethylase domain or a histone acetyltransferase domain. In some embodiments, dCas9 is fused to a LSD1 or p300, or a portion thereof. In some embodiments, the dCas9 fusion is used for CRISPR-based epigenetic modulation. In some embodiments, dCas9 or Cas9 is fused to a Fok1 nuclease domain. In some embodiments, Cas9 or dCas9 fused to a Fok1 nuclease domain is used for genome editing. In some embodiments, Cas9 or dCas9 is fused to a fluorescent protein (e.g., GFP, RFP, mCherry, etc.). In some embodiments, Cas9/dCas9 proteins fused to fluorescent proteins are used for labeling and/or visualization of genomic loci or identifying cells expressing the Cas endonuclease.

Alternatively or in addition, the Cas endonuclease is a Cpf1 nuclease. In some embodiments, the host cell expresses a Cpf1 nuclease derived from Provetella spp. or Francsella spp. In some embodiments, the nucleotide sequence encoding the Cpf1 nuclease may be codon optimized for expression in a host cell.

Figure 5:
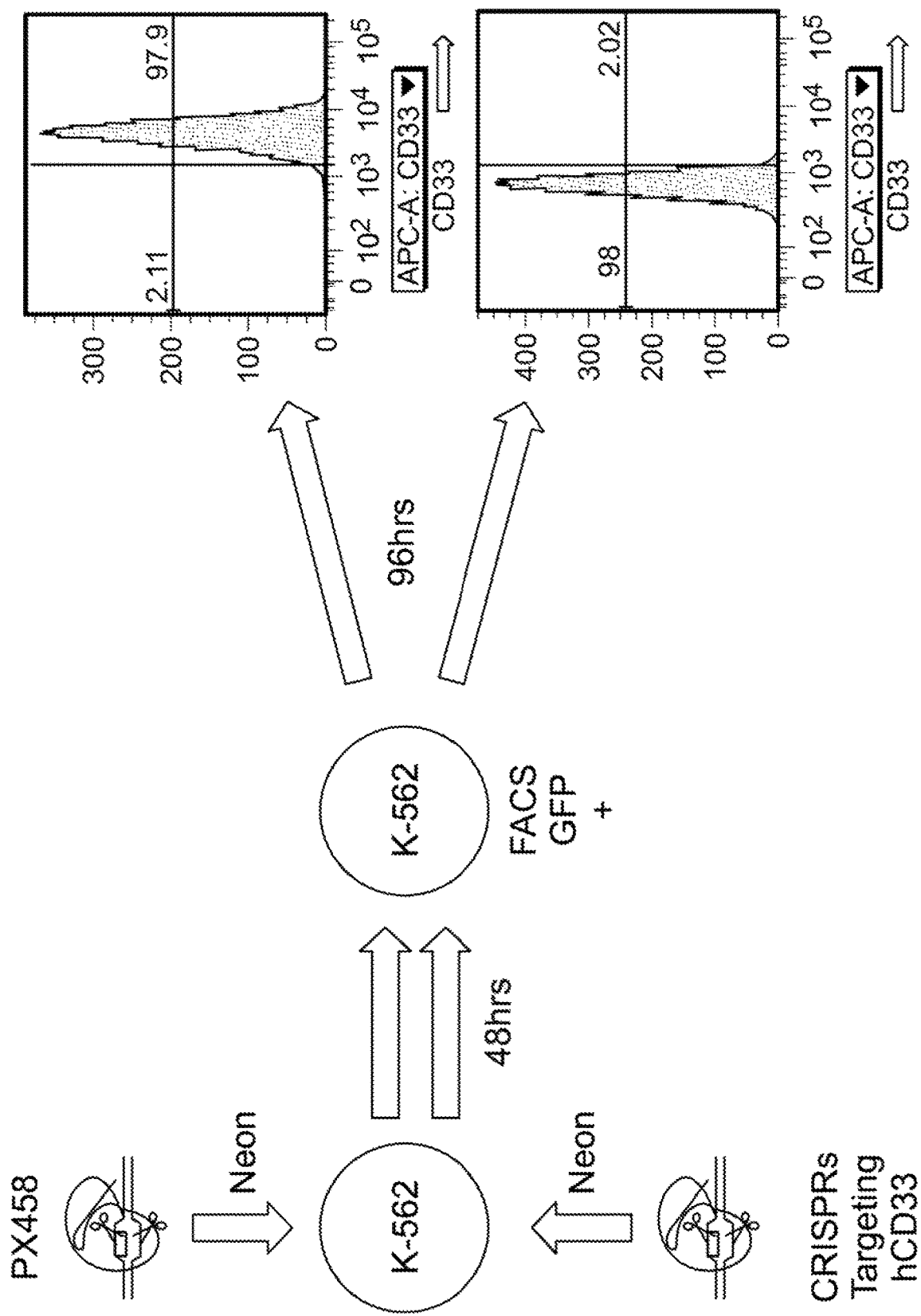
FIG. 5 is a schematic showing a genome editing strategy using the CRISPR/Cas9 system to disrupt CD33. A PX458 vector encoding a Cas9 protein and a guide RNA targeting CD33 was nucleofected into K-562 cells, a human leukemic cell line. Flow cytometry was performed on the cell population using an anti-CD33 antibody prior to (top plot) and after (bottom plot) delivery of Cas9 and guide RNA to the cells. The genome editing resulted in the deletion of a coding region of the gene and a significant reduction in CD33 from the cell surface.

In some embodiments, the present disclosure provides compositions and methods for inhibiting a cell-surface lineage-specific antigen in hematopoietic cells using a CRISPR/Cas9 system, wherein guide RNA sequence hybridizes to the nucleotide sequence encoding the cell-surface lineage-specific antigen. In some embodiments, the cell-surface lineage-specific antigen is CD33 and the gRNA hybridizes to a portion of the nucleotide sequence that encodes the CD33 (FIG. 5). Examples of gRNAs that target CD33 are provided in Table 4, although additional gRNAs may be developed that hybridize to CD33 and can be used in the methods described herein.

Table 4 provides exemplary guide RNA sequences that hybridize or are predicted to hybridize to a portion of CD33.

TABLE 4

Guide RNA sequences targeting CD33

| Name | Guide sequence | Guide position | Score |
|---|---|---|---|
| hCD33-IgC1 referred to herein as "Crispr 1" | ACCTGTCAGGTGAAGTTCGC TGG (SEQ ID NO: 11) | Chr19:+51729270 | 87 |
| hCD33-IgC3 referred to herein as "Crispr 3" | TGGCCGGGTTCTAGAGTGCC AGG (SEQ ID NO: 28) | Chr19:-51729087 | 82 |
| hCD33-IgC5 referred to herein as "Crispr 5" | GGCCGGGTTCTAGAGTGCCA GGG (SEQ ID NO: 29) | Chr19:-51729086 | 81 |
| hCD33 gRNA | CACCGAGGAGTGAGTAGTCC TGG (SEC ID NO: 30) | | |
| hCD33 gRNA | TCCAGCGAACTTCACCTGAC AGG (SEG ID NO: 31) | | |

In some embodiments, it may be desired to further genetically engineer the HSC, particularly allogeneic HSCs, to reduce the graft-versus-host effects. For example, the standard therapy for relapsed AML is hematopoietic stem cell transplantation (HSCT). However, at least one of the limiting factors for successful HSCT is graft-versus-host disease (GVHD), which expression of the cell surface molecule CD45 has been implicated. See, e.g., Van Besie, *Hematology Am. Soc. Hematol Educ Program* (2013)56; Mawad *Curr. Hematol. Malig. Rep.* (2013) 8(2):132. CD45RA and CD45RO are isoforms of CD4S (found on all hematopoietic cells except erythrocytes). In T lymphocytes, CD45RA is expressed on naive cells, while CD45RO is expressed on memory cells. CD45RA T cells have a high potential for reactivity against recipient-specific antigens following HSCT, resulting in GVHD. Thus, there remains a need for efficient and safe AML treatment that would also reduce the possibility of transplant rejection or GVHD. CD45 is a type 1 lineage antigen, since CD45 bearing cells are required for survival but the antigen may be deleted from stem cells using CRISPR.

Taking into account the complications arising due to the development of GvHD following HSCT, the present disclosure also provides compositions and methods for targeting CD45RA. Such compositions and methods are meant to prevent and/or reduce the incidence or extent of GvHD.

Thus, in the case of GVHD, the treatment of the patient can involve the following steps: (1) administering a therapeutically effective amount of a T cell to the patient, where the T cell comprises a nucleic acid sequence encoding a chimeric antigen receptor (CAR) targeting CD45RA lineage specific antigen; and (2) infusing the patient with hematopoietic stem cells, where the hematopoietic cells have reduced expression of CD45RA lineage specific antigen.

Additionally, the present disclosure provides compositions and methods for the combined inhibition of both CD33 and CD45RA lineage specific antigens. Such treatment regimen can involve the following steps: (1) administering a therapeutically effective amount of a T cell to the patient, where the T cell comprises a nucleic acid sequence encoding a chimeric antigen receptor (CAR) targeting both CD33 and CD4SRA lineage specific antigens; and (2) infusing or reinfusing the patient with hematopoietic stem cells, either autologous or allogeneic, where the hematopoietic cells have reduced expression of both the CD33 and CD45RA lineage specific antigens.

Figure 6:
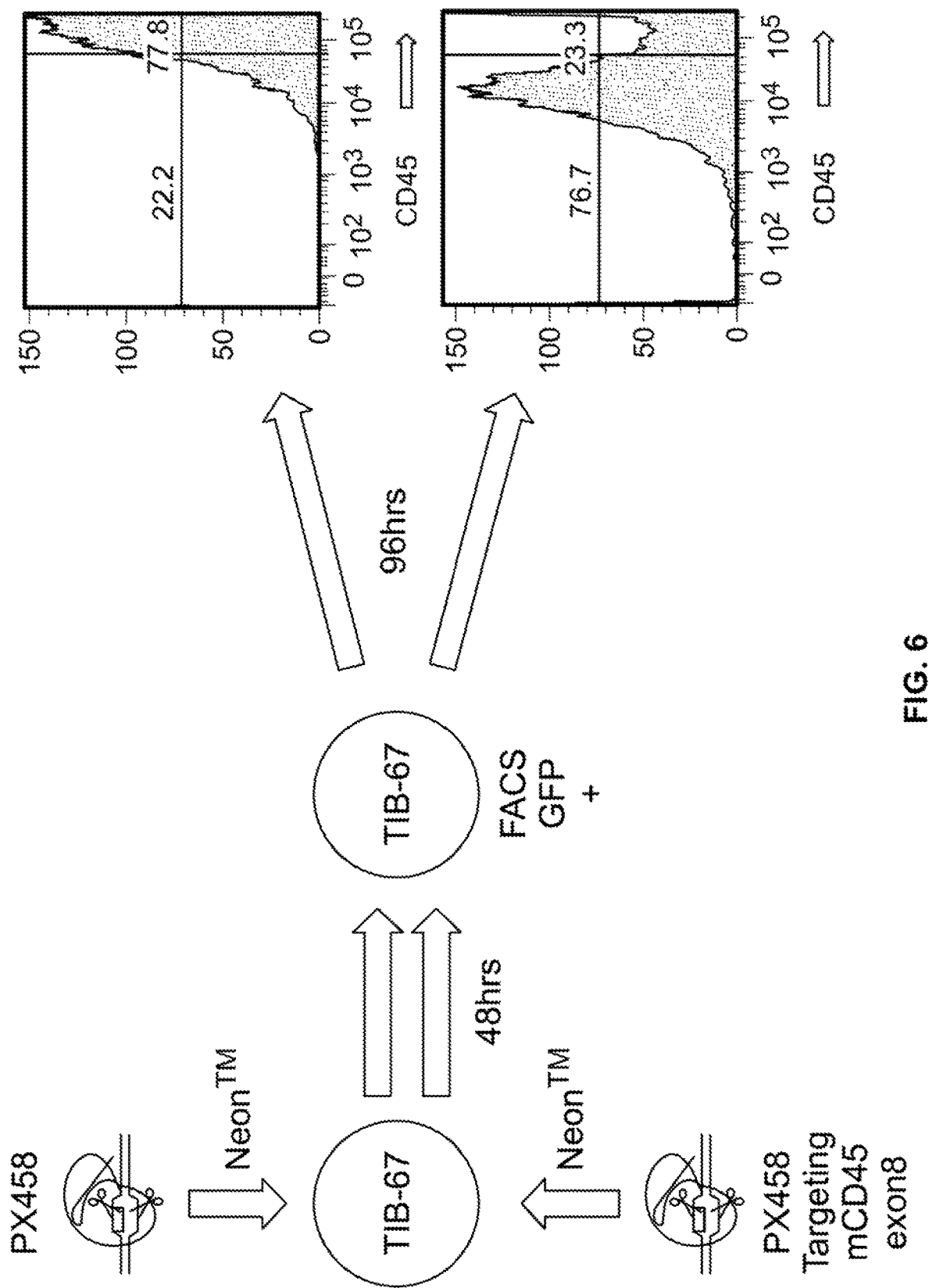
FIG. 6 is a schematic showing a genome editing strategy using the CRISPR/ICas9 system to disrupt CD45RA. A PX458 vector encoding a Cas9 protein and a guide RNA targeting CD45RA was nucleofected into TIB-67 reticulum cell sarcoma mouse macrophage-like cells. Flow cytometry was performed on the cell population using an anti-CD45RA antibody prior to (top plot) and after (bottom plot) delivery of Cas9 and guide RNA to the cells. The genome editing resulted in the deletion of a coding region of the gene and a significant reduction in CD45RA from the cell surface.
Figure 7A:
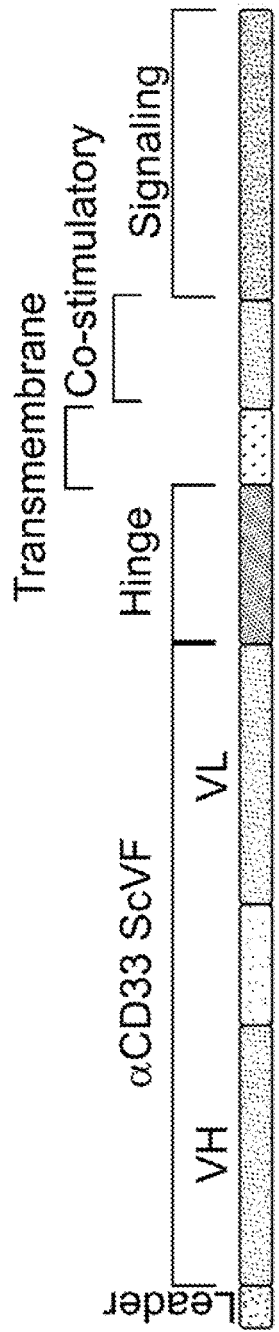
FIGS. 7A-7D show schematics of example chimeric receptors comprising antigen-binding fragments that target CD33.
Figure 7B:
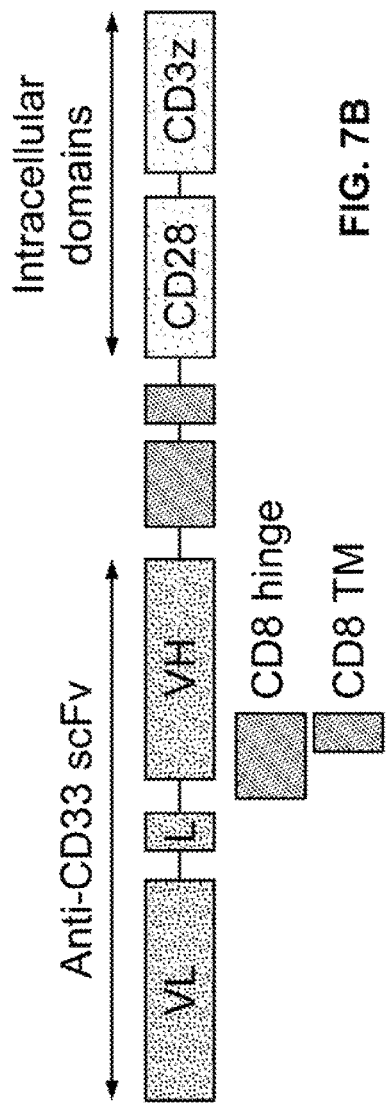
Figure 7C:
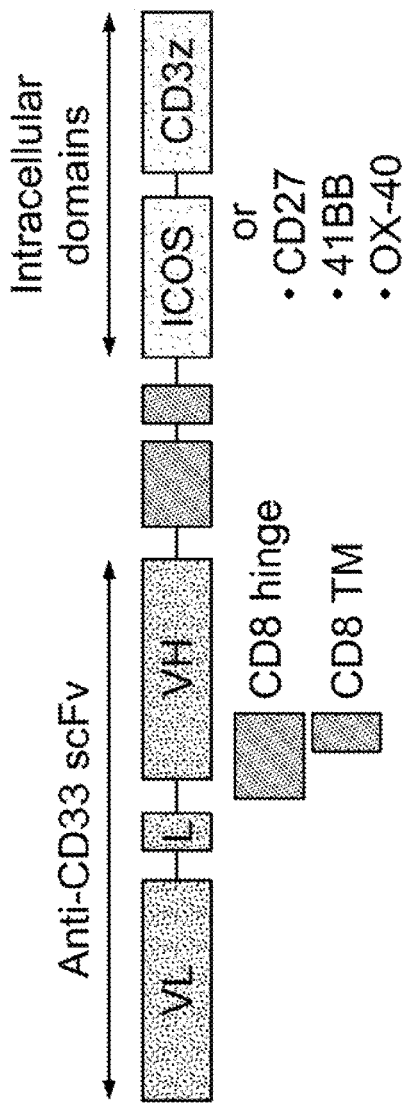
Figure 7D:
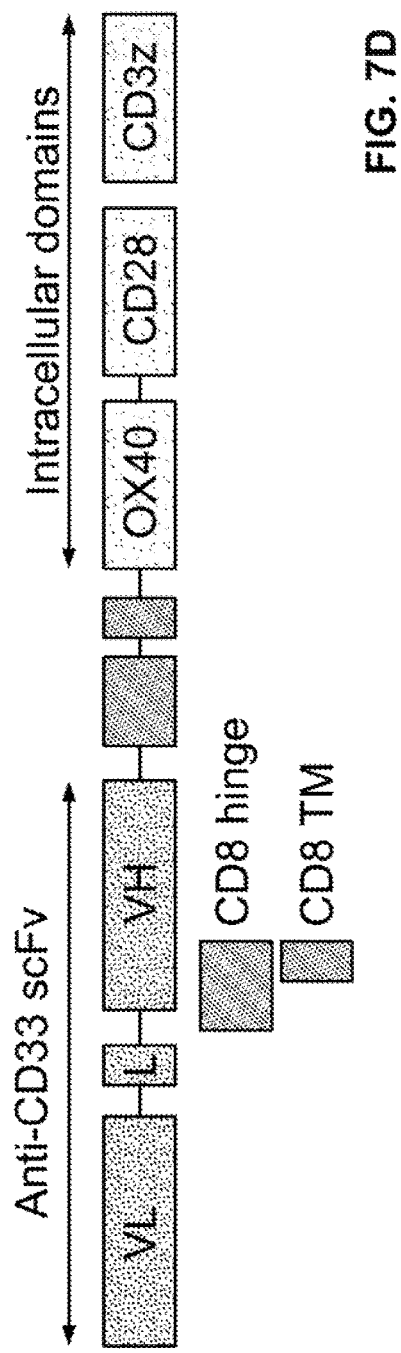

In some embodiments, the cell-surface lineage-specific antigen CD45RA is also deleted or inhibited in the hematopoietic cells using a CRISPR/Cas9 system. In some embodiments, the gRNA sequence hybridizes to a portion of the nucleotide sequence encoding CD45RA (FIG. 6). Examples of gRNAs that target CD4SRA are provided in Table 5, although additional gRNAs may be developed that hybridize to CD45RA and can be used in the methods described herein.

Table 5 provides exemplary guide RNA sequences that hybridize or are predicted to hybridize to exon 4 or exon S of human CD45.

TABLE 5

Guide RNA sequences targeting CD45

| hCD45 Target | Guide RNA |
|---|---|
| Exon 4 | CCAAAGAGTCCGGGGATACT TGG (SEQ ID NO: 9) |
| | CCAAGTATCCCCGGACTCTT TGG (SEQ ID NO: 32) |
| | AGCATTATCCAAAGAGTCCG GGG (SEQ ID NO: 33) |
| | ACTTGGGTGGAAGTATTGTC TGG (SEQ ID NO: 34) |
| Exon 5 | GTTGAGTTTTGCATTGGCGG CGG (SEQ ID NO: 10) |
| | GTCTGCGAGTCTGCGTGCGT GGG (SEQ ID NO: 35) |
| | CGTCTGCGAGTCTGCGTGCG TGG (SEQ ID NO: 36) |
| | GCGAGTCTGCGTGCGTGGGA AGG (SEQ ID NO: 37) |

Also provided herein are methods of producing a cell that is deficient in a cell-surface lineage-specific antigen involving providing a cell and introducing into the cell components of a CRISPR Cas system for genome editing. In some embodiments, a nucleic acid that comprises a CRISPR-Cas guide RNA (gRNA) that hybridizes or is predicted to hybridize to a portion of the nucleotide sequence that encodes the lineage-specific cell-surface antigen is introduced into the cell. In some embodiments, the gRNA is introduced into the cell on a vector. In some embodiments, a Cas endonuclease is introduced into the cell. In some embodiments, the Cas endonuclease is introduced into the cell as a nucleic acid encoding a Cas endonuclease. In some embodiments, the gRNA and a nucleotide sequence encoding a Cas endonuclease are introduced into the cell on the same nucleic acid (e.g., the same vector). IN some embodiments, the Cas endonuclease is introduced into the cell in the form of a protein. In some embodiments, the Cas endonuclease and the gRNA are pre-formed in vitro and are introduced to the cell in as a complex.

The present disclosure further provides engineered, non-naturally occurring vectors and vector systems, which can encode one or more components of a CRISPR/Cas9 complex, wherein the vector comprises a polynucleotide encoding (i) a (CRISPR)-Cas system guide RNA that hybridizes to the lineage specific antigen sequence and (ii) a Cas9 endonuclease.

Vectors of the present disclosure can drive the expression of one or more sequences in mammalian cells using a mammalian expression vector. Examples of mammalian expression vectors include pCDM8 (Seed, *Nature* (1987) 329: 840) and pMT2PC (Kaufman, et al., *EMBO J.* (1987) 6: 187). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL 2nd eds., Cold Spring Harbor Laboratory, Cold Spring Harbor Laboratory Press, Cold Spring Harbor, N.Y., 1989.

The vectors of the present disclosure are capable of directing expression of the nucleic acid preferentially in a particular cell type (e.g., tissue-specific regulatory elements are used to express the nucleic acid). Such regulatory elements include promoters that may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining.

Conventional viral and non-viral based gene transfer methods can be used to introduce nucleic acids encoding CRISPR/Cas9 in mammalian cells or target tissues. Such methods can be used to administer nucleic acids encoding components of a CRISPR-Cas system to cells in culture, or in a host organism. Non-viral vector delivery systems include DNA plasmids, RNA (e.g., a transcript of a vector described herein), naked nucleic acid, and nucleic acid complexed with a delivery vehicle. Viral vector delivery systems include DNA and RNA viruses, which have either episomal or integrated genomes after delivery to the cell. For a review of gene therapy procedures.

Viral vectors can be administered directly to patients (in vivo) or they can be used to manipulate cells in vitro or ex vivo, where the modified cells may be administered to patients. In one embodiment, the present disclosure utilizes viral based systems including, but not limited to retroviral, lentivirus, adenoviral, adeno-associated and herpes simplex virus vectors for gene transfer. Furthermore, the present disclosure provides vectors capable of integration in the host genome, such as retrovirus or lentivirus. Preferably, the vector used for the expression of a CRISPR-Cas system of the present disclosure is a lentiviral vector.

In one embodiment, the disclosure provides for introducing one or more vectors encoding CRISPR-Cas into eukaryotic cell. The cell can be a cancer cell. Alternatively, the cell is a hematopoietic cell, such as a hematopoietic stem cell. Examples of stem cells include pluripotent, multipotent and unipotent stem cells. Examples of pluripotent stem cells include embryonic stem cells, embryonic germ cells, embryonic carcinoma cells and induced pluripotent stem cells (iPSCs). In a preferred embodiment, the disclosure provides introducing CRISPR-Cas9 into a hematopoietic stem cell.

The vectors of the present disclosure are delivered to the eukaryotic cell in a subject. Modification of the eukaryotic cells via CRISPR/Cas9 system can takes place in a cell culture, where the method comprises isolating the eukaryotic cell from a subject prior to the modification. In some embodiments, the method further comprises returning said eukaryotic cell and/or cells derived therefrom to the subject.

Combined Therapy

As described herein, agents comprising an antigen-binding fragment that binds to a cell-surface lineage-specific antigen may be administered to a subject in combination with hematopoietic cells that are deficient for the cell-surface lineage-specific antigen. As used herein, "subject," "individual," and "patient" are used interchangeably, and refer to a vertebrate, preferably a mammal such as a human. Mammals include, but are not limited to, human primates, non-human primates or murine, bovine, equine, canine or feline species. In some embodiments, the subject is a human patient having a hematopoietic malignancy.

In some embodiments, the agents and/or the hematopoietic cells may be mixed with a pharmaceutically acceptable carrier to form a pharmaceutical composition, which is also within the scope of the present disclosure.

To perform the methods described herein, an effective amount of the agent comprising an antigen-binding fragment that binds to a cell-surface lineage-specific antigen and an effective amount of hematopoietic cells can be co-administered to a subject in need of the treatment. As used herein the term "effective amount" may be used interchangeably with the term "therapeutically effective amount" and refers to that quantity of an agent, cell population, or pharmaceutical composition (e.g., a composition comprising agents and/or hematopoietic cells) that is sufficient to result in a desired activity upon administration to a subject in need thereof. Within the context of the present disclosure, the term "effective amount" refers to that quantity of a compound, cell population, or pharmaceutical composition that is sufficient to delay the manifestation, arrest the progression, relieve or alleviate at least one symptom of a disorder treated by the methods of the present disclosure. Note that when a combination of active ingredients is administered the effective amount of the combination may or may not include amounts of each ingredient that would have been effective if administered individually.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject is a human patient having a hematopoietic malignancy.

As described herein, the hematopoietic cells and/or immune cells expressing chimeric receptors may be autologous to the subject, e.g, the cells are obtained from the subject in need of the treatment, genetically engineered to be deficient for expression of the cell-surface lineage-specific antigen or for expression of the chimeric receptor constructs, and then administered to the same subject. Administration of autologous cells to a subject may result in reduced rejection of the host cells as compared to administration of non-autologous cells. Alternatively, the host cells are allogeneic cells, i.e., the cells are obtained from a first subject, genetically engineered to be deficient for expression of the cell-surface lineage-specific antigen or for expression of the chimeric receptor constructs, and administered to a second subject that is different from the first subject but of the same species. For example, allogeneic immune cells may be derived from a human donor and administered to a human recipient who is different from the donor.

In some embodiments, the immune cells and/or hematopoietic cells are allogeneic cells and have been further genetically engineered to reduced graft-versus-host disease. For example, as described herein, the hematopoietic stem cells may be genetically engineered (e.g., using genome editing) to have reduced expression of CD45RA.

In some embodiments, the immune cells expressing any of the chimeric receptors described herein are administered to a subject in an amount effective in to reduce the number of target cells (e.g., cancer cells) by least 20%, e.g., 50%, 80%, 100%, 2-fold, 5-fold, 10-fold, 20-fold, 50-fold, 100-fold or more.

A typical amount of cells, i.e., immune cells or hematopoietic cells, administered to a mammal (e.g., a human) can be, for example, in the range of one million to 100 billion cells; however, amounts below or above this exemplary range are also within the scope of the present disclosure. For example, the daily dose of cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), more preferably about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

In one embodiment, the chimeric receptor (e.g., a nucleic acid encoding the chimeric receptor) is introduced into an immune cell, and the subject (e.g., human patient) receives an initial administration or dose of the immune cells expressing the chimeric receptor. One or more subsequent administrations of the agent (e.g., immune cells expressing the chimeric receptor) may be provided to the patient at intervals of 15 days, 14, 13, 12, 11, 10, 9, 8, 7, 6, 5, 4, 3, or 2 days after the previous administration. More than one dose of the agent can be administered to the subject per week, e.g., 2, 3, 4, or more administrations of the agent. The subject may receive more than one doses of the agent (e.g., an immune cell expressing a chimeric receptor) per week, followed by a week of no administration of the agent, and finally followed by one or more additional doses of the agent (e.g., more than one administration of immune cells expressing a chimeric receptor per week). The immune cells expressing a chimeric receptor may be administered every other day for 3 administrations per week for two, three, four, five, six, seven, eight or more weeks.

In the context of the present disclosure insofar as it relates to any of the disease conditions recited herein, the terms "treat," "treatment." and the like mean to relieve or alleviate at least one symptom associated with such condition, or to slow or reverse the progression of such condition. Within the meaning of the present disclosure, the term "treat" also denotes to arrest, delay the onset (i.e., the period prior to clinical manifestation of a disease) and/or reduce the risk of developing or worsening a disease. For example, in connection with cancer the term "treat" may mean eliminate or reduce a patient's tumor burden, or prevent, delay or inhibit metastasis, etc.

In some embodiments, an agent comprising an antigen-binding fragment that binds a cell-surface lineage-specific antigen and a population of hematopoietic cells deficient in the cell-surface lineage-specific antigen. Accordingly, in such therapeutic methods, the agent recognizes (binds) a target cell expressing the cell-surface lineage-specific antigen for targeting killing. The hematopoietic cells that are deficient in the antigen allow for repopulation of a cell type that is targeted by the agent. In some embodiments, the treatment of the patient can involve the following steps; (1) administering a therapeutically effective amount of an agent targeting a cell-surface lineage-specific antigen to the patient and (2) infusing or reinfusing the patient with hematopoietic stem cells, either autologous or allogenic, where the hematopoietic cells have reduced expression of a lineage specific disease-associated antigen. In some embodiments, the treatment of the patient can involve the following steps: (1) administering a therapeutically effective amount of an immune cell expressing a chimeric receptor to the patient, wherein the immune cell comprises a nucleic acid sequence encoding a chimeric receptor that binds a cell-surface lineage-specific, disease-associated antigen; and (2) infusing or reinfusing the patient with hematopoietic cells (e.g., hematopoietic stem cells), either autologous or allogenic, where the hematopoietic cells have reduced expression of a lineage specific disease-associated antigen.

The efficacy of the therapeutic methods using a an agent comprising an antigen-binding fragment that binds a cell-surface lineage-specific antigen and a population of hematopoietic cells deficient in the cell-surface lineage-specific antigen may be assessed by any method known in the art and would be evident to a skilled medical professional. For example, the efficacy of the therapy may be assessed by survival of the subject or cancer burden in the subject or tissue or sample thereof. In some embodiments, the efficacy of the therapy is assessed by quantifying the number of cells belonging to a particular population or lineage of cells. In some embodiments, the efficacy of the therapy is assessed by quantifying the number of cells presenting the cell-surface lineage-specific antigen.

In some embodiments, the agent comprising an antigen-binding fragment that binds to the cell-surface lineage-specific antigen and the population of hematopoietic cells IS administered concomitantly.

In some embodiments, the agent comprising an antigen-binding fragment that binds a cell-surface lineage-specific antigen (e.g., immune cells expressing a chimeric receptor as described herein) is administered prior to administration of the hematopojetic cells. In some embodiments, the agent comprising an antigen-binding fragment that binds a cell-surface lineage-specific antigen (e.g., immune cells expressing a chimeric receptor as described herein) is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the hematopoietic cells.

In some embodiments, the hematopoietic cells are administered prior to the agent comprising an antigen-binding fragment that binds a cell-surface lineage-specific antigen (e.g., immune cells expressing a chimeric receptor as described herein). In some embodiments, the population of hematopoietic cells is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the agent comprising an antigen-binding fragment that binds to the cell-surface lineage-specific antigen.

In some embodiments, the agent targeting the cell-surface lineage-specific antigen and the population of hematopoietic cells are administered at substantially the same time. In some embodiments, agent targeting the cell-surface lineage-specific antigen is administered and the patient is assessed for a period of time, after which the population of hematopoietic cells is administered. In some embodiments, the population of hematopoietic cells is administered and the patient is assessed for a period of time, after which agent targeting the cell-surface lineage-specific antigen is administered.

Also within the scope of the present disclosure are multiple administrations (e.g., doses) of the agents and/or populations of hematopoietic cells. In some embodiments, the agents and/or populations of hematopoietic cells are administered to the subject once. In some embodiments, agents and/or populations of hematopoietic cells are administered to the subject more than once (e.g., at least 2, 3, 4, 5, or more times). In some embodiments, the agents and/or populations of hematopoietic cells are administered to the subject at a regular interval, e.g., every six months.

In some embodiments, the subject is a human subject having a hematopoietic malignancy. As used herein a hematopoietic malignancy refers to a malignant abnormality involving hematopoietic cells (e.g., blood cells, including progenitor and stem cells). Examples of hematopoietic malignancies include, without limitation, Hodgkin's lymphoma, non-Hodgkin's lymphoma, leukemia, or multiple myeloma. Leukemias include acute myeloid leukaemia, acute lymphoid leukemia, chronic myelogenous leukaemia, acute lymphoblastic leukemia or chronic lymphoblastic leukemia, and chronic lymphoid leukemia.

In some embodiments, the leukemia is acute myeloid leukaemia (AML). AML is characterized as a heterogeneous, clonal, neoplastic disease that originates from transformed cells that have progressively acquired critical genetic changes that disrupt key differentiation and growth-regulatory pathways. (Dohner et al., *NEJM*, (2015) 373:1136). CD33 glycoprotein is expressed on the majority of myeloid leukemia cells as well as on normal myeloid and monocytic precursors and has been considered to be an attractive target for AML therapy (Laszlo et al., *Blood Rev.* (2014) 28(4): 143-53). While clinical trials using anti CD33 monoclonal antibody based therapy have shown improved survival in a subset of AML patients when combined with standard chemotherapy, these effects were also accompanied by safety and efficacy concerns.

Other efforts aimed at targeting AML cells have involved the generation of T cells expressing chimeric antigen receptors (CARs) that selectively target CD33 in AML. Buckley et al., *Curr. Hematol. Malig. Rep.* (2):65 (2015). However, the data is limited and there are uncertainties about how effective (whether all targeted cells are eliminated) this approach may be in treating the patient. Additionally, since myeloid lineage cells are indispensable for life, depleting a subject of myeloid lineage cells could have detrimental effects on survival of the patient. The present disclosure aims at, at least in part, solving such problems associated with AML treatment.

Alternatively or in addition, the methods described herein may be used to treat non-hematopoietic cancers, including without limitation, lung cancer, ear, nose and throat cancer, colon cancer, melanoma, pancreatic cancer, mammary cancer, prostate cancer, breast cancer, ovarian cancer, basal cell carcinoma, biliary tract cancer; bladder cancer; bone cancer; breast cancer; cervical cancer; choriocarcinoma; colon and rectum cancer; connective tissue cancer, cancer of the digestive system; endometrial cancer; esophageal cancer; eye cancer; cancer of the head and neck; gastric cancer; intraepithelial neoplasm; kidney cancer; larynx cancer; liver cancer; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Carcinomas are cancers of epithelial origin. Carcinomas intended for treatment with the methods of the present disclosure include, but are not limited to, acinar carcinoma, acinous carcinoma, alveolar adenocarcinoma (also called adenocystic carcinoma, adenomyoepitheliona, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Huirthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypemephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum. In preferred embodiments, the methods of the present disclosure are used to treat subjects having cancer of the breast, cervix, ovary, prostate, lung, colon and rectum, pancreas, stomach or kidney.

Sarcomas are mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., non-bone) Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

In some embodiments, the cancer to be treated can be a refractory cancers. A "refractory cancer," as used herein, is a cancer that is resistant to the standard of care prescribed. These cancers may appear initially responsive to a treatment (and then recur), or they may be completely non-responsive to the treatment. The ordinary standard of care will vary depending upon the cancer type, and the degree of progression in the subject. It may be a chemotherapy, or surgery, or radiation, or a combination thereof. Those of ordinary skill in the art are aware of such standards of care. Subjects being treated according to the present disclosure for a refractory cancer therefore may have already been exposed to another treatment for their cancer. Alternatively, if the cancer is likely to be refractory (e.g., given an analysis of the cancer cells or history of the subject), then the subject may not have already been exposed to another treatment. Examples of refractory cancers include, but are not limited to, leukemia, melanomas, renal cell carcinomas, colon cancer, liver (hepatic) cancers, pancreatic cancer, Non-Hodgkin's lymphoma and lung cancer.

Any of the immune cells expressing chimeric receptors described herein may be administered in a pharmaceutically acceptable carrier or excipient as a pharmaceutical composition.

The phrase "pharmaceutically acceptable," as used in connection with compositions and/or cells of the present disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions and/or cells to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: *The Science and Practice of Pharmacy* 20th Ed. (2000) Lippincott Williams and Wilkins, Ed. K. E. Hoover.

Kits for Therapeutic Uses

Also within the scope of the present disclosure are kits for use of the agents targeting cell-surface lineage-specific antigens in combination with populations of hematopoietic cells that are deficient in the cell-surface lineage-specific antigen. Such kits may include one or more containers comprising a first pharmaceutical composition that comprises any agent comprising an antigen-binding fragment that binds a cell-surface lineage-specific antigen (e.g., immune cells expressing chimeric receptors described herein), and a pharmaceutically acceptable carrier, and a second pharmaceutical composition that comprises a population of hematopoietic cells that are deficient in the cell-surface lineage-specific antigen (e.g., a hematopoietic stem cell) and a pharmaceutically acceptable carrier.

In some embodiments, the kit can comprise instructions for use in any of the methods described herein. The included instructions can comprise a description of administration of the first and second pharmaceutical compositions to a subject to achieve the intended activity in a subject. The kit may further comprise a description of selecting a subject suitable for treatment based on identifying whether the subject is in need of the treatment. In some embodiments, the instructions comprise a description of administering the first and second pharmaceutical compositions to a subject who is in need of the treatment.

The instructions relating to the use of the agents targeting cell-surface lineage-specific antigens and the first and second pharmaceutical compositions described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the pharmaceutical composition is a chimeric receptor variants as described herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the an. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J, B. Griffiths, and D. G. Newell, eds. 1993-8) J. Wiley and Sons; Methods in Enzymology (Academic Press, Inc.): Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999): The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: In Vitro Deletion of CD33 in a Human Leukemic Cell Line

In order to test the ability of CRSPR-Cas9 system to target CD33 in vitro, human leukemic cells K-562 were co-transfected using Neon™ (Thermo Fisher Scientific) with Cas9-GFP (PX458, *S. pyogenes*) and a guide RNA containing NGG PAM sequence (FIG. 4) where guide RNA was designed to target hCD33 genomic sequence. 48 hours post-transfection, cells expressing Cas9 were identified and isolated using FACS sorting for GFP. Cells were then incubated for 96 hours and tested for CD33 expression by flow cytometry (FIG. 5). Flow cytometry plots using an anti-CD33 antibody show CD33 expression by the K-562 cells before (top plot) and after (bottom plot) delivery of Cas9 vector and guide RNA. As shown in FIG. 5, 98% of the cells lacked the CD33 expression following transfection.

This example demonstrates the efficient deletion of CD33 using CRISPR-Cas9 system in human leukemic cells.

Example 2: In Vitro Deletion of CD4S in Human Leukemic Cell Lines

The CRISPR-Cas9 system was used to target CD45RA in vitro. Briefly, TIB-67 reticulum cell sarcoma mouse macrophage-like cells were co-transfected using Neon™ reagent (Thermo Fisher Scientific) with Cas9-GFP (PX458, *S. pyogenes*) and CRISPRs gRNAs (containing the "NGG" PAM sequence) targeting hCD45RA genomic sequence. 48 hours post-transfection, cells expressing CRISPR-Cas9 system were identified and isolated using FACS sorting for GFP. Cells were then incubated for 96 hours and tested for CD45RA expression (FIG. 6). Flow cytometry plots using CD45RA antibody show CD4SRA expression before (top plot) and after (bottom plot) delivery of Cas9 vector and guide RNA.

Similar to Example 1, where CD33 expression was successfully reduced in leukemic cells, findings in this Example indicate efficient targeting of CD45RA using the CRISPR-Cas9 system.

Example 3: Targeting Cell-Surface Lineage-Specifc CD33 in Acute Myelold Leukemia (AML)

The present example encompasses targeting of the CD33 antigen in AML. The specific steps of the example are outlined in Table 6.

TABLE 6

Outline of the Experimental Design

| | |
|---|---|
| I. Autologous CD33 targeted (CAR) T-cell therapy | 1. Generation of anti-CD33 CAR constructs |
| | 2. Isolation of CD8*T Cells from a Patient |
| | 3. Preparation of anti CD33 CAR T Cells of |
| | 4. Reinfusion of CD33 CAR T cells into a Patient |
| II. Autologous Hematopoietic Stem Cell Transplant Using | 1. Isolation of Hematopoietic Stem Cells |
| | 2. CRISPR-Cas9 Plasmid Targeting CD33 |
| | 3. Generation of CD34⁻CD33⁻ cells via CRISPR-CAS System |

TABLE 6-continued

Outline of the Experimental Design

| CD34⁺CD33⁻ Cells III. Continued treatment of a patient with a CD33 antibody attached to a toxin (immunotoxin) | 4. Reinfusion of CD34⁻CD33⁻ cells into a Patient |

I. CD33-Targeted Chimeric Antigen Receptor (CAR) T-Cell Therapy

A. Generation of Anti-CD33 CAR Constructs

The chimeric antigen receptors targeting CD33 described herein may consist of the following components in order from 5' to 3': pHIV-Zsgreen lentiviral backbone (www.addgene.org/18121/), peptide signal, the CD33 scFv, the hinge, transmembrane regions of the CD28 molecule, the intracellular domain of CD28, and the signaling domain of TCR-ζ molecule.

Initially, peptide signal, anti-CD33 light chain (SEQ ID NO: 1) the flexible linker and the anti-CD33 heavy chain (SEQ ID. NO. 2) are cloned into the EcoRI site of pHIV-Zsgreen, with an optimal Kozak sequence.

The nucleic acid sequences of an exemplary chimeric receptors that binds CD33 with the basic structure of Light chain-linker-Heavy chain-Hinge-CD28/ICOS-CD3ζ is provided below.

Part 1: Light chain-linker-Heavy chain (SEQ ID NO: 16): The Kozak start site is shown in boldface. The peptide signal L1 is shown in italic. The anti-CD33 light chain and heavy chain are shown in bold and italics, separated by a linker.

ggtgtcgtgagcggccgctgaactgGCCACC<u>ATG</u>GACATGAGGGTCCC

*TGCTCAGCTCCTGGGGCTCCTGCTGCTCTGGCTCTCAGGTGCCAGATG*

*TGAGATCGTGCTGACCCAGAGCCCCGGCAGCCTGGCCGTGAGC*

*CCCGGCAAGAGGGTGACCATGAGCTGCAAGAGCAGCCAGAG*

*CGTGTTCTTCAGCAGCAGCCAGAAGAACTACCTGGCCT*

*GGTACCAGCAGATCCCCGGCCAGAGCCCCAGGCTGCTGATCTACT*

*GGGCCAGCACCAGGGAGAGCGGCGTGCCCGACAGGTT*

*CACCGGCAGCGGCAGCGGCAGCGGCACCGACTTCACCCT*

*GACCATCAGCAGCGTGCAGCCCGAGGACCTGGCCATCTACTA*

*CTGCCACCAGTACCTGAGCAGCAGGACCTTCGGCCAGGG*

*CACCAAGCTGGAGATCAAGAGG*GGCAGCACCAGCGGCAGCGGCAAGC

CCGGCAGCGGCGAGGGCAGCACCAAGGGC

*CAGGTGCAGCTGCAGCAGCCCGGCGCCGAGGTGGTGAAGCCCGG*

*CGCCAGCGTGAAGATGAGCTGCAAGGCCAGCGGCTACAC*

*CTTCACCAGCTACTACATCCACTGGATCAAGCAGACCCCCGGC*

*CAGGGCCTGGAGTGGGTGGGCGTGATCTACCCCGGCAA*

*CGACGACATCAGCTACAACCAGAAGTTCCAGGGCAAGGC*

*CACCCTGACCGCCGACAAGAGCAGCACCACCGCCTACATGCA*

*GCTGAGCAGCCTGACCAGCGAGGACAGCGCCGTGTACTA*

*CTGCGCCAGGGAGGTGAGGCTGAGGTACTTCGACGTGTG*

*GGGCCAGGGCACCACCGTGACCGTGAGCAGC*

Part 2: Hinge-CD2/ICOS-CD3ζ NotI restriction enzyme recognition sites are shown in capitalization. The translational stop site is in boldface. The BamHI restriction cleavage site is shown in underline.

CD 28 costimulatory domain
(SEQ ID NO: 17)
GCGGCCGCAattgaagttatgtatcctcctccttacctagacaatgag aagagcaatggaaccattatccatgtgaaagggaaacacctttgtcca agtcccctatttcccggaccttctaagcccttttgggtgctggtggtg gttggtggagtcctggcttgctatagcttgctagtaacagtggccttt attattttctgggtgaggagtaagaggagcaggctcctgcacagtgac tacatgaacatgactccccgccgccccgggcccAcccgcaagcattac cagccctatgcccaccacgcgacttcgcagcctatcgctccagagtg aagttcagcaggagcgcagacgccccgcgtaccagcagggccagaac cagctctataacgagctcaatctaggacgaagagaggagtacgatgtt ttggacaagagacgtggccgggaccctgagatgggggaaagccgaga aggaagaaccctcaggaaggcctgtacaatgaactgcagaaagataag atggcggaggcctacagtgagattgggatgaaaggcgagcgccggagg ggcaaggggcacgatggcctttaccagggtctcagtacagccaccaag gacacctacgacgccttcacatgcaggccctgccccctcgcTAAcgc ccctctccctccccccccctaa ICOS costimulatory domain
(SEQ ID NO: 18)
GCGGCCGCActatcaattttttgatcctcctccttttaaagtaactctt acaggaggatatttgcatatttatgaatcacaactttgttgccagctg aagttctggttacccataggatgtgcagcctttgttgtagtctgcatt ttgggatgcatacttatttgttggcttacaaaaaagaagtattcatcc agtgtgcacgaccctaacggtgaatacatgttcatgagagcagtgaac acagccaaaaatctagactcacagatgtgaccctaagagtgaagttc agcaggagcgcagacgccccgcgtaccagcagggccagaaccagctc tataacgagctcaatctaggacgaagagaggagtacgatgttttggac aagagacgtggccgggaccctgagatgggggaaagccgagaaggaag aaccctcaggaaggcctgtacaatgaactgcagaaagataagatggcg gaggcctacagtgagattgggatgaaaggcgagcgccggaggggcaag gggcacgatggcctttaccagggtctcagtacagccaccaaggacacc tacgacgccttcacatgcaggccctgccccctcgcTAAcgcccctct ccctccccccccctaa Fusion (hybrid) CD28 and ICOS costimulatory domain
(SEQ ID NO: 19)
GCGGCCGCAattgaagttatgtatcctcctccttacctagacaatgag aagagcaatggaaccattatccatgtgaaagggaaacacctttgtcca -continued

```
agtccoctatttcccggaccttctaagccctttttgggtgctggtggtg gttggtggagtcctggcttgctatagcttgctagtaacagtggcctttt attattttctgggtgaggagtaagaggagcaggctcctgcacagtgac tacatgttcatgagagcagtgaacacagccaaaaaatctagactcaca gatgtgaccctaagagtgaagttcagcaggagcgcagacgccccgcg taccagcagggccagaaccagctctataacgagctcaatctaggacga agagaggagtacgatgttttggacaagagacgtggccgggaccctgag atgggggaaagccgagaaggaagaaccctcaggaaggcctgtacaat gaactgcagaaagataagatggcggaggcctacagtgagattgggatg aaaggcgagcgccggaggggcaaggggcacgatggcctttaccagggt ctcagtacagccaccaaggacacctacgacgcccttcacatgcaggcc ctgcccctcgcTAAcgcccctctccctcccccccctaa
```

In the next step, the hinge region, CD28 domain (SEQ ID NO: 3) and a cytoplasmic component of TCR-ζ are cloned into the Not and BamHI sites of pHIV-Zsgreen (already containing the peptide signal and the CD33 scFv. Alternatively, CD28 domain can be substituted by ICOS domain (SEQ ID NO: 4).

In addition to CD28 and ICOS domains, a fusion domain comprising fragments of CD28 and ICOS intracellular signaling domains will be engineered (SEQ ID NO: 5) and used to generate additional chimeric receptors. Such configuration, where the chimeric receptor comprises an antigen-binding fragment, an anti-CD33 light chain variable region, a linker, an anti-CD33 heavy chain variable region, CD28/ICOS hybrid region (including a TM region of CD28), and signaling domain of TCR-ζ molecule.

Example amino acid sequences of components that may be used to generate the chimeric receptors are provided herein, such as CD28 domain (SEQ ID NO: 6), ICOS domain (SEQ ID NO: 7), CD28/ICOS hybrid domain (SEQ ID NO: 8), and TCR-C are provided herein. Alternatively, the chimeric receptor may be generated as well (Section B.)

B. Alternative Method for Generation of anti-CD33 CAR Constructs

Schematics of example chimeric receptors are presented in FIG. 7, panels A-D. The chimeric receptor will be generated using an extracellular humanized scFv recognizing the CD33 antigen, linked to an extracellular CD8 hinge region, a transmembrane and cytoplasmic signaling domain, and a CD3 ζ-signaling chain (FIG. 7, panel B). DNA encoding the anti-CD33 chimeric receptor will be generated by using a humanized scFv (Essand et al., *J Intern Med*. (2013) 273(2):166). Alternatives include a CAR T cell that contains OX-1 or 41-BB in place of CD28 or CD28/OX1 or CD28/4-1-B-B hybrids (FIG. 7, panels C and D).

In order to generate the anti-CD33 scFV sequence, the coding regions of the heavy and light chains of the variable regions of the anti-CD33 antibody described above (SEQ ID NOs: 1 and 2) will be amplified with specific primers and cloned into a pHIV-Zsgreen vector for expression in cells. To evaluate the binding strength of the scFv (single chain variable fragments) to the target antigen, the scFv will be expressed in Hek293T cells. For this purpose, the vector (pHIV-Zsgreen containing the coding areas) will be transformed into *E. coli* Top10F bacteria and the plasmids prepared. The obtained expression vectors that code for the scFv antibodies will be introduced by transfection into Hek293T cells. After culturing the transfected cells for five days, the supernatant will be removed and the antibodies purified.

The resulting antibodies can be humanized using framework substitutions by protocols known in the art. See, for example, one such protocol is provided by BioAtla (San Diego), where synthetic CDR encoding fragment libraries derived from a template antibody are ligated to human framework region encoding fragments from a human framework pool limited to germline sequences from a functionally expressed antibodies (bioatla.com/applications/express-humanization/).

Affinity maturation may be performed in order to improve antigen binding affinity. This can be accomplished using general techniques known in the art, such as phage display (Schier R., *J. Mol. Biol* (1996), 263:551). The variants can be screened-for their biological activity (e.g., binding affinity) using for example Biacore analysis. In order to identify hypervariable region residues which would be good candidates for modification, alanine scanning mutagenesis can be performed to identify hypervariable region residues contributing significantly to antigen binding. Additionally, combinatorial libraries described by can also be used for improving the affinity of the antibodies (Rajpal et al., *PNAS* (2005) 102(24): 8466). Alternatively, BioAtla has developed a platform for the rapid and efficient affinity maturation of antibodies, which can also be utilized for the purposes of antibody optimization (bioatla.com/applications/functional-maturation/).

(C) Assembly of CAR Construct

Next, the anti-CD33 scFv will be linked to an extracellular CD8 hinge region, a transmembrane and cytoplasmic CD28 signaling domain, and a CD3 ζ-signaling chain. Briefly, primers specific for anti-CD33 scFv sequence will be used to amplify the scFv as described above. Plasmid (pUN1-CD8). (www.invivogen.com/puno-cd8a) carrying the complete human CD8 coding sequence will be used to amplify CD8 hinge and transmembrane domains (amino acids 135-205). CD3ζ fragment will be amplified from the Invivogen plasmid pORF9-hCD247a (http://www.invivogen.com/PDF/pORF9-hCD247a_10E26v06.pdf) carrying the complete human CD3ζ coding sequence. Finally, the CD28 (amino acids 153-220, corresponding to TM and signaling domains of CD28) will be amplified from cDNA generated using RNA collected from activated T cells by Trizol method. Fragments containing anti-CD33-scFv-CD8-hinge+TM-CD28-CD3ζ will be assembled using splice overlap extension (SOE) PCR. The resulting PCR fragment will then be cloned into pELPS lentiviral vector. pELPS is a derivative of the third-generation lentiviral vector pRRL-SIN-CMV*eGFP-WPRE in which the CMV promoter was replaced with the EF-1α promoter and the central polypurine tract of HIV was inserted 5' of the promoter (Milone et al., *Mol Ther*. (2009) (8): 1453, Porter et al., *NEJM* (2011) (8):725). All constructs will be verified by sequencing.

Alternatively, CARs containing ICOS, CD27, 41 BB, or OX-40 signaling domain instead of CD28 domain will be generated, introduced into T-cells and tested for the ability to eradicate CD33 positive cells (FIG. 7, panel C). The generation of "third-generation" chimeric receptors are also contemplated (FIG. 7, panel D), which combine multiple signaling domains, such as CD3z-CD28-41BB or CD3z-CD28-OX40, to further augment potency (Sadelain et al., *Cancer Discov*. (2013) 4:388).

(D) Anti-CD33 CAR T Cell Preparation

Primary human CD8$^+$ T cells will be isolated from patients' peripheral blood by immunomagnetic separation (Miltenyi Biotec). T cells will be cultured in complete media (RPMI 1640 supplemented with 10% heat-inactivated FBS, 100 U/mL penicillin, 100 µg/mL streptomycin sulfate, 10 mM HEPES) and stimulated with anti-CD3 and anti-CD28 mAbs-coated beads (Invitrogen) as previously described (Levine et al., *J. Immunol.* (1997) 159(12):5921).

A packaging cell line will be used to generate the viral vector, that is able to transduce target cells and contains the anti-CD33 chimeric receptors. To generate lentiviral particles, CARs generated in section (1) of this Example will be transfected into immortalized normal fetal renal 293T packaging cells together with Cells will be cultured with high glucose DMEM, including 10% FBS, 100 U/ml penicillin and 100 µg/ml streptomycin. 48-72 hours post-transfection the supernatant will be collected, and the recombinant lentivirus concentrated in DMEM without FBS. Primary $CD8^+$ T cells will next be transduced at multiplicity of infection (MOI) of ~5-10 in the presence of polybrene. Human recombinant IL-2 (R&D Systems) will be added every other day (50 IU/mL). T cells will be cultured for ~14 days after stimulation. Transduction efficiency of human primary T cells will be assessed by expression of a ZsGreen reporter gene (Clontech, Mountain View, Calif.).

E. Infusion of CAR T Cells into a Patient

Prior to the i.v. infusion of anti-CD33 CAR T cells into the patient, cells will be washed with phosphate buffered saline and concentrated. A cell processor such as a Haemonetics CellSaver (Haemonetics Corporation, Braintree, Mass.), which provides a closed and sterile system, will be used for the washing and concentration steps before formulation. The final T cells expressing the anti-CD33 chimeric receptors will be formulated into 100 ml of sterile normal saline supplemented with human serum albumin. Finally, patients will be infused with $1-10\times 10^7$ T cells/kg over a period of 1-3 days (Maude et al., *NEJM* (2014) 371(16):1507). The number of T cells expressing anti-CD33 chimeric receptors infused will depend on numerous factors such as the state of the cancer patient, patient's age, prior treatment, etc.

Furthermore, also contemplated herein are immune cells expressing chimeric receptors that target CD45RA in addition to chimeric receptors that target CD33 in AML patients. This can be accomplished by two different approaches: 1) generating immune cells expressing anti-CD33 chimeric receptors and immune cells expressing anti-CD47RA chimeric receptors separately and infusing the patient with both types of immune cells separately, or 2) generating immune cells that target both CD33 and CD45RA simultaneously (Kakarla et al., *Cancer* (2): 151 (2014)).

II. Autologous Hematopoietic Stem Cell Transplant (HSCT) Using $CD34^+CD33^-$ Cells It is understood that the protocols regarding stem cell isolation from patients, conditioning regimens, as well as infusion of patients with stem cells vary greatly depending on the patient's age, condition, treatment history, and institution where the treatment is conducted. Thus, the protocol described below is merely an example and is subject to routine optimization by a person having ordinary skill in the art.

A. Isolation of Hematopoietic Stem Cells Using Peripheral Blood Stem Cell (PBSC) Mobilization Following Adoptive Transfer of Anti-CD33 CAR T Cells AML patient will be stimulated by i.v. administration of granulocyte colony-stimulating factor (G-CSF) 10 mg/kg per day. $CD34^+$ cell positive selection will be performed using immunomagnetic beads and an immunomagnetic enrichment device. A minimum of $2\times 10^6$ $CD34^+$ cells/kg body weight are expected to be collected using a Fenwall CS 3000+ cell separator (Park et al. *Bone Marrow Transplantaion* (2003) 32:889).

B. Conditioning Regimen of a Patent

The conditioning regimen for autologous peripheral blood stem cell transplant (PBSCT) will be carried out using etoposide (VP-16)+cyclophosphamide (CY)+total body irradiation (TBI). Briefly, the regimen will consists of etoposide (VP-16) at 1.8 g/m² i.v. constant infusion (c.i.v.) over 26 h as a single dose followed by cyclophosphamide (CY) at 60 mg/kg per day i.v. over 2 h for 3 days, followed by total body irradiation (TBI) at 300 cGy per day for the next 3 days.

To calculate the dose, ideal body weight or actual body weight, whichever is less, will be used. As previously mentioned, factors such as the state of the cancer patient, patient's age, prior treatment, as well as the type of institution where the procedure is conducted will all be taken into consideration when determining the precise conditioning regimen.

C. Plasmid Construction of CRISPR-Cas9 System Targeting CD33

The lentiCRISPR v2 containing inserts Cas9 and Puromycin resistance will be obtained from Addgene (Plasmid #52961) (Sanjana et al., *Nat Methods* (2014) (8):783). To clone the single guide RNA (sgRNA) CD33 guide sequence, the lentiCRISPR v2 will be cut and dephosporylated with FastDigest BsmBI and FastAP (Fermentas) at 37° C. for 2 hours. gRNA targeting CD33 will be designed using the online optimized design tool at crispr.mit.edu. Alternatively, gRNA will have a sequence depicted in FIG. 12 (SEQ ID NO: 11). CD33 gRNA oligonucleotides will be obtained from Integrated DNA Technologies (IDT), phosphorylated using polynucleotide kinase (Fermentas) at 37° C. for 30 minutes and annealed by heating to 95° C. for 5 minutes and cooling to 25° C. at 1.5° C./minute. T7 ligase will be used to anneal the oligos, after which the annealed oligos will be ligated into gel purified vector (Qiagen) at 25° C. for 5 minutes. Resulting plasmid can then be amplified using an endotoxin-free midi-prep kit (Qiagen) (Sanjana et al., *Nat Methods* (2014)(8):783).

Alternatively, a two vector system may be used (where gRNA and Cas are expressed from separate vectors) protocol described previously (Mandal et al., *Cell Stem Cell* (2014) 15(5):643). Here, Mandal et al. achieved efficient ablation of genes in human hematopoietic stem cells using CRISPR-Cas system expressed from non-viral vectors.

Briefly, human-codon-optimized Cas9 gene containing a C-terminal SV40 nuclear localization signal will be cloned into a CAG expression plasmid with 2A-GFP. To direct Cas9 to cleave CD33 sequences of interest, the guide RNA (gRNA (SEQ ID. NO. 11)) will be separately expressed from a plasmid containing the human U6 polymerase III promoter. gRNA sequence oligonucleotides will be obtained from Integrated DNA Technologies (IDT), annealed, and introduced into the plasmid using BbsI restriction sites. Due to the transcription initiation requirement of a 'G' base for human U6 promoter, as well as the requirement for the PAM (protospacer-adjacent motif) sequence, genome target will comprise $GN_{20}GG$ nucleotide sequence.

In addition to infusing patients with CD33 depleted hematopoietic stem cells HSCs, a protocol will be developed in which the patients are subsequently infused with CD45RA depleted HSCs. Alternatively, the inventors will generate CD34CD33-CD4SRA cells using CRISPR-Cas9 system to reduce both CD33 and CD45RA genes simultaneously. Example guide RNA sequences for CD45RA and CD33 are shown in Tables 4 and 5).

D. Transfection of CD34+ Cells HSCs to Generate CD34+ CD33− Cell

Freshly isolated peripheral blood-derived CD34+ cells (from step 4) will be seeded at $1\times10^6$ cells/ml in serum-free CellGro SCGM Medium in the presence of cells culture grade Stem Cell Factor (SCF) 300 ng/ml, FLT3-L 300 ng/ml, Thrombopoietin (TPO) 100 ng/ml and IL-3 60 ng/ml. Following 24 hour of pre-stimulation, CD34+ HSCs will be transfected with LentiCRISPR v2 containing Cas9 and CD33 gRNA using Amaxa Human CD34 cell Nucleofector kit (U-008) (#VPA-1003) (Mandal et al., *Cell Stem Cell* (2014) 15(5):643). 24-48 hours post-transfection, CD34+ CD33− cells are selected with 1.2 µg/ml puromycin. Following the puromycin selection, CD34+CD33− cells will be maintained in puromycin-free media for couple of days.

E. Reinfusion of CD34+CD33+ Cells into the Patient

CD34+ cells transfected ex vivo with CRISPR-Cas9-CD33 (CD34+CD33− cells) are immediately reinfused through a Hickman catheter using a standard blood administration set without a filter (Hacein-Bey Abina et al. *JAMA* (2015) 313(15): 1550.

Generally, patients who have undergone the above outlined treatment protocol will be monitored for the reappearance of circulating blasts and cytopenias. Additionally, depending on the underlying mechanism of AML in a specific patient, the success of the treatment will be monitored by testing for reappearance of an informative molecular or cytogenetic marker, or an informative flow cytometry pattern. For example, reemergence of a BCR-ABL signal in Philadelphia chromosome-positive AML will be detected using fluorescent in situ hybridization (FISH) with probes for BCR (on chromosome 22) and ABL (on chromosome 9).

To evaluate the success of CD33 deletion via CRISPR-Cas9 system, peripheral blood CD34+ cells will be isolated from patients (post-transplant) and assessed for the CD33 expression, for example using flow cytometry, Western blotting, or immunohistochemistry.

As described herein, the HSCT described in this Example can be either autologous or allogeneic, and both approaches are suitable and can be incorporated in the methods described in the present disclosure.

III. Optional Step: Continued Treatment of a Patient with a CD33 Antibody Attached to a Toxin A. Treatment of Patients with CD33 Immunotoxin Gemtuzumab Ozogamicin (GO)

Figure 8:
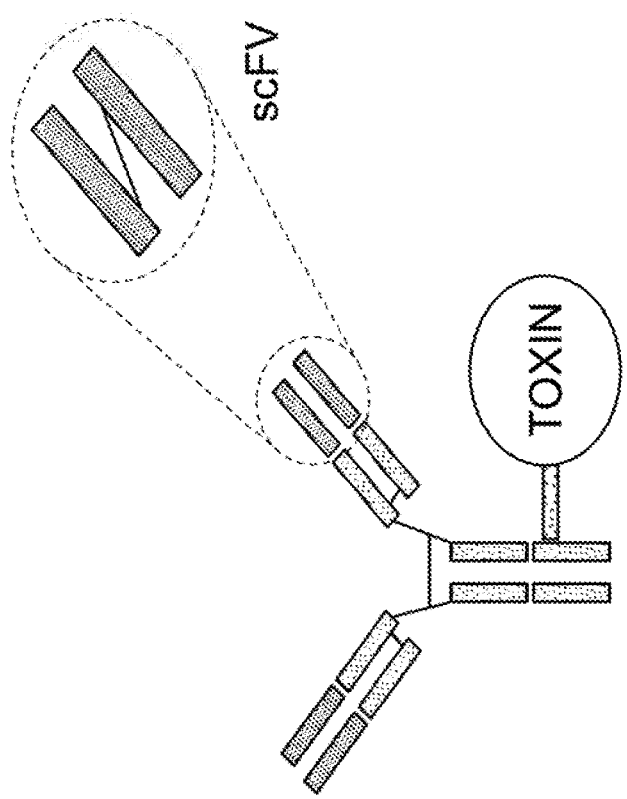
FIG. 8 is a schematic of an immunotoxin.

Patients will be treated with 9 mg/m$^2$ of anti-CD33 antibody gemtuzumab ozogamicin (GO) as a 2-hour intravenous infusion in 2 doses separated by 2 weeks (Larson et al., *Cancer* (2005), 104(7); 1442-52). GO is comprised of a humanized monoclonal antibody against CD33 which is conjugated with a cytostatic agent, calicheamicin (FIG. 8).

Alternatively, the anti-CD33 antibodies may be conjugated to different toxins, such as diphtheria toxin, *Pseudomonas* exotoxin A (PE), or ricin toxin A chain (RTA) can be generated (Wayne et al., *Blood* (2014) 123(16): 2470). Similarly, anti-CD45RA antibodies may be attached to a toxin and included in the treatment regimen.

Example 4: T Cells and NK Cell Lines Expressing an Anti-CD33 Chimeric Receptor Induce Cell Death of Target Cells Expressing CD33

Binding of Chimeric Receptors to CD33

Figure 9A:
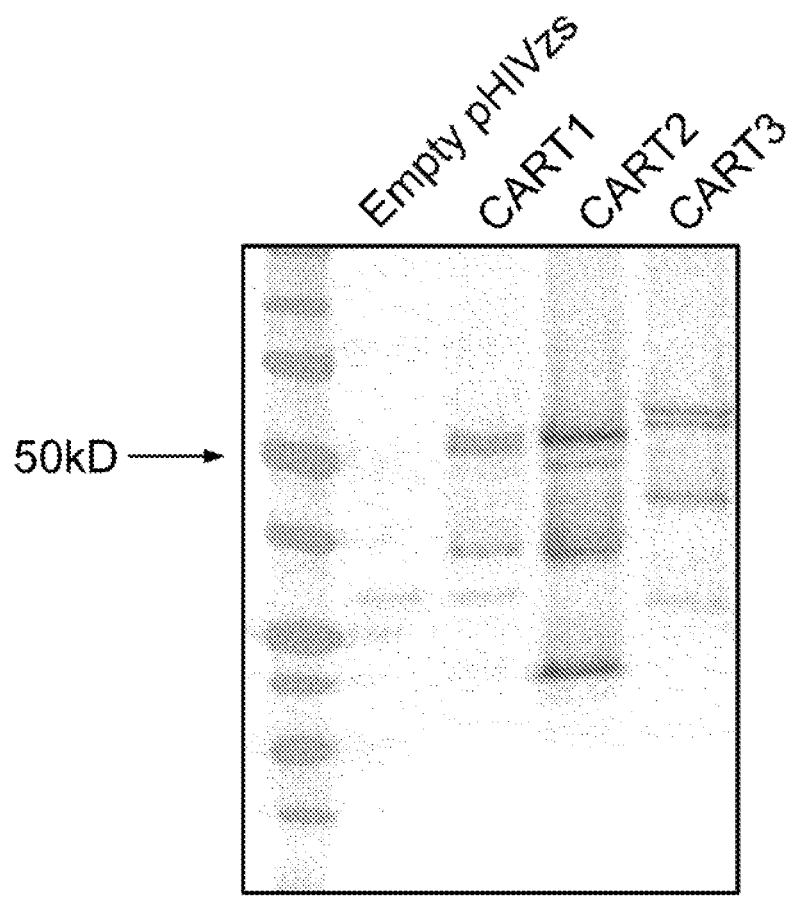
FIGS. 9A-9B show expression of anti-CD33 chimeric receptors expressed in K562 cells transduced with an empty vector or vector encoding an anti-CD33 chimeric receptor.
Figure 9B:
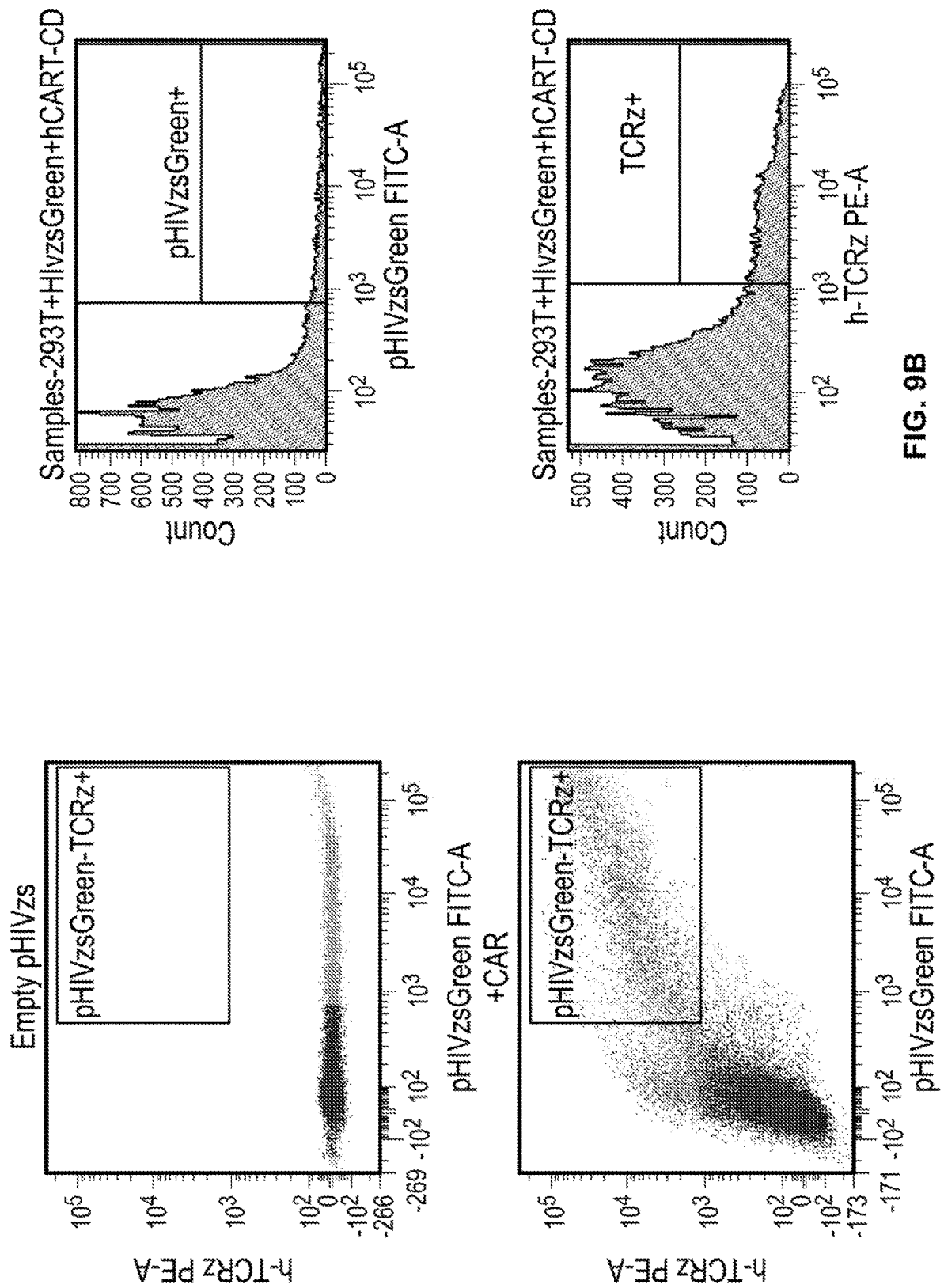

Chimeric receptors that bind CD33 (e.g., CART1, CART2, CART3) were generated using convention recombinant DNA technologies and inserted into a pHIV-Zsgreen vector (Addgene Cambridge, Mass.). The vectors containing the chimeric receptors were used to generate lentiviral particles, which were used to transduce different cell types, for example T cell lines (e.g., 293 T cells) and NK cell lines (e.g., NK92 cells). Expression of the chimeric receptors was detected by Western blotting (FIG. 9, panel A) and flow cytometry (FIG. 9, panel B).

Figure 10A:
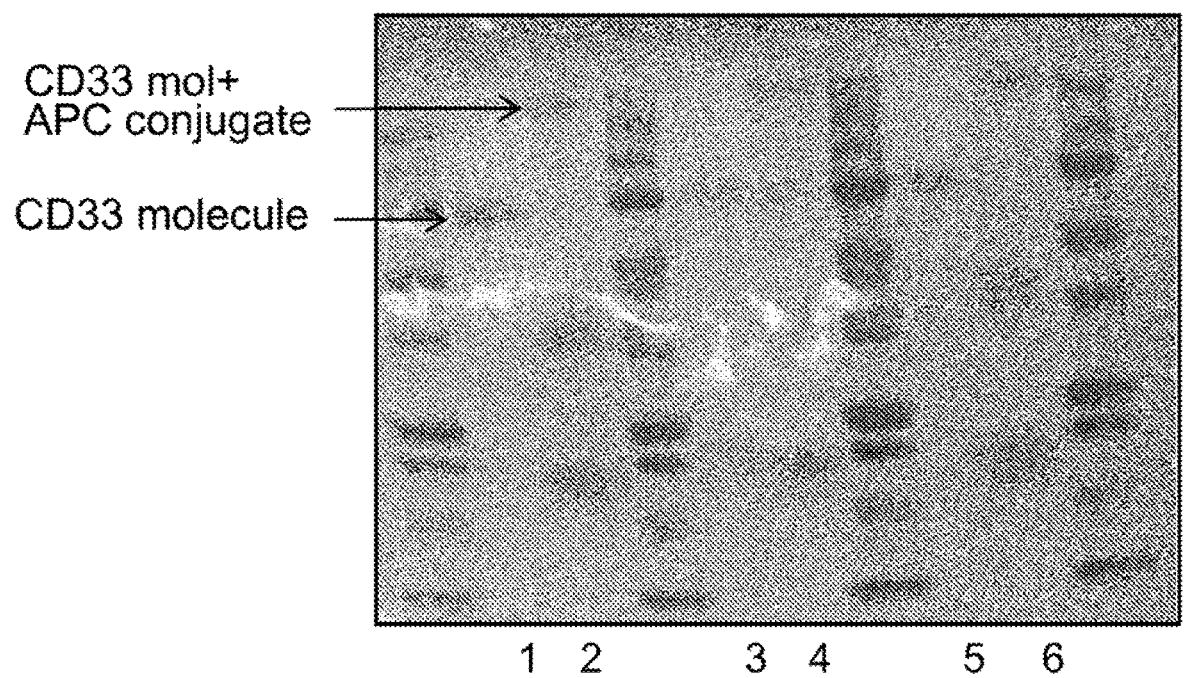
Figure 10B:
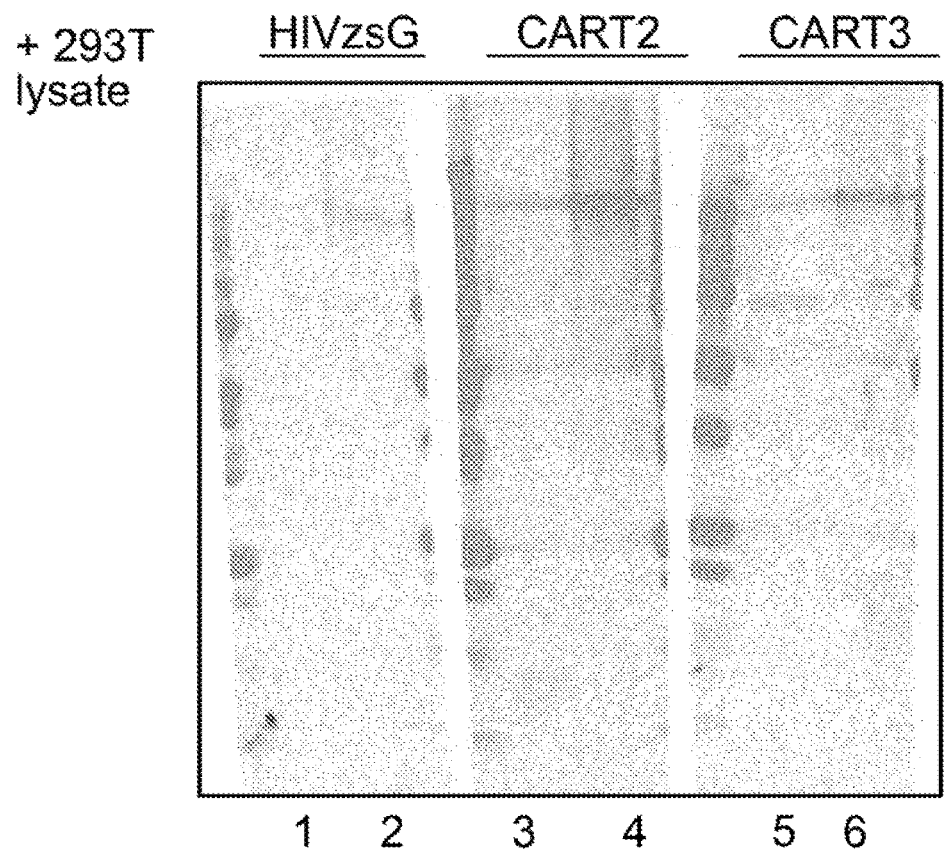

Cells expressing the chimeric receptors were selected by fluorescence-activated cell sorting (FACS) and assessed for their ability to bind CD33. Briefly, lysates of 293T cells expressing the chimeric receptors were coincubated with CD33 or CD33-allophycocyanin (APC) conjugate. The samples were subjected to protein electrophoresis and either stained with Ponceau protein stain (FIG. 10, panel A) or transferred to a membrane and probed with an anti-CD3ζ primary antibody (FIG. 10, panel B). In both cases, binding between the chimeric receptors and their target, CD33.

K562 cells expressing the chimeric receptors were also assessed for binding to CD33 by flow cytometry using CD33 as a probe (FIG. 10, panel C). There was an increase in the number of cells positive for expression of the chimeric receptor (CART1, CART2, or CART3) and CD33 binding as compared to cells containing an empty vector control, indicating the chimeric receptors bind to CD33.

Cytotoxicity Induced by Cells Expressing the Chimeric Receptors

Figure 11A:
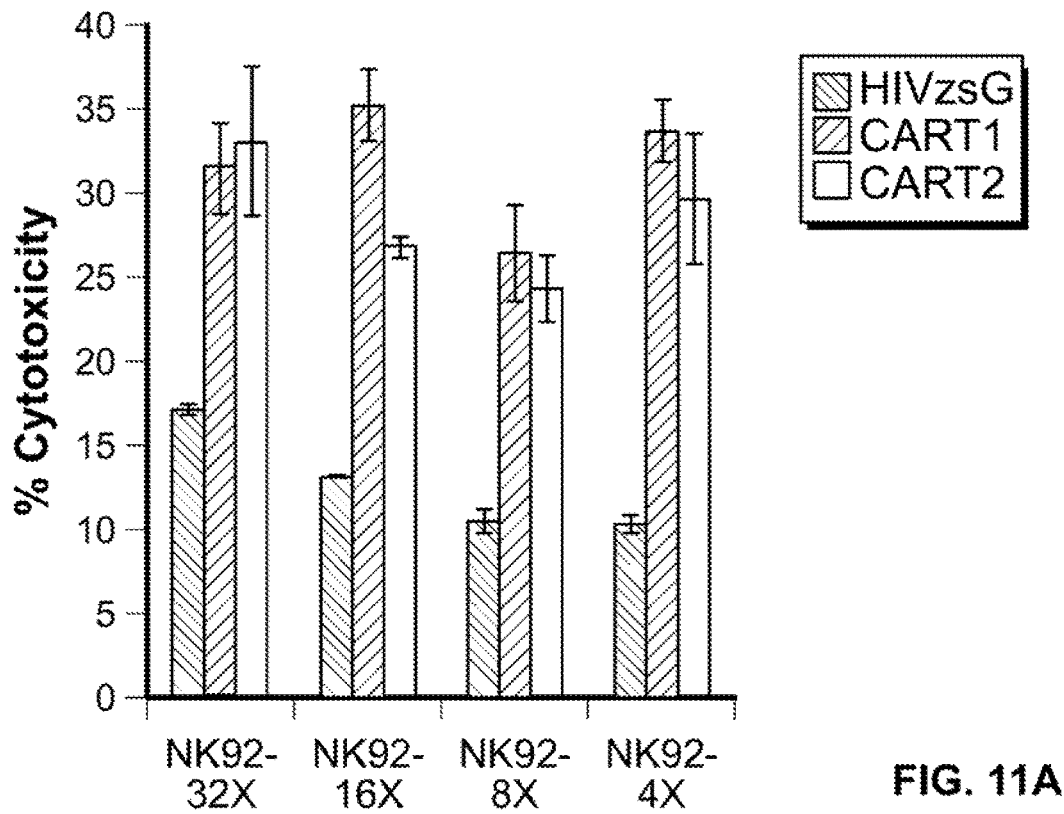
FIGS. 11A-11B show cytotoxicity of K562 cells by NK92 cells expressing the indicated chimeric receptors.
Figure 11B:
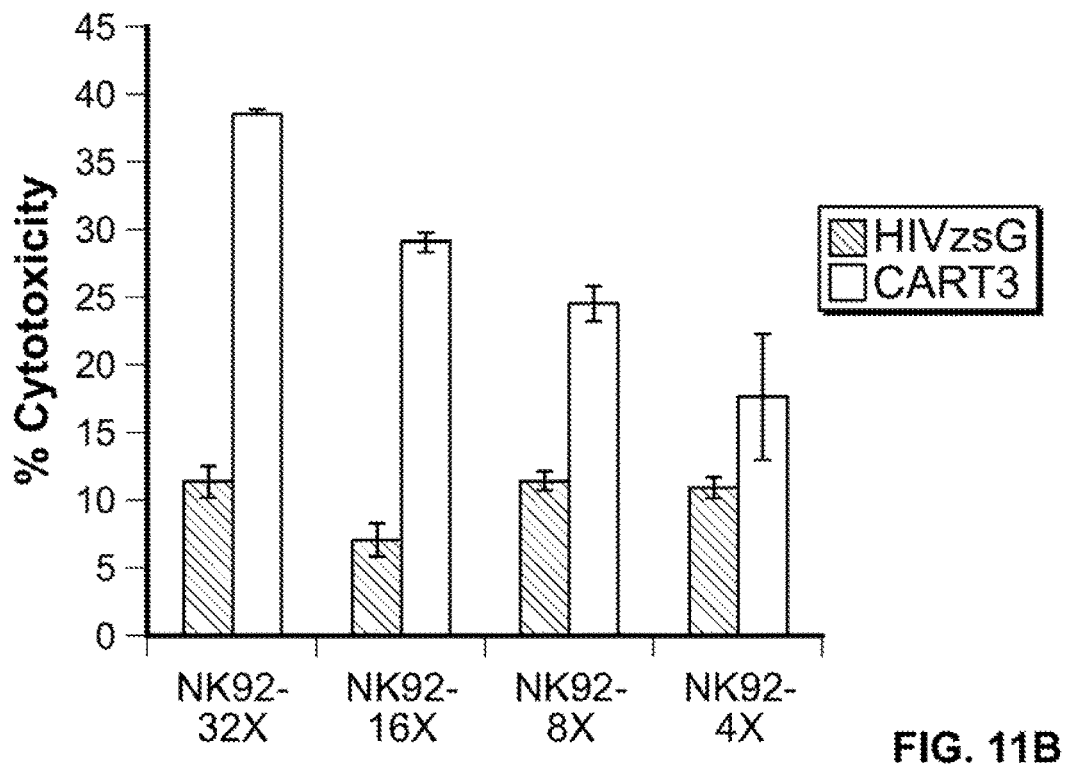

NK-92 cells expressing the chimeric receptors were functionally characterized for the ability to induce cytotoxicity of target cells presenting CD33 on the cell surface (e.g., KS62 are a human chronic myelogenous leukemia cell line that are CD33+). To perform the cytotoxicity assays, effector cells (immune cells, such as NK-92 cells) were infected with lentivirus particles encoding the chimeric receptors and expanded. Seven days post infection, cells expressing the chimeric receptors were selected by FACS analysis by selecting for fluorescent markers also encoded by the chimeric receptor encoding vector (e.g., GFP+ or Red+). The selected cells that express the chimeric receptors were expanded for one week. Fourteen days post infection, the cytotoxicity assay was performing involving staining the target cells (cells expressing the target cell-surface lineage-specific antigen, CD33) with carboyxfluorescein succinimidyl ester (CFSE) and counting both the target cells and cells expressing the chimeric receptors. Different ratios of target cells and cells expressing the chimeric receptors were coincubated in round bottom 96-well plates for 4.5 hrs, after which 7-aminoactinomycin D (7-AAD) was added to stain non-viable cells. Flow cytometry was performed to enumerate the population of viable and non-viable target cells. As shown in FIG. 11, panels A and B, NK92 cells expressing chimeric receptors CART1, CART2, or CART3 induced a substantial amount of cell death of target K562 cells at each of the cell ratios assessed.

Figure 12A:
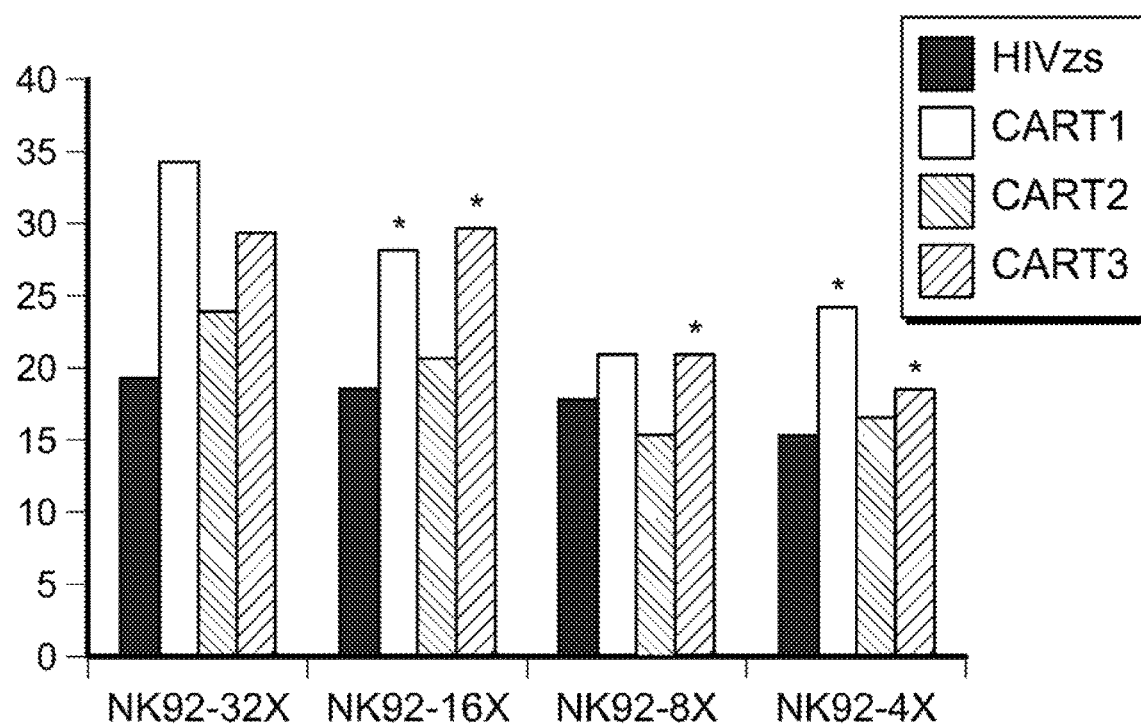
FIGS. 12A-12B show cytotoxicity (expressed as percent cytotoxicity on the y-axis) of K562 cells deficient in CD33 by NK92 cells expressing the indicated chimeric receptors.
Figure 12B:
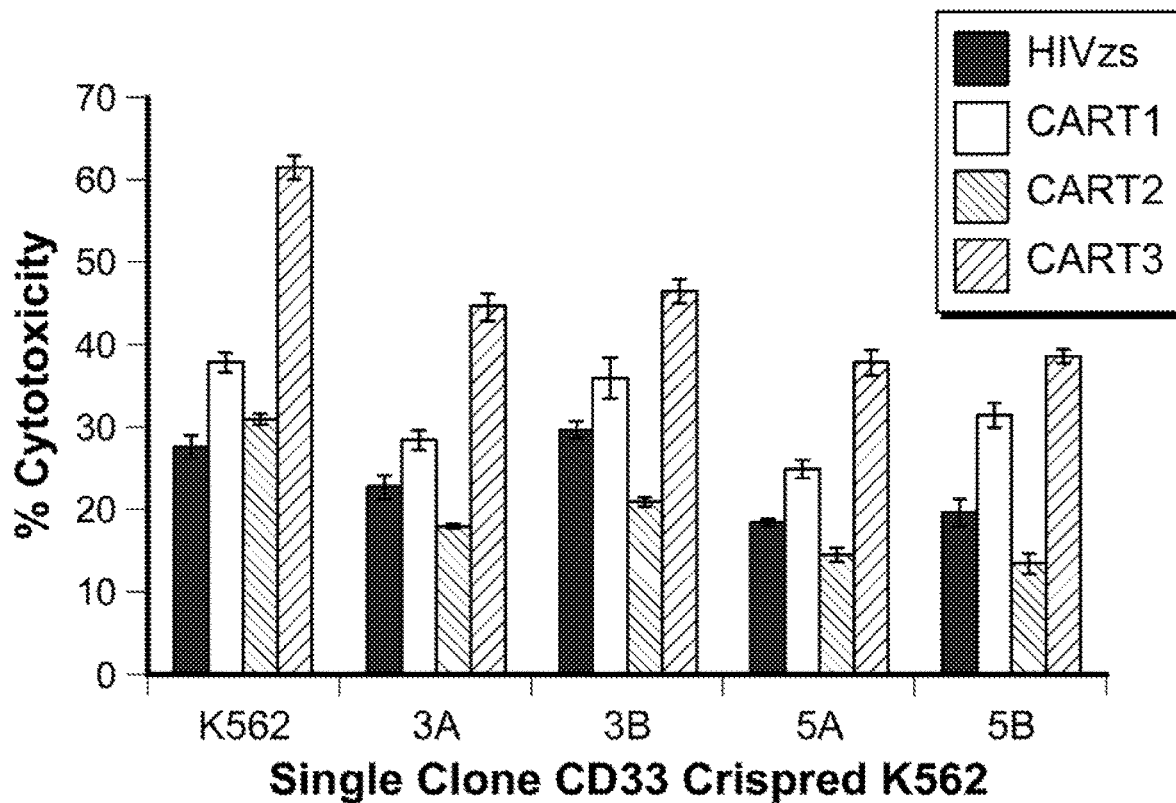

To determine that the cell death of K562 cells was dependent on specific targeting of the chimeric receptor to CD33. K562 were genetically engineered to be deficient in CD33 using a CRISPR/Cas system. Briefly, a human codon-optimized Cas9 endonuclease and a gRNA targeting a portion of the IgC domain of CD33 were expressed in the KS562 cells, resulting in populations of CD33-deficient K562 cells. The cells were expanded and co-incubated with NK92 cells expressing the chimeric receptors, and the cytotoxicity assay was performed as described above. As shown in FIG. 12 panel A, the pooled CD33-deficient K562 cells showed a modest reduction in cell death with co-incubated with the NK92 cells expressing the chimeric receptors. However, when single clones of CD33-deficient K562 cells were isolated, expanded, and used to perform the cytotoxicity assays, a more significant reduction in cytotoxicity was observed (FIG. 12, panel B).

Expression of Chimeric Receptors in Primary T Cells

Figure 13A:
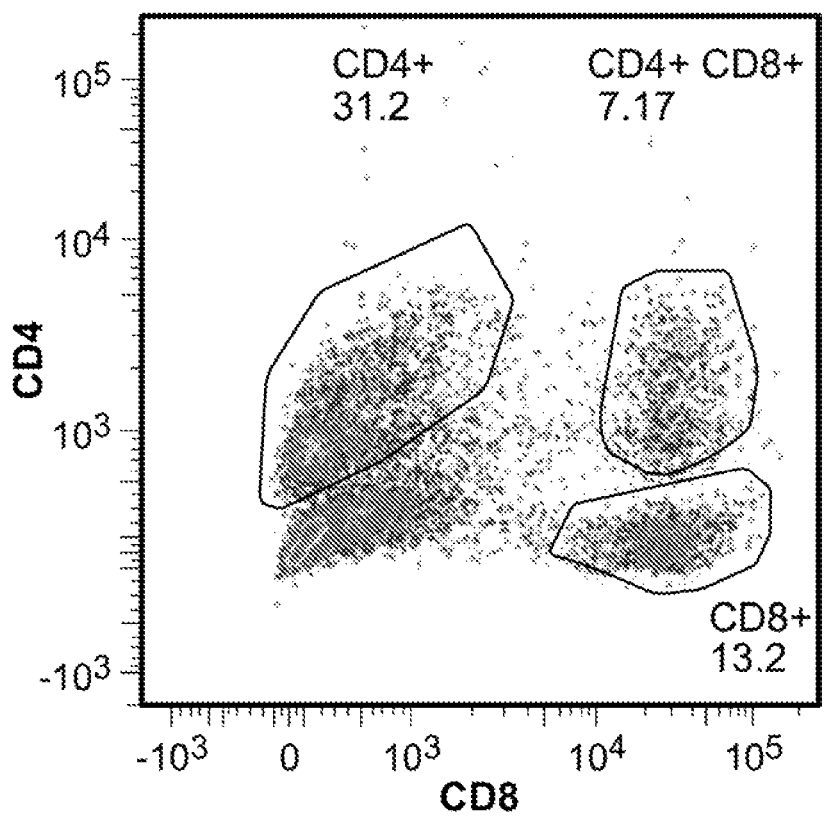
FIGS. 13A-13B show flow cytometric analysis of primary T cell populations.
Figure 13B:
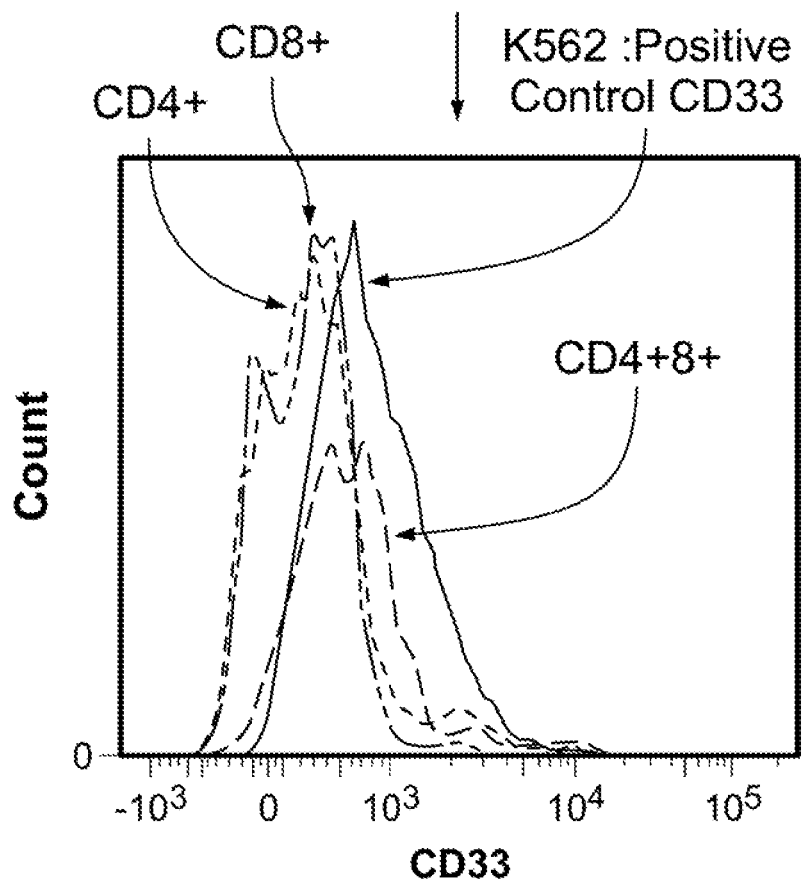
Figure 14A:
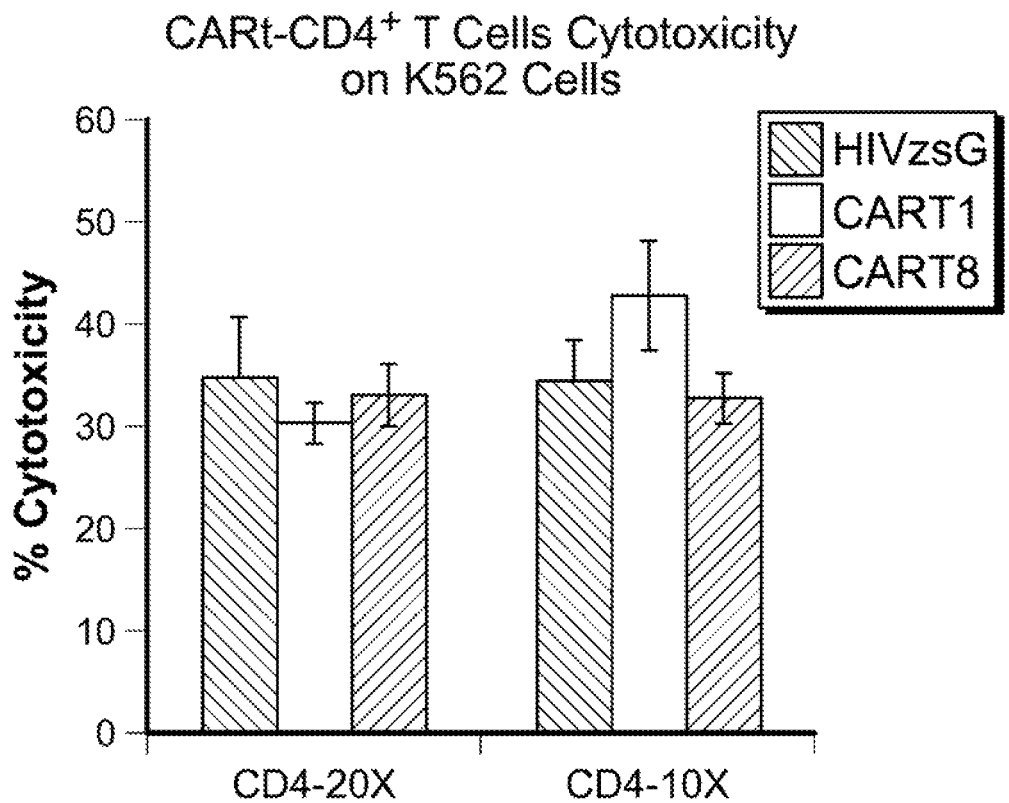
FIGS. 14A-14B show cytotoxicity of K562 cells by primary T cells expressing the indicated chimeric receptors.
Figure 14B:
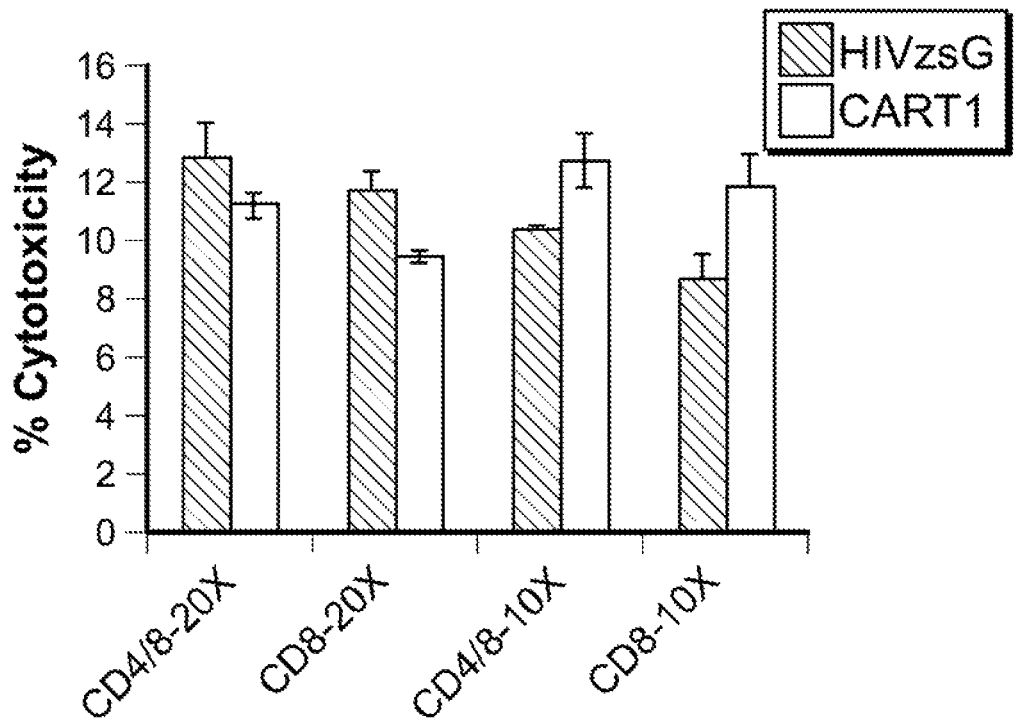

Primary T cell populations were isolated from PMBCs obtained from donors by FACS by positively selecting CD4+, CD8+, or CD4+/CD8+ cells, resulting in highly pure populations (FIG. 13, panels A and B). Each of the populations of primary T cells (CD4+, CD8+, or CD4+/CD8+ cells) were transduced with a lentiviral vector containing the chimeric receptors (e.g., CART1 and CART8) and the resulting primary T cells expressing chimeric receptors were used to perform cytotoxicity assays, as described above. Co-incubation of the population of CD4+ T cells expressing the chimeric receptors with K562 (1000 target K562 cells) did not result in cytotoxicity of the KS62 cells (FIG. 14, panel A). In contrast, in a cytotoxicity assay using either CD8+ or CD4+/CD8+ cells expressing the chimeric receptors and 1000 target K562 cells, the CD8+ or CD4+/CD8+ cells were able to induce cell death of the K562 cells at a low cellular ratio (FIG. 14, panel B).

Genetic Engineering Human Hematopoietic Stem Cells

Figure 15:
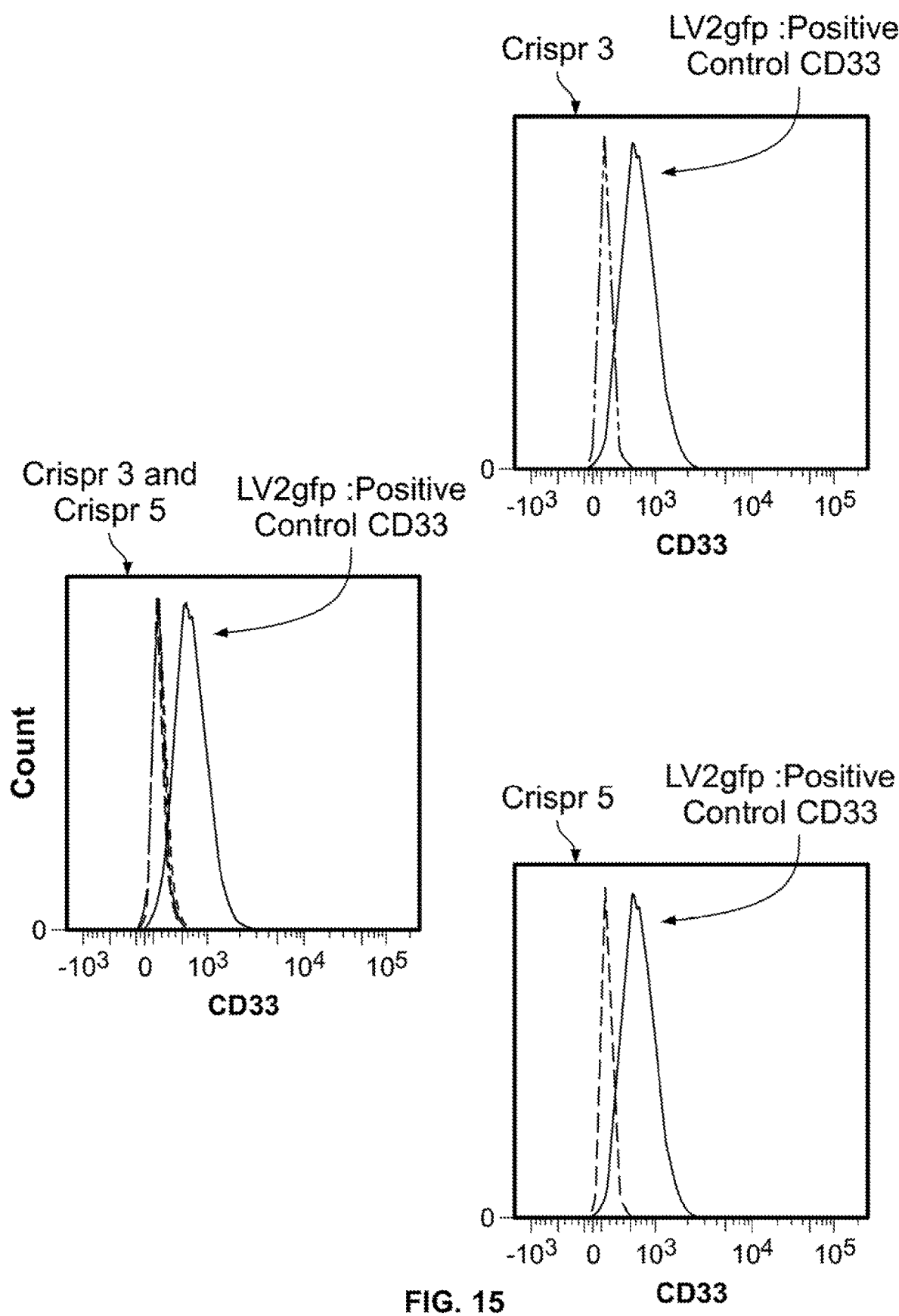
FIG. 15 shows flow cytometric analysis of CD33 editing in K562 cells using the CRISPR/Cas9 system and two different gRNAs (Crispr3, right top panel, and Crispr5, right bottom panel).

Several gRNAs were designed to hybridize to the IgC domain of CD33 (see, for example, Table 4, SEQ ID NO: 11 or 28-31). Each of the gRNAs were expressed along with a Cas9 endonuclease in K562 cells. The expression of CD33 was assessed by flow cytometry (FIG. 15). As shown for Crispr 3 (SEQ ID NO: 28) and Crispr5 (SEQ ID NO: 29), a significant reduction in CD33 was found in cells expressing the CD33-targeting CRISPR/Cas system, as compared to control cells expressing CD33.

Figure 16A:
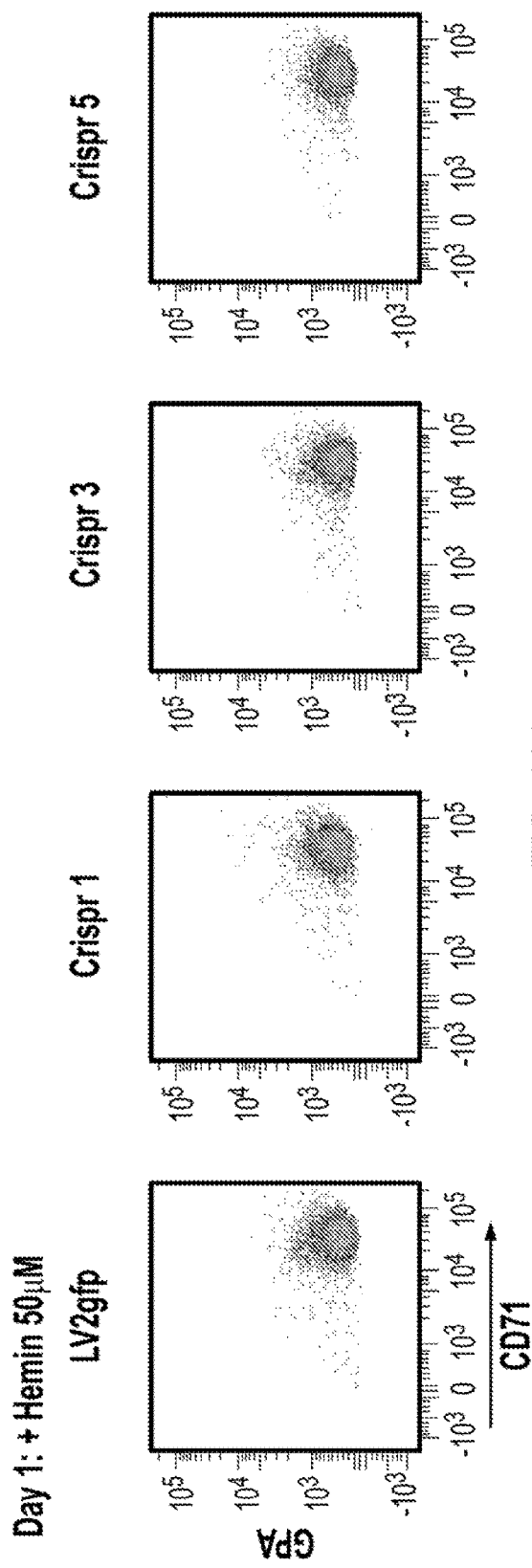
FIGS. 16A-16C show K562 cells deficient in CD33 present normal cell proliferation and erythropoeitic differentiation.
Figure 16B:
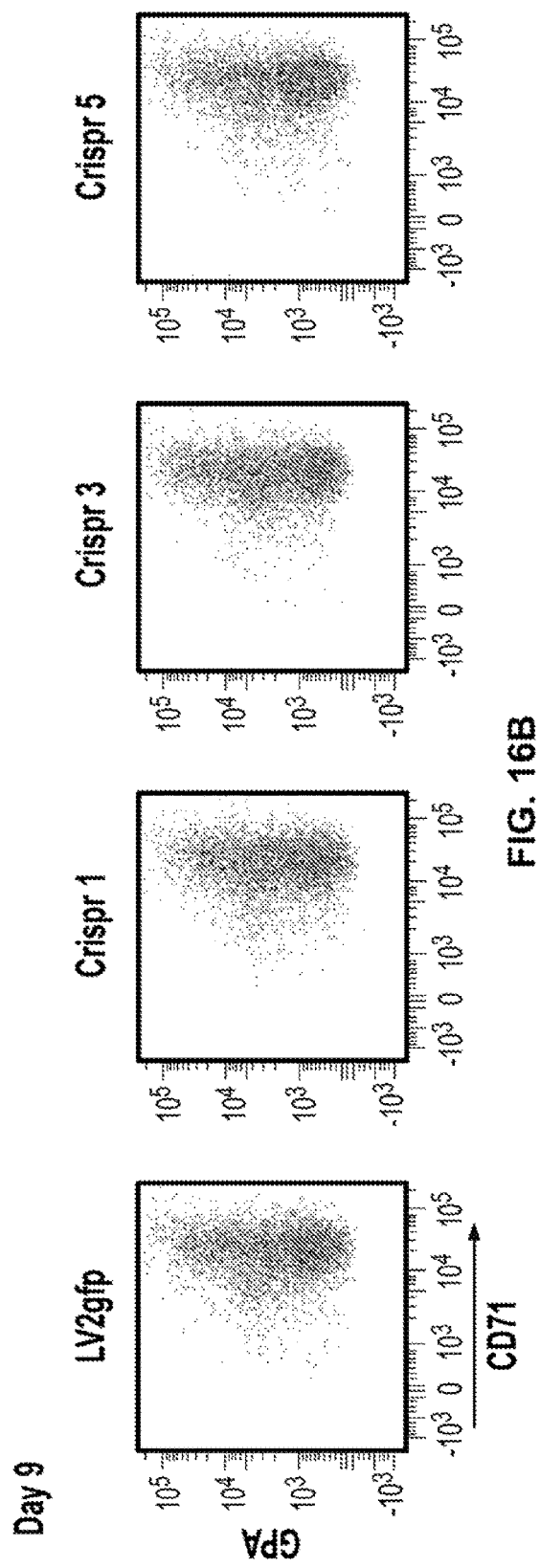
Figure 16C:
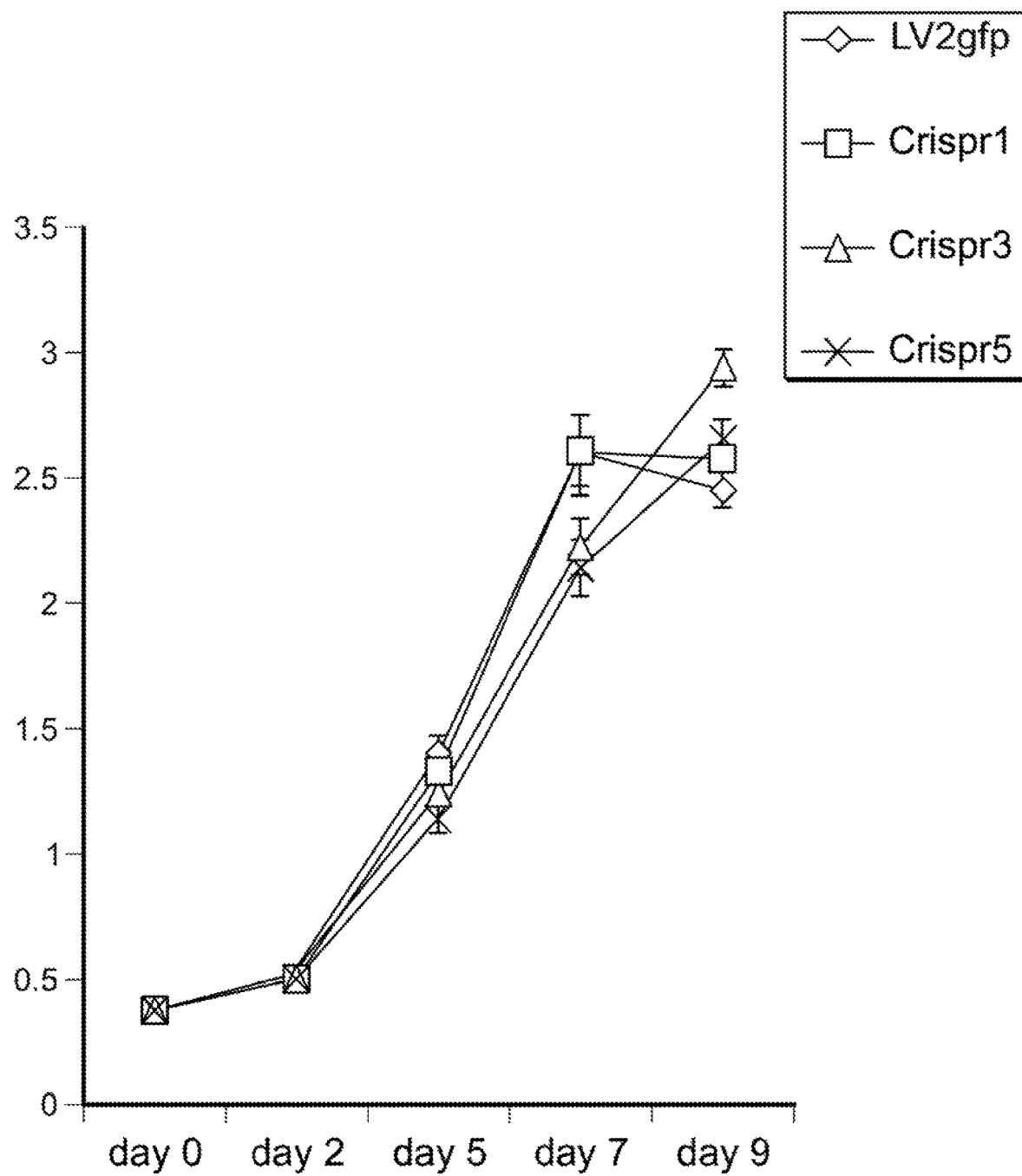
Figure 18:
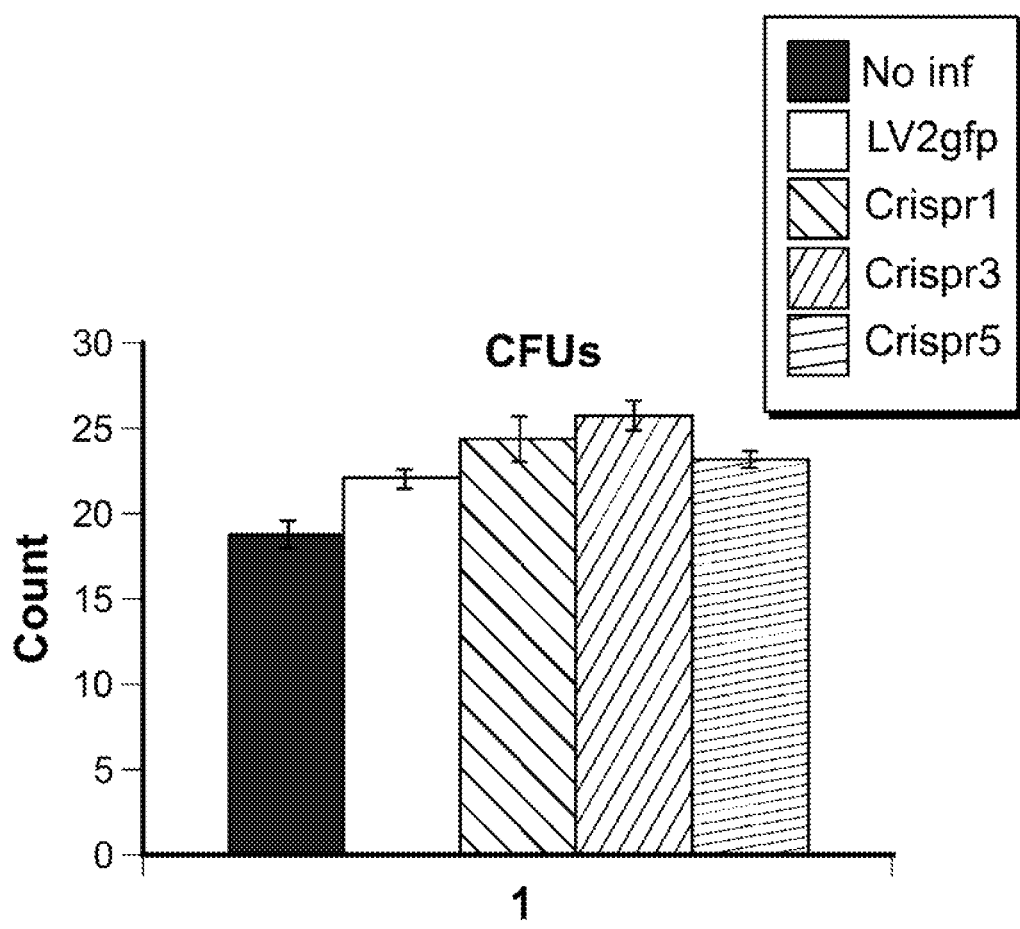
FIG. 18 shows colony formation for human CD34+/CD33" cells as compared to human CD34$^+$/CD33$^+$ cells. The columns, from left to right, correspond to no lentivirus infection, empty vector control, crispr1, crispr3, and crispr5.

The CD33-deficient hematopoietic stem cells were also assessed for various characteristics, including proliferation, erythopoeitic differentiation, and colony formation. Briefly, CD33-deficient hematopoietic stem cells and control cells were induced to differentiate by exposing the cells to hemin, and CD71, a marker of erythroid precursors, was assessed by flow cytometry at different time points (FIG. 16, panels A and B). CD33-deficient hematopoietic stem cells underwent erythopoeitic differentiation and flow cytometric profiles appeared similar to the control cells (CD33+). The cells were also subjected to MTT assay to measure the metabolic activity of the CD33-deficient hematopoietic stem cells. As shown in FIG. 16, panel C, the CD33-deficient hematopoietic stem cells performed comparably to the control cells. Finally, the ability of the cells to proliferate and form colonies of cells was observed using a microscopic colony formation assay. Again, the CD33-deficient hematopoietic stem cells were able to form colonies to a similar extents as the control cells (FIG. 18). These results indicate the CRISPR/Cas deletion of a portion of CD33 does not significantly impact the ability of the cells to proliferate, differentiate, or form colonies.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one of skill in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of treating a hematopoietic malignancy in a subject in need thereof, the method comprising
   (i) administering to the subject an effective amount of a population of genetically engineered human hematopoietic cells, wherein the hematopoietic cells are engineered such that they are deficient in a lineage-specific cell-surface antigen which is expressed by their naturally-occurring hematopoietic cell counterpart.

2. The method of claim 1, wherein the lineage-specific cell-surface antigen is an antigen that is naturally associated with human leukocytes, a subpopulation of human leukocytes, human myeloid cells, or human plasma cells.

3. The method of claim 1, wherein the lineage-specific cell-surface antigen is a cluster of differentiation (CD) antigen.

4. The method of claim 3, wherein the CD antigen is selected from the group consisting of CD19, CD13, CD20, CD22, CD38, CD123, CD33, CD45, CD70, CD312, CD191, CD85D, CD117, CD96, and CD269.

5. The method of claim 4, wherein the CD antigen is CD33 or CD19.

6. The method of claim 1, wherein the population of genetically engineered human hematopoietic cells comprises human hematopoietic cells selected from the group consisting of a hematopoietic stem cell, a progenitor cell, a myeloid progenitor cell, a lymphoid progenitor cell, a myeloid cell, a lymphoid cell, and any combination(s) thereof.

7. The method of claim 1, wherein the population of genetically engineered human hematopoietic cells comprises hematopoietic stem cells.

8. The method of claim 1, wherein the human hematopoietic cell is obtained from bone marrow, blood, umbilical cord, or peripheral blood mononuclear cells (PBMCs) of a human subject.

9. The method of claim 1, wherein an endogenous gene encoding the lineage-specific cell-surface antigen is engineered using genome editing.

10. The method of claim 9, wherein the whole or a portion of the endogenous gene encoding the lineage-specific cell-surface antigen is deleted.

11. The method of claim 9, wherein the level of the lineage-specific cell-surface antigen is reduced as compared with the level of the lineage-specific cell-surface antigen expressed by its naturally-occurring hematopoietic cell counterpart.

12. The method of claim 9, wherein the genome editing is a CRISPR system.

13. The method of claim 12, wherein the CRISPR system comprises a guide nucleic acid that hybridizes to a coding or non-coding sequence of the endogenous gene encoding the lineage-specific cell-surface antigen.

14. The method of claim 12, wherein the CRISPR system cleaves or produces an insertion, deletion and/or substitution of one or more nucleotides in a coding region or a non-coding region of an endogenous gene encoding the lineage-specific cell-surface antigen.

15. The method of claim 14, wherein the lineage-specific cell-surface antigen is CD33 or CD19.

16. The method of claim 1, further comprising (ii) administering to the subject an effective amount of an agent that targets the lineage-specific cell-surface antigen that is deficient in the hematopoietic cells, wherein the agent comprises an antigen-binding fragment that binds said lineage-specific cell-surface antigen.

17. The method of claim 16, wherein the agent is an antibody or antibody fragment selected from the group consisting of a monoclonal antibody, fully human antibody, humanized antibody, chimeric antibody, single-chain antibody, bi-specific antibody, and a F(ab')2 fragment.

18. The method of claim 16, wherein the agent is an immune cell expressing a chimeric receptor that comprises said antigen-binding fragment.

19. The method of claim 18, wherein the immune cell expressing a chimeric receptor is a T cell and wherein the antigen-binding fragment binds CD33 or CD19.

20. The method of claim 16, wherein the hematopoietic malignancy is selected from the group consisting of Hodgkin's lymphoma, non-Hodgkin's lymphoma, leukemia, acute myeloid leukemia, chronic myelogenous leukemia, acute lymphoblastic leukemia, chronic lymphoblastic leukemia, and multiple myeloma.

* * * * *

SEQUENCE LISTING

```
<160> NUMBER OF SEQ ID NOS: 47

<210> SEQ ID NO 1
<211> LENGTH: 339
<212> TYPE: DNA
<213> ORGANISM: Homo sapiens

<400> SEQUENCE: 1
gagatcgtgc tgacccagag ccccggcagc ctggccgtga gccccggcga gagggtgacc      60
atgagctgca agagcagcca gagcgtgttc ttcagcagca gccagaagaa ctacctggcc     120
tggtaccagc agatccccgg ccagagcccc aggctgctga tctactgggc cagcaccagg     180
gagagcggcg tgcccgacag gttcaccggc agcggcagcg gcaccgactt cacccctgacc    240 atcagcagcg tgcagcccga ggacctggcc atctactact gccaccagta cctgagcagc     300
aggaccttcg gccagggcac caagctggag atcaagagg                            339

<210> SEQ ID NO 2
<211> LENGTH: 354
<212> TYPE: DNA
<213> ORGANISM: Homo sapiens

<400> SEQUENCE: 2
caggtgcagc tgcagcagcc cggcgccgag gtggtgaagc ccggcgccag cgtgaagatg      60
agctgcaagg ccagcggcta caccttcacc agctactaca tccactggat caagcagacc    120
cccggccagg gcctggagtg ggtgggcgtg atctaccccg gcaacgacga catcagctac    180
aaccagaagt tccagggcaa ggccaccctg accgccgaca gagcagcac caccgcctac     240 atgcagctga gcagcctgac cagcgaggac agcgccgtgt actactgcgc cagggaggtg    300
aggctgaggt acttcgacgt gtggggccag ggcaccaccg tgaccgtgag cagc          354

<210> SEQ ID NO 3
<211> LENGTH: 657
<212> TYPE: DNA
<213> ORGANISM: Homo sapiens

<400> SEQUENCE: 3
attgaagtta tgtatcctcc tccttaccta gacaatgaga agagcaatgg aaccattatc      60
catgtgaaag ggaaacacct ttgtccaagt cccctatttc ccggaccttc taagcccttt    120
```

```
tgggtgctgg tggtggttgg tggagtcctg gcttgctata gcttgctagt aacagtggcc    180
tttattattt tctgggtgag gagtaagagg agcaggctcc tgcacagtga ctacatgaac    240
atgactcccc gccgcccggg gcccacccgc aagcattacc agccctatgc cccaccacgc    300
gacttcgcag cctatcgctc cagagtgaag ttcagcagga gcgcagacgc ccccgcgtac    360
cagcagggcc agaaccagct ctataacgag ctcaatctag gacgaagaga ggagtacgat    420
gttttggaca agagacgtgg ccgggaccct gagatggggg aaagccgag aaggaagaac    480 cctcaggaag gcctgtacaa tgaactgcag aaagataaga tggcggaggc ctacagtgag    540
attgggatga aggcgagcg ccggaggggc aaggggcacg atggccttta ccagggtctc    600
agtacagcca ccaaggacac ctacgacgcc cttcacatgc aggccctgcc cctcgc       657

<210> SEQ ID NO 4
<211> LENGTH: 603
<212> TYPE: DNA
<213> ORGANISM: Homo sapiens

<400> SEQUENCE: 4
ctatcaattt ttgatcctcc tccttttaaa gtaactctta caggaggata tttgcatatt     60
tatgaatcac aactttgttg ccagctgaag ttctggttac ccataggatg tgcagccttt    120
gttgtagtct gcattttggg atgcatactt atttgttggc ttacaaaaaa gaagtattca    180
tccagtgtgc acgaccctaa cggtgaatac atgttcatga gagcagtgaa cacagccaaa    240
aaatctagac tcacagatgt gaccctaaga gtgaagttca gcaggagcgc agacgccccc    300
gcgtaccagc agggccagaa ccagctctat aacgagctca atctaggacg aagagaggag    360
tacgatgttt tggacaagag acgtggccgg gaccctgaga tgggggaaa gccgagaagg    420 aagaaccctc aggaaggcct gtacaatgaa ctgcagaaag ataagatggc ggaggcctac    480
agtgagattg gatgaaagg cgagcgccgg aggggcaagg gcacgatgg cctttaccag    540 ggtctcagta cagccaccaa ggacacctac gacgcccttc acatgcaggc cctgccccct    600
cgc                                                                 603

<210> SEQ ID NO 5
<211> LENGTH: 627
<212> TYPE: DNA
<213> ORGANISM: Homo sapiens

<400> SEQUENCE: 5
attgaagtta tgtatcctcc tccttaccta gacaatgaga agagcaatgg aaccattatc     60
catgtgaaag ggaaacacct ttgtccaagt cccctatttc ccggaccttc taagcccttt    120
tgggtgctgg tggtggttgg tggagtcctg gcttgctata gcttgctagt aacagtggcc    180
tttattattt tctgggtgag gagtaagagg agcaggctcc tgcacagtga ctacatgttc    240
atgagagcag tgaacacagc caaaaaatct agactcacag atgtgaccct aagagtgaag    300
ttcagcagga gcgcagacgc ccccgcgtac cagcagggcc agaaccagct ctataacgag    360
ctcaatctag gacgaagaga ggagtacgat gttttggaca agagacgtgg ccgggaccct    420
gagatggggg aaagccgag aaggaagaac cctcaggaag gcctgtacaa tgaactgcag    480
aaagataaga tggcggaggc ctacagtgag attgggatga aggcgagcg ccggaggggc    540 aaggggcacg atggccttta ccagggtctc agtacagcca ccaaggacac ctacgacgcc    600
cttcacatgc aggccctgcc cctcgc                                        627
```

<210> SEQ ID NO 6
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 7
<211> LENGTH: 89
<212> TYPE: PRT
<213> ORGANISM: Artificial Sequence
<220> FEATURE:
<223> OTHER INFORMATION: Synthetic Polypeptide

<400> SEQUENCE: 7

Leu Ser Ile Phe Asp Pro Pro Pro Phe Lys Val Thr Leu Thr Gly Gly
1               5                   10                  15

Tyr Leu His Ile Tyr Glu Ser Gln Leu Cys Cys Gln Leu Lys Phe Trp
            20                  25                  30

Leu Pro Ile Gly Cys Ala Ala Phe Val Val Val Cys Ile Leu Gly Cys
        35                  40                  45

Ile Leu Ile Cys Trp Leu Thr Lys Lys Lys Tyr Ser Ser Ser Val His
    50                  55                  60

Asp Pro Asn Gly Glu Tyr Met Phe Met Arg Ala Val Asn Thr Ala Lys
65                  70                  75                  80

Lys Ser Arg Leu Thr Asp Val Thr Leu
                85

<210> SEQ ID NO 8
<211> LENGTH: 97
<212> TYPE: PRT
<213> ORGANISM: Artificial Sequence
<220> FEATURE:
<223> OTHER INFORMATION: Synthetic Polypeptide

<400> SEQUENCE: 8

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe

```
              50                  55                  60
Trp Val Arg Ser Lys Arg Ser Arg Leu Leu His Ser Asp Tyr Met Phe
 65                  70                  75                  80

Met Arg Ala Val Asn Thr Ala Lys Lys Ser Arg Leu Thr Asp Val Thr
                 85                  90                  95

Leu

<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 9
ccaaagagtc cggggatact tgg                                            23

<210> SEQ ID NO 10
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 10
gttgagtttt gcattggcgg cgg                                            23

<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 11
acctgtcagg tgaagttcgc tgg                                            23

<210> SEQ ID NO 12
<211> LENGTH: 118
<212> TYPE: PRT
<213> ORGANISM: Homo sapiens

<400> SEQUENCE: 12

Gln Val Gln Leu Gln Gln Pro Gly Ala Glu Val Val Lys Pro Gly Ala
  1               5                  10                  15

Ser Val Lys Met Ser Cys Lys Ala Ser Gly Tyr Thr Phe Thr Ser Tyr
                 20                  25                  30

Tyr Ile His Trp Ile Lys Gln Thr Pro Gly Gln Gly Leu Glu Trp Val
             35                  40                  45

Gly Val Ile Tyr Pro Gly Asn Asp Asp Ile Ser Tyr Asn Gln Lys Phe
 50                  55                  60

Gln Gly Lys Ala Thr Leu Thr Ala Asp Lys Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Val Arg Leu Arg Tyr Phe Asp Val Trp Gly Gln Gly Thr
            100                 105                 110

Thr Val Thr Val Ser Ser
            115
```

```
<210> SEQ ID NO 13
<211> LENGTH: 113
<212> TYPE: PRT
<213> ORGANISM: Homo sapiens

<400> SEQUENCE: 13
```

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg

```
<210> SEQ ID NO 14
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 14
```

Gly Ser Thr Ser Ser Gly Ser Gly Lys Pro Gly Ser Gly Glu Gly Ser
1               5                   10                  15

Thr Lys Gly

```
<210> SEQ ID NO 15
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 15
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 16
<211> LENGTH: 850
<212> TYPE: DNA
<213> ORGANISM: Artificial Sequence
<220> FEATURE:
<223> OTHER INFORMATION: Synthetic Polynucleotide

<400> SEQUENCE: 16

```
ggtgtcgtga gcggccgctg aactggccac catggacatg agggtccctg ctcagctcct      60
ggggctcctg ctgctctggc tctcaggtgc cagatgtgag atcgtgctga cccagagccc     120
cggcagcctg ccgtgagcc ccggcaagag ggtgaccatg agctgcaaga gcagccagag     180
cgtgttcttc agcagcagcc agaagaacta cctggcctgg taccagcaga tccccggcca     240
gagccccagg ctgctgatct actgggccag caccagggag agcggcgtgc ccgacaggtt     300
caccggcagc ggcagcggca gcggcaccga cttcaccctg accatcagca gcgtgcagcc     360
cgaggacctg gccatctact actgccacca gtacctgagc agcaggacct tcggccaggg     420
caccaagctg gagatcaaga ggggcagcac cagcggcagc ggcaagcccg gcagcggcga     480
gggcagcacc aagggccagg tgcagctgca gcagcccggc gccgaggtgg tgaagcccgg     540
cgccagcgtg aagatgagct gcaaggccag cggctacacc ttcaccagct actacatcca     600
ctggatcaag cagacccccg gccagggcct ggagtgggtg ggcgtgatct accccggcaa     660
cgacgacatc agctacaacc agaagttcca gggcaaggcc accctgaccg ccgacaagag     720
cagcaccacc gcctacatgc agctgagcag cctgaccagc gaggacagcg ccgtgtacta     780
ctgcgccagg gaggtgaggc tgaggtactt cgacgtgtgg ggccagggca ccaccgtgac     840
cgtgagcagc                                                           850
```

<210> SEQ ID NO 17
<211> LENGTH: 695
<212> TYPE: DNA
<213> ORGANISM: Artificial Sequence
<220> FEATURE:
<223> OTHER INFORMATION: Synthetic Polynucleotide

<400> SEQUENCE: 17

```
gcggccgcaa ttgaagttat gtatcctcct ccttacctag acaatgagaa gagcaatgga      60
accattatcc atgtgaaagg gaaacacctt tgtccaagtc ccctatttcc cggaccttct     120
aagccctttt gggtgctggt ggtggttggt ggagtcctgg cttgctatag cttgctagta     180
acagtggcct ttattatttt ctgggtgagg agtaagagga gcaggctcct gcacagtgac     240
tacatgaaca tgactccccg ccgcccggg cccacccgca agcattacca gcccctatgcc     300
ccaccacgcg acttcgcagc ctatcgctcc agagtgaagt tcagcaggag cgcagacgcc     360
cccgcgtacc agcagggcca gaaccagctc tataacgagc tcaatctagg acgaagagag     420
gagtacgatg ttttggacaa gagacgtggc cgggaccctg agatgggggg aaagccgaga     480
aggaagaacc ctcaggaagg cctgtacaat gaactgcaga agataagat ggcggaggcc     540
tacagtgaga ttgggatgaa aggcgagcgc cggaggggca aggggcacga tggcctttac     600
cagggtctca gtacagccac caaggacacc tacgacgccc ttcacatgca ggccctgccc     660
cctcgctaac gccctctcc ctccccccc cctaa                                 695
```

<210> SEQ ID NO 18
<211> LENGTH: 641
<212> TYPE: DNA
<213> ORGANISM: Artificial Sequence
<220> FEATURE:

<223> OTHER INFORMATION: Synthetic Polynucleotide

<400> SEQUENCE: 18

```
gcggccgcac tatcaattttt tgatcctcct ccttttaaag taactcttac aggaggatat      60
ttgcatatttt atgaatcaca actttgttgc cagctgaagt tctggttacc cataggatgt     120
gcagcctttg ttgtagtctg cattttggga tgcatactta tttgttggct tacaaaaaag     180
aagtattcat ccagtgtgca cgaccctaac ggtgaataca tgttcatgag agcagtgaac     240
acagccaaaa aatctagact cacagatgtg accctaagag tgaagttcag caggagcgca     300
gacgcccccg cgtaccagca gggccagaac cagctctata cgagctcaa tctaggacga      360
agagaggagt acgatgtttt ggacaagaga cgtggccggg accctgagat gggggggaaag     420
ccgagaagga agaaccctca ggaaggcctg tacaatgaac tgcagaaaga taagatggcg     480
gaggcctaca gtgagattgg gatgaaaggc gagcgccgga ggggcaaggg gcacgatggc     540
ctttaccagg gtctcagtac agccaccaag acacctacg acgcccttca catgcaggcc      600
ctgccccctc gctaacgccc ctctccctcc cccccccta a                          641
```

<210> SEQ ID NO 19
<211> LENGTH: 665
<212> TYPE: DNA
<213> ORGANISM: Artificial Sequence
<220> FEATURE:
<223> OTHER INFORMATION: Synthetic Polynucleotide

<400> SEQUENCE: 19

```
gcggccgcaa ttgaagttat gtatcctcct ccttacctag acaatgagaa gagcaatgga      60
accattatcc atgtgaaagg gaaacacctt tgtccaagtc cctatttcc cggaccttct      120
aagccctttt gggtgctggt ggtgttggt ggagtcctgg cttgctatag cttgctagta      180
acagtggcct ttattatttt ctgggtgagg agtaagagga gcaggctcct gcacagtgac     240
tacatgttca tgagagcagt gaacacagcc aaaaaatcta gactcacaga tgtgacccta     300
agagtgaagt tcagcaggag cgcagacgcc cccgcgtacc agcagggcca gaaccagctc     360
tataacgagc tcaatctagg acgaagagag gagtacgatg ttttggacaa gagacgtggc     420
cgggaccctg agatgggggg aaagccgaga aggaagaacc ctcaggaagg cctgtacaat     480
gaactgcaga agataagat ggcggaggcc tacagtgaga ttgggatgaa aggcgagcgc      540
cggagggggca aggggcacga tggcctttac cagggtctca gtacagccac caaggacacc     600
tacgacgccc ttcacatgca ggccctgccc cctcgctaac gcccctctcc ctcccccccc     660
cctaa                                                                 665
```

<210> SEQ ID NO 20
<211> LENGTH: 503
<212> TYPE: PRT
<213> ORGANISM: Homo sapiens

<400> SEQUENCE: 20

```
Met Trp Leu Gln Ser Leu Leu Leu Leu Gly Thr Val Ala Cys Ser Ile
1               5                   10                  15

Ser Glu Ile Val Leu Thr Gln Ser Pro Gly Ser Leu Ala Val Ser Pro
            20                  25                  30

Gly Glu Arg Val Thr Met Ser Cys Lys Ser Ser Gln Ser Val Phe Phe
        35                  40                  45

Ser Ser Ser Gln Lys Asn Tyr Leu Ala Trp Tyr Gln Gln Ile Pro Gly
    50                  55                  60
```

-continued

```
Gln Ser Pro Arg Leu Leu Ile Tyr Trp Ala Ser Thr Arg Glu Ser Gly
 65                  70                  75                  80

Val Pro Asp Arg Phe Thr Gly Ser Gly Ser Gly Thr Asp Phe Thr Leu
             85                  90                  95

Thr Ile Ser Ser Val Gln Pro Glu Asp Leu Ala Ile Tyr Tyr Cys His
        100                 105                 110

Gln Tyr Leu Ser Ser Arg Thr Phe Gly Gln Gly Thr Lys Leu Glu Ile
            115                 120                 125

Lys Arg Gly Ser Thr Ser Gly Ser Gly Lys Pro Gly Ser Gly Glu Gly
130                 135                 140

Ser Thr Lys Gly Gln Val Gln Leu Gln Gln Pro Gly Ala Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Tyr Ile His Trp Ile Lys Gln Thr Pro Gly Gln Gly
            180                 185                 190

Leu Glu Trp Val Gly Val Ile Tyr Pro Gly Asn Asp Asp Ile Ser Tyr
            195                 200                 205

Asn Gln Lys Phe Gln Gly Lys Ala Thr Leu Thr Ala Asp Lys Ser Ser
210                 215                 220

Thr Thr Ala Tyr Met Gln Leu Ser Ser Leu Thr Ser Glu Asp Ser Ala
225                 230                 235                 240

Val Tyr Tyr Cys Ala Arg Glu Val Arg Leu Arg Tyr Phe Asp Val Trp
                245                 250                 255

Gly Gln Gly Thr Thr Val Thr Val Ser Ser Ala Leu Ser Asn Ser Ile
            260                 265                 270

Met Tyr Phe Ser His Phe Val Pro Val Phe Leu Pro Ala Lys Pro Thr
            275                 280                 285

Thr Thr Pro Ala Pro Arg Pro Pro Thr Pro Ala Pro Thr Ile Ala Ser
290                 295                 300

Gln Pro Leu Ser Leu Arg Pro Glu Ala Ser Arg Pro Ala Ala Gly Gly
305                 310                 315                 320

Ala Val His Thr Arg Gly Leu Asp Ile Tyr Ile Trp Ala Pro Leu Ala
                325                 330                 335

Gly Thr Cys Gly Val Leu Leu Leu Ser Leu Val Ile Thr Lys Arg Gly
            340                 345                 350

Arg Lys Lys Leu Leu Tyr Ile Phe Lys Gln Pro Phe Met Arg Pro Val
            355                 360                 365

Gln Thr Thr Gln Glu Glu Asp Gly Cys Ser Cys Arg Phe Pro Glu Glu
            370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
            435                 440                 445

Leu Tyr Asn Glu Leu Gln Lys Asp Lys Met Ala Glu Ala Tyr Ser Glu
            450                 455                 460

Ile Gly Met Lys Gly Glu Arg Arg Arg Gly Lys Gly His Asp Gly Leu
465                 470                 475                 480
```

-continued

Tyr Gln Gly Leu Ser Thr Ala Thr Lys Asp Thr Tyr Asp Ala Leu His
                485                 490                 495

Met Gln Ala Leu Pro Pro Arg
            500

<210> SEQ ID NO 21
<211> LENGTH: 509
<212> TYPE: PRT
<213> ORGANISM: Homo sapiens

<400> SEQUENCE: 21

Met Trp Leu Gln Ser Leu Leu Leu Leu Gly Thr Val Ala Cys Ser Ile
1               5                   10                  15

Ser Glu Ile Val Leu Thr Gln Ser Pro Gly Ser Leu Ala Val Ser Pro
                20                  25                  30

Gly Glu Arg Val Thr Met Ser Cys Lys Ser Ser Gln Ser Val Phe Phe
            35                  40                  45

Ser Ser Ser Gln Lys Asn Tyr Leu Ala Trp Tyr Gln Gln Ile Pro Gly
        50                  55                  60

Gln Ser Pro Arg Leu Leu Ile Tyr Trp Ala Ser Thr Arg Glu Ser Gly
65                  70                  75                  80

Val Pro Asp Arg Phe Thr Gly Ser Gly Ser Gly Thr Asp Phe Thr Leu
                85                  90                  95

Thr Ile Ser Ser Val Gln Pro Glu Asp Leu Ala Ile Tyr Tyr Cys His
            100                 105                 110

Gln Tyr Leu Ser Ser Arg Thr Phe Gly Gln Gly Thr Lys Leu Glu Ile
        115                 120                 125

Lys Arg Gly Ser Thr Ser Gly Ser Gly Lys Pro Gly Ser Gly Glu Gly
130                 135                 140

Ser Thr Lys Gly Gln Val Gln Leu Gln Gln Pro Gly Ala Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Tyr Ile His Trp Ile Lys Gln Thr Pro Gly Gln Gly
            180                 185                 190

Leu Glu Trp Val Gly Val Ile Tyr Pro Gly Asn Asp Asp Ile Ser Tyr
        195                 200                 205

Asn Gln Lys Phe Gln Gly Lys Ala Thr Leu Thr Ala Asp Lys Ser Ser
    210                 215                 220

Thr Thr Ala Tyr Met Gln Leu Ser Ser Leu Thr Ser Glu Asp Ser Ala
225                 230                 235                 240

Val Tyr Tyr Cys Ala Arg Glu Val Arg Leu Arg Tyr Phe Asp Val Trp
                245                 250                 255

Gly Gln Gly Thr Thr Val Thr Val Ser Ala Leu Ser Asn Ser Ile Met
            260                 265                 270

Tyr Phe Ser His Phe Val Pro Val Phe Leu Pro Ala Lys Pro Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Ser Arg Pro Ala Ala Gly Gly Ala
305                 310                 315                 320

Val His Thr Arg Gly Leu Asp Lys Pro Phe Trp Val Leu Val Val Val
                325                 330                 335

Gly Gly Val Leu Ala Cys Tyr Ser Leu Leu Val Thr Val Ala Phe Ile
            340                 345                 350

```
Ile Phe Trp Val Arg Ser Lys Arg Ser Arg Leu Leu His Ser Asp Tyr
            355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 22
<211> LENGTH: 552
<212> TYPE: PRT
<213> ORGANISM: Homo sapiens

<400> SEQUENCE: 22

Met Trp Leu Gln Ser Leu Leu Leu Leu Gly Thr Val Ala Cys Ser Ile
1               5                   10                  15

Ser Glu Ile Val Leu Thr Gln Ser Pro Gly Ser Leu Ala Val Ser Pro
            20                  25                  30

Gly Glu Arg Val Thr Met Ser Cys Lys Ser Ser Gln Ser Val Phe Phe
        35                  40                  45

Ser Ser Ser Gln Lys Asn Tyr Leu Ala Trp Tyr Gln Gln Ile Pro Gly
    50                  55                  60

Gln Ser Pro Arg Leu Leu Ile Tyr Trp Ala Ser Thr Arg Glu Ser Gly
65                  70                  75                  80

Val Pro Asp Arg Phe Thr Gly Ser Gly Ser Gly Thr Asp Phe Thr Leu
                85                  90                  95

Thr Ile Ser Ser Val Gln Pro Glu Asp Leu Ala Ile Tyr Tyr Cys His
            100                 105                 110

Gln Tyr Leu Ser Ser Arg Thr Phe Gly Gln Gly Thr Lys Leu Glu Ile
        115                 120                 125

Lys Arg Gly Ser Thr Ser Gly Ser Gly Lys Pro Gly Ser Gly Glu Gly
    130                 135                 140

Ser Thr Lys Gly Gln Val Gln Leu Gln Gln Pro Gly Ala Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Tyr Ile His Trp Ile Lys Gln Thr Pro Gly Gln Gly
            180                 185                 190

Leu Glu Trp Val Gly Val Ile Tyr Pro Gly Asn Asp Asp Ile Ser Tyr
        195                 200                 205

Asn Gln Lys Phe Gln Gly Lys Ala Thr Leu Thr Ala Asp Lys Ser Ser
```

```
                    210                 215                 220
Thr Thr Ala Tyr Met Gln Leu Ser Ser Leu Thr Ser Glu Asp Ser Ala
225                 230                 235                 240

Val Tyr Tyr Cys Ala Arg Glu Val Arg Leu Arg Tyr Phe Asp Val Trp
                    245                 250                 255

Gly Gln Gly Thr Thr Val Thr Val Ser Ser Ala Leu Ser Asn Ser Ile
                260                 265                 270

Met Tyr Phe Ser His Phe Val Pro Val Phe Leu Pro Ala Lys Pro Thr
            275                 280                 285

Thr Thr Pro Ala Pro Arg Pro Pro Thr Pro Ala Pro Thr Ile Ala Ser
        290                 295                 300

Gln Pro Leu Ser Leu Arg Pro Glu Ala Ser Arg Pro Ala Ala Gly Gly
305                 310                 315                 320

Ala Val His Thr Arg Gly Leu Asp Lys Pro Phe Trp Val Leu Val Val
                325                 330                 335

Val Gly Gly Val Leu Ala Cys Tyr Ser Leu Leu Val Thr Val Ala Phe
                340                 345                 350

Ile Ile Phe Trp Val Arg Ser Lys Arg Ser Arg Leu Leu His Ser Asp
            355                 360                 365

Tyr Met Asn Met Thr Pro Arg Arg Pro Gly Pro Thr Arg Lys His Tyr
370                 375                 380

Gln Pro Tyr Ala Pro Pro Arg Asp Phe Ala Ala Tyr Arg Ser Lys Arg
385                 390                 395                 400

Gly Arg Lys Lys Leu Leu Tyr Ile Phe Lys Gln Pro Phe Met Arg Pro
                405                 410                 415

Val Gln Thr Thr Gln Glu Glu Asp Gly Cys Ser Cys Arg Phe Pro Glu
            420                 425                 430

Glu Glu Glu Gly Gly Cys Glu Leu Arg Val Lys Phe Ser Arg Ser Ala
        435                 440                 445

Asp Ala Pro Ala Tyr Gln Gln Gly Gln Asn Gln Leu Tyr Asn Glu Leu
450                 455                 460

Asn Leu Gly Arg Arg Glu Glu Tyr Asp Val Leu Asp Lys Arg Arg Gly
465                 470                 475                 480

Arg Asp Pro Glu Met Gly Gly Lys Pro Arg Arg Lys Asn Pro Gln Glu
                485                 490                 495

Gly Leu Tyr Asn Glu Leu Gln Lys Asp Lys Met Ala Glu Ala Tyr Ser
            500                 505                 510

Glu Ile Gly Met Lys Gly Glu Arg Arg Arg Gly Lys Gly His Asp Gly
        515                 520                 525

Leu Tyr Gln Gly Leu Ser Thr Ala Thr Lys Asp Thr Tyr Asp Ala Leu
530                 535                 540

His Met Gln Ala Leu Pro Pro Arg
545                 550

<210> SEQ ID NO 23
<211> LENGTH: 542
<212> TYPE: PRT
<213> ORGANISM: Homo sapiens

<400> SEQUENCE: 23

Met Trp Leu Gln Ser Leu Leu Leu Leu Gly Thr Val Ala Cys Ser Ile
1               5                   10                  15

Ser Glu Ile Val Leu Thr Gln Ser Pro Gly Ser Leu Ala Val Ser Pro
            20                  25                  30
```

-continued

Gly Glu Arg Val Thr Met Ser Cys Lys Ser Ser Gln Ser Val Phe Phe
            35                  40                  45

Ser Ser Ser Gln Lys Asn Tyr Leu Ala Trp Tyr Gln Gln Ile Pro Gly
 50                  55                  60

Gln Ser Pro Arg Leu Leu Ile Tyr Trp Ala Ser Thr Arg Glu Ser Gly
 65                  70                  75                  80

Val Pro Asp Arg Phe Thr Gly Ser Gly Ser Gly Thr Asp Phe Thr Leu
                85                  90                  95

Thr Ile Ser Ser Val Gln Pro Glu Asp Leu Ala Ile Tyr Tyr Cys His
            100                 105                 110

Gln Tyr Leu Ser Ser Arg Thr Phe Gly Gln Gly Thr Lys Leu Glu Ile
            115                 120                 125

Lys Arg Gly Ser Thr Ser Gly Ser Gly Lys Pro Gly Ser Gly Glu Gly
            130                 135                 140

Ser Thr Lys Gly Gln Val Gln Leu Gln Gln Pro Gly Ala Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Tyr Ile His Trp Ile Lys Gln Thr Pro Gly Gln Gly
            180                 185                 190

Leu Glu Trp Val Gly Val Ile Tyr Pro Gly Asn Asp Asp Ile Ser Tyr
            195                 200                 205

Asn Gln Lys Phe Gln Gly Lys Ala Thr Leu Thr Ala Asp Lys Ser Ser
            210                 215                 220

Thr Thr Ala Tyr Met Gln Leu Ser Ser Leu Thr Ser Glu Asp Ser Ala
225                 230                 235                 240

Val Tyr Tyr Cys Ala Arg Glu Val Arg Leu Arg Tyr Phe Asp Val Trp
                245                 250                 255

Gly Gln Gly Thr Thr Val Thr Val Ser Ser Ala Leu Ser Asn Ser Ile
            260                 265                 270

Met Tyr Phe Ser His Phe Val Pro Val Phe Leu Pro Ala Lys Pro Thr
            275                 280                 285

Thr Thr Pro Ala Pro Arg Pro Pro Thr Pro Ala Pro Thr Ile Ala Ser
290                 295                 300

Gln Pro Leu Ser Leu Arg Pro Glu Ala Ser Arg Pro Ala Ala Gly Gly
305                 310                 315                 320

Ala Val His Thr Arg Gly Leu Asp Phe Trp Leu Pro Ile Gly Cys Ala
                325                 330                 335

Ala Phe Val Val Val Cys Ile Leu Gly Cys Ile Leu Ile Cys Trp Leu
            340                 345                 350

Thr Lys Lys Lys Tyr Ser Ser Ser Val His Asp Pro Asn Gly Glu Tyr
            355                 360                 365

Met Phe Met Arg Ala Val Asn Thr Ala Lys Lys Ser Arg Leu Thr Asp
            370                 375                 380

Val Thr Leu Thr Lys Arg Gly Arg Lys Lys Leu Leu Tyr Ile Phe Lys
385                 390                 395                 400

Gln Pro Phe Met Arg Pro Val Gln Thr Thr Gln Glu Glu Asp Gly Cys
                405                 410                 415

Ser Cys Arg Phe Pro Glu Glu Glu Gly Gly Cys Glu Leu Arg Val
            420                 425                 430

Lys Phe Ser Arg Ser Ala Asp Ala Pro Ala Tyr Gln Gln Gly Gln Asn
            435                 440                 445

Gln Leu Tyr Asn Glu Leu Asn Leu Gly Arg Arg Glu Glu Tyr Asp Val

```
                450                 455                 460
Leu Asp Lys Arg Arg Gly Arg Asp Pro Glu Met Gly Gly Lys Pro Arg
465                 470                 475                 480

Arg Lys Asn Pro Gln Glu Gly Leu Tyr Asn Glu Leu Gln Lys Asp Lys
                485                 490                 495

Met Ala Glu Ala Tyr Ser Glu Ile Gly Met Lys Gly Glu Arg Arg Arg
                500                 505                 510

Gly Lys Gly His Asp Gly Leu Tyr Gln Gly Leu Ser Thr Ala Thr Lys
                515                 520                 525

Asp Thr Tyr Asp Ala Leu His Met Gln Ala Leu Pro Pro Arg
                530                 535                 540

<210> SEQ ID NO 24
<211> LENGTH: 459
<212> TYPE: PRT
<213> ORGANISM: Homo sapiens

<400> SEQUENCE: 24

Met Trp Leu Gln Ser Leu Leu Leu Leu Gly Thr Val Ala Cys Ser Ile
1               5                   10                  15

Ser Ile Gln Met Thr Gln Thr Ser Ser Leu Ser Ala Ser Leu Gly
                20                  25                  30

Asp Arg Val Thr Ile Ser Cys Arg Ala Ser Gln Asp Ile Ser Lys Tyr
            35                  40                  45

Leu Asn Trp Tyr Gln Gln Lys Pro Asp Gly Thr Val Lys Leu Leu Ile
50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Gly Ser Thr Ser Gly Ser
        115                 120                 125

Gly Lys Pro Gly Ser Gly Glu Gly Ser Thr Lys Gly Leu Gln Glu Ser
    130                 135                 140

Gly Pro Gly Leu Val Ala Pro Ser Gln Ser Leu Ser Val Thr Cys Thr
145                 150                 155                 160

Val Ser Gly Val Ser Leu Pro Asp Tyr Gly Val Ser Trp Ile Arg Gln
                165                 170                 175

Pro Pro Arg Lys Gly Leu Glu Trp Leu Gly Val Ile Trp Gly Ser Glu
            180                 185                 190

Thr Thr Tyr Tyr Asn Ser Ala Leu Lys Ser Arg Leu Thr Ile Ile Lys
        195                 200                 205

Asp Asn Ser Lys Ser Gln Val Phe Leu Lys Met Asn Ser Leu Gln Thr
    210                 215                 220

Asp Asp Thr Ala Ile Tyr Tyr Cys Ala Lys His Tyr Tyr Tyr Gly Gly
225                 230                 235                 240

Ser Tyr Ala Met Asp Tyr Trp Gly Gln Gly Thr Ser Val Thr Val Ser
                245                 250                 255

Ala Leu Ser Asn Ser Ile Met Tyr Phe Ser His Phe Val Pro Val Phe
            260                 265                 270

Leu Pro Ala Lys Pro Thr Thr Thr Pro Ala Pro Arg Pro Pro Thr Pro
        275                 280                 285
```

Ala Pro Thr Ile Ala Ser Gln Pro Leu Ser Leu Arg Pro Glu Ala Ser
    290                 295                 300

Arg Pro Ala Ala Gly Gly Ala Val His Thr Arg Gly Leu Asp Lys Pro
305                 310                 315                 320

Phe Trp Val Leu Val Val Val Gly Gly Val Leu Ala Cys Tyr Ser Leu
                325                 330                 335

Leu Val Thr Val Ala Phe Ile Ile Phe Trp Val Arg Val Lys Phe Ser
                340                 345                 350

Arg Ser Ala Asp Ala Pro Ala Tyr Gln Gln Gly Gln Asn Gln Leu Tyr
            355                 360                 365

Asn Glu Leu Asn Leu Gly Arg Arg Glu Glu Tyr Asp Val Leu Asp Lys
370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
            435                 440                 445

Asp Ala Leu His Met Gln Ala Leu Pro Pro Arg
450                 455

<210> SEQ ID NO 25
<211> LENGTH: 398
<212> TYPE: PRT
<213> ORGANISM: Homo sapiens

<400> SEQUENCE: 25

Met Trp Leu Gln Ser Leu Leu Leu Leu Gly Thr Val Ala Cys Ser Ile
1               5                   10                  15

Ser Glu Ile Val Leu Thr Gln Ser Pro Gly Ser Leu Ala Val Ser Pro
            20                  25                  30

Gly Glu Arg Val Thr Met Ser Cys Lys Ser Ser Gln Ser Val Phe Phe
        35                  40                  45

Ser Ser Ser Gln Lys Asn Tyr Leu Ala Trp Tyr Gln Gln Ile Pro Gly
    50                  55                  60

Gln Ser Pro Arg Leu Leu Ile Tyr Trp Ala Ser Thr Arg Glu Ser Gly
65                  70                  75                  80

Val Pro Asp Arg Phe Thr Gly Ser Gly Ser Gly Thr Asp Phe Thr Leu
                85                  90                  95

Thr Ile Ser Ser Val Gln Pro Glu Asp Leu Ala Ile Tyr Tyr Cys His
            100                 105                 110

Gln Tyr Leu Ser Ser Arg Thr Phe Gly Gln Gly Thr Lys Leu Glu Ile
        115                 120                 125

Lys Arg Gly Ser Thr Ser Gly Ser Gly Lys Pro Gly Ser Gly Glu Gly
    130                 135                 140

Ser Thr Lys Gly Gln Val Gln Leu Gln Gln Pro Gly Ala Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Tyr Ile His Trp Ile Lys Gln Thr Pro Gly Gln Gly
            180                 185                 190

Leu Glu Trp Val Gly Val Ile Tyr Pro Gly Asn Asp Asp Ile Ser Tyr
        195                 200                 205

```
Asn Gln Lys Phe Gln Gly Lys Ala Thr Leu Thr Ala Asp Lys Ser Ser
    210                 215                 220
Thr Thr Ala Tyr Met Gln Leu Ser Ser Leu Thr Ser Glu Asp Ser Ala
225                 230                 235                 240
Val Tyr Tyr Cys Ala Arg Glu Val Arg Leu Arg Tyr Phe Asp Val Trp
                245                 250                 255
Gly Gln Gly Thr Thr Val Thr Val Ser Ser Ala Leu Ser Asn Ser Ile
            260                 265                 270
Met Tyr Phe Ser His Phe Val Pro Val Phe Leu Pro Ala Lys Pro Thr
        275                 280                 285
Thr Thr Pro Ala Pro Arg Pro Pro Thr Pro Ala Pro Thr Ile Ala Ser
290                 295                 300
Gln Pro Leu Ser Leu Arg Pro Glu Ala Ser Arg Pro Ala Ala Gly Gly
305                 310                 315                 320
Ala Val His Thr Arg Gly Leu Asp Lys Pro Phe Trp Val Leu Val Val
                325                 330                 335
Val Gly Gly Val Leu Ala Cys Tyr Ser Leu Leu Val Thr Val Ala Phe
            340                 345                 350
Ile Ile Phe Trp Val Arg Ser Lys Arg Ser Arg Leu Leu His Ser Asp
        355                 360                 365
Tyr Met Asn Met Thr Pro Arg Arg Pro Gly Pro Thr Arg Lys His Tyr
370                 375                 380
Gln Pro Tyr Ala Pro Pro Arg Asp Phe Ala Ala Tyr Arg Ser
385                 390                 395

<210> SEQ ID NO 26
<211> LENGTH: 500
<212> TYPE: PRT
<213> ORGANISM: Homo sapiens

<400> SEQUENCE: 26

Met Trp Leu Gln Ser Leu Leu Leu Leu Gly Thr Val Ala Cys Ser Ile
1               5                   10                  15
Ser Ile Gln Met Thr Gln Thr Thr Ser Ser Leu Ser Ala Ser Leu Gly
            20                  25                  30
Asp Arg Val Thr Ile Ser Cys Arg Ala Ser Gln Asp Ile Ser Lys Tyr
        35                  40                  45
Leu Asn Trp Tyr Gln Gln Lys Pro Asp Gly Thr Val Lys Leu Leu Ile
    50                  55                  60
Tyr His Thr Ser Arg Leu His Ser Gly Val Pro Ser Arg Phe Ser Gly
65                  70                  75                  80
Ser Gly Ser Gly Thr Asp Tyr Ser Leu Thr Ile Ser Asn Leu Glu Gln
                85                  90                  95
Glu Asp Ile Ala Thr Tyr Phe Cys Gln Gln Gly Asn Thr Leu Pro Tyr
            100                 105                 110
Thr Phe Gly Gly Gly Thr Lys Leu Glu Ile Gly Ser Thr Ser Gly Ser
        115                 120                 125
Gly Lys Pro Gly Ser Gly Glu Gly Ser Thr Lys Gly Leu Gln Glu Ser
    130                 135                 140
Gly Pro Gly Leu Val Ala Pro Ser Gln Ser Leu Ser Val Thr Cys Thr
145                 150                 155                 160
Val Ser Gly Val Ser Leu Pro Asp Tyr Gly Val Ser Trp Ile Arg Gln
                165                 170                 175
Pro Pro Arg Lys Gly Leu Glu Trp Leu Gly Val Ile Trp Gly Ser Glu
```

```
                    180                 185                 190
Thr Thr Tyr Tyr Asn Ser Ala Leu Lys Ser Arg Leu Thr Ile Ile Lys
                195                 200                 205

Asp Asn Ser Lys Ser Gln Val Phe Leu Lys Met Asn Ser Leu Gln Thr
        210                 215                 220

Asp Asp Thr Ala Ile Tyr Tyr Cys Ala Lys His Tyr Tyr Tyr Gly Gly
225                 230                 235                 240

Ser Tyr Ala Met Asp Tyr Trp Gly Gln Gly Thr Ser Val Thr Val Ser
                245                 250                 255

Ala Leu Ser Asn Ser Ile Met Tyr Phe Ser His Phe Val Pro Val Phe
        260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Ser
        290                 295                 300

Arg Pro Ala Ala Gly Gly Ala Val His Thr Arg Gly Leu Asp Lys Pro
305                 310                 315                 320

Phe Trp Val Leu Val Val Val Gly Gly Val Leu Ala Cys Tyr Ser Leu
                325                 330                 335

Leu Val Thr Val Ala Phe Ile Ile Phe Trp Val Arg Ser Lys Arg Ser
                340                 345                 350

Arg Leu Leu His Ser Asp Tyr Met Asn Met Thr Pro Arg Arg Pro Gly
            355                 360                 365

Pro Thr Arg Lys His Tyr Gln Pro Tyr Ala Pro Pro Arg Asp Phe Ala
        370                 375                 380

Ala Tyr Arg Ser Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg
            500

<210> SEQ ID NO 27
<211> LENGTH: 484
<212> TYPE: PRT
<213> ORGANISM: Homo sapiens

<400> SEQUENCE: 27

Met Trp Leu Gln Ser Leu Leu Leu Leu Gly Thr Val Ala Cys Ser Ile
1               5                   10                  15

Ser Glu Ile Val Leu Thr Gln Ser Pro Gly Ser Leu Ala Val Ser Pro
            20                  25                  30

Gly Glu Arg Val Thr Met Ser Cys Lys Ser Ser Gln Ser Val Phe Phe
        35                  40                  45
```

```
Ser Ser Ser Gln Lys Asn Tyr Leu Ala Trp Tyr Gln Gln Ile Pro Gly
 50                  55                  60

Gln Ser Pro Arg Leu Leu Ile Tyr Trp Ala Ser Thr Arg Glu Ser Gly
 65                  70                  75                  80

Val Pro Asp Arg Phe Thr Gly Ser Gly Ser Gly Thr Asp Phe Thr Leu
                     85                  90                  95

Thr Ile Ser Ser Val Gln Pro Glu Asp Leu Ala Ile Tyr Tyr Cys His
                100                 105                 110

Gln Tyr Leu Ser Ser Arg Thr Phe Gly Gln Gly Thr Lys Leu Glu Ile
                115                 120                 125

Lys Arg Gly Ser Thr Ser Gly Ser Gly Lys Pro Gly Ser Gly Glu Gly
130                 135                 140

Ser Thr Lys Gly Gln Val Gln Leu Gln Gln Pro Gly Ala Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Tyr Ile His Trp Ile Lys Gln Thr Pro Gly Gln Gly
                180                 185                 190

Leu Glu Trp Val Gly Val Ile Tyr Pro Gly Asn Asp Asp Ile Ser Tyr
                195                 200                 205

Asn Gln Lys Phe Gln Gly Lys Ala Thr Leu Thr Ala Asp Lys Ser Ser
                210                 215                 220

Thr Thr Ala Tyr Met Gln Leu Ser Ser Leu Thr Ser Glu Asp Ser Ala
225                 230                 235                 240

Val Tyr Tyr Cys Ala Arg Glu Val Arg Leu Arg Tyr Phe Asp Val Trp
                245                 250                 255

Gly Gln Gly Thr Thr Val Thr Val Ser Ser Ile Glu Val Met Tyr Pro
                260                 265                 270

Pro Pro Tyr Leu Asp Asn Glu Lys Ser Asn Gly Thr Ile Ile His Val
                275                 280                 285

Lys Gly Lys His Leu Cys Pro Ser Pro Leu Phe Pro Gly Pro Ser Lys
                290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
                340                 345                 350

Gly Pro Thr Arg Lys His Tyr Gln Pro Tyr Ala Pro Pro Arg Asp Phe
                355                 360                 365

Ala Ala Tyr Arg Ser Arg Val Lys Phe Ser Arg Ser Ala Asp Ala Pro
                370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Gly Glu Arg Arg Arg Gly Lys Gly His Asp Gly Leu Tyr Gln Gly
450                 455                 460

Leu Ser Thr Ala Thr Lys Asp Thr Tyr Asp Ala Leu His Met Gln Ala
```

465        470        475        480

Leu Pro Pro Arg

<210> SEQ ID NO 28
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 28
tggccgggtt ctagagtgcc agg                                               23

<210> SEQ ID NO 29
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 29
ggccgggttc tagagtgcca ggg                                               23

<210> SEQ ID NO 30
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 30
caccgaggag tgagtagtcc tgg                                               23

<210> SEQ ID NO 31
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 31
tccagcgaac ttcacctgac agg                                               23

<210> SEQ ID NO 32
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 32
ccaagtatcc ccggactctt tgg                                               23

<210> SEQ ID NO 33
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 33
agcattatcc aaagagtccg ggg                                               23

<210> SEQ ID NO 34
<211> LENGTH: 23

```
<212> TYPE: DNA
<213> ORGANISM: Artificial Sequence
<220> FEATURE:
<223> OTHER INFORMATION: Synthetic Polynucleotide

<400> SEQUENCE: 34
acttgggtgg aagtattgtc tgg                                              23

<210> SEQ ID NO 35
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 35
gtctgcgagt ctgcgtgcgt ggg                                              23

<210> SEQ ID NO 36
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 36
cgtctgcgag tctgcgtgcg tgg                                              23

<210> SEQ ID NO 37
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 37
gcgagtctgc gtgcgtggga agg                                              23

<210> SEQ ID NO 38
<211> LENGTH: 1568
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 38
ggtgtcgtga gcggccgctg aactggccac catgtggctg cagtctctgc tgctgctggg     60
caccgtggcc tgtagcatca gcgagatcgt gctgacccag agccctggct ctctggctgt    120
gtctcctggc gagcgcgtga ccatgagctg caagagcagc cagagcgtgt tcttcagcag    180
ctcccagaag aactacctgg cctggtatca gcagatcccc ggccagagcc ccagactgct    240
gatctactgg gccagcacca gagaaagcgg cgtgcccgat agattcaccg gcagcggctc    300
tggcaccgac ttcaccctga caatcagcag cgtgcagccc gaggacctgg ccatctacta    360
ctgccaccag tacctgagca gccggacctt tggccagggc accaagctgg aaatcaagcg    420
gggcagcaca agcggcagcg gaaagcctgg atctggcgag ggctctacca agggccaggt    480
gcagctgcag cagcctggcg ccgaagtcgt gaaacctggc gcctccgtga agatgtcctg    540
caaggccagc ggctacacct tcaccagcta ctacatccac tggatcaagc agacccctgg    600
acagggcctg gaatgggtgg gagtgatcta ccccggcaac gacgacatca gctacaacca    660
```

```
gaagttccag ggcaaggcca ccctgaccgc cgacaagtct agcaccaccg cctacatgca    720
gctgtccagc ctgaccagcg aggacagcgc cgtgtactac tgcgccagag aagtgcggct    780
gcggtacttc gatgtgtggg gccagggaac caccgtgacc gtgtctagcg ccctgagcaa    840
cagcatcatg tacttcagcc acttcgtgcc cgtgtttctg cccgccaagc ctaccacaac    900
ccctgcccct agacctccta ccccagcccc tacaatcgcc agccagcctc tgtctctgag    960
gcccgaggct tctagaccag ctgctggcgg agccgtgcac accagaggcc tggatatcta   1020
catctgggcc ccactggccg gcacctgtgg cgtgctgctg ctgtctctcg tgatcaccaa   1080
gagaggccgg aagaagctgc tgtacatctt caagcagccc ttcatgcggc ccgtgcagac   1140
cacccaggaa gaggacggct gtagctgccg gttccccgag gaagaagaag ggggctgcga   1200
gctgagagtg aagttcagca gaagcgccga cgcccctgcc tatcagcagg gccagaacca   1260
gctgtacaac gagctgaacc tgggcagacg ggaagagtac gacgtgctgg acaagcggag   1320
aggcagggac cctgagatgg gcggcaagcc cagacggaag aaccctcagg aaggcctgta   1380
taacgaactg cagaaagaca agatggccga ggcctactcc gagatcggaa tgaagggcga   1440
gcggagaaga ggcaagggcc acgatggact gtaccagggc ctgagcaccg ccaccaagga   1500
cacctatgac gccctgcaca tgcaggccct gccccccaga tgaaattcat cgacgttaac   1560
tattctag                                                            1568
```

<210> SEQ ID NO 39
<211> LENGTH: 1586
<212> TYPE: DNA
<213> ORGANISM: Homo sapiens
<220> FEATURE:
<221> NAME/KEY: misc_feature
<222> LOCATION: (20)..(20)
<223> OTHER INFORMATION: n is a, c, g, or t

<400> SEQUENCE: 39

```
ggtgtcgtga gcggccgctg aactggccac catgtggctg cagtctctgc tgctgctggg     60
caccgtggcc tgtagcatca gcgagatcgt gctgacccag agccctggct ctctggctgt    120
gtctcctggc gagcgcgtga ccatgagctg caagagcagc cagagcgtgt tcttcagcag    180
ctcccagaag aactacctgg cctggtatca gcagatcccc ggccagagcc ccagactgct    240
gatctactgg gccagcacca gagaaagcgg cgtgcccgat agattcaccg gcagcggctc    300
tggcaccgac ttcaccctga caatcagcag cgtgcagccc gaggacctgg ccatctacta    360
ctgccaccag tacctgagca gccggacctt tggccagggc accaagctgg aaatcaagcg    420
gggcagcaca agcggcagcg gaaagcctgg atctggcgag ggctctacca agggccaggt    480
gcagctgcag cagcctggcg ccgaagtcgt gaaacctggc gcctccgtga agatgtcctg    540
caaggccagc ggctacacct tcaccagcta ctacatccac tggatcaagc agacccctgg    600
acagggcctg gaatgggtgg gagtgatcta ccccggcaac gacgacatca gctacaacca    660
gaagttccag ggcaaggcca ccctgaccgc cgacaagtct agcaccaccg cctacatgca    720
gctgtccagc ctgaccagcg aggacagcgc cgtgtactac tgcgccagag aagtgcggct    780
gcggtacttc gatgtgtggg gccagggaac caccgtgacc gtgtctgccc tgagcaacag    840
catcatgtac ttcagccact tcgtgcccgt gtttctgccc gccaagccta ccacaacccc    900
tgcccctaga cctcctaccc cagcccctac aatcgccagc cagcctctgt ctctgaggcc    960
cgaggcttct agaccagctg ctggcggagc cgtgcacacc agaggactgg acaagccctt   1020
ctgggtgctg gtggtcgtgg gcggagtgct ggcctgttac agcctgctcg tgacagtggc   1080
```

| | |
|---|---|
| cttcatcatc tttttgggtgc gcagcaagcg gtctagactg ctgcacacgcg actacatgaa | 1140 |
| catgacccccc agaaggccag gccccacccg gaagcactat cagccttacg ccccctcccag | 1200 |
| agacttcgcc gcctaccggt ccagagtgaa gttcagcaga agcgccgacg cccctgccta | 1260 |
| tcagcagggc cagaaccagc tgtacaacga gctgaacctg gcagacggga agagtacga | 1320 |
| cgtgctggac aagagaagag gccgggaccc tgagatgggc ggcaagccca gacggaagaa | 1380 |
| ccctcaggaa ggcctgtata cgaactgca gaaagacaag atggccgagg cctactccga | 1440 |
| gatcggcatg aagggcgaac ggcggagagg caagggacac gatggactgt accagggcct | 1500 |
| gagcaccgcc accaaggaca cctatgacgc cctgcacatg caggccctgc cccccagatg | 1560 |
| aaattcatcg acgttaacta ttctag | 1586 |

<210> SEQ ID NO 40
<211> LENGTH: 1715
<212> TYPE: DNA
<213> ORGANISM: Homo sapiens

<400> SEQUENCE: 40

| | |
|---|---|
| ggtgtcgtga gcggccgctg aactggccac catgtggctg cagtctctgc tgctgctggg | 60 |
| caccgtggcc tgtagcatca gcgagatcgt gctgacccag agccctggct ctctggctgt | 120 |
| gtctcctggc gagcgcgtga ccatgagctg caagagcagc cagagcgtgt tcttcagcag | 180 |
| ctcccagaag aactacctgg cctggtatca gcagatcccc ggccagagcc ccagactgct | 240 |
| gatctactgg gccagcacca gagaaagcgg cgtgcccgat agattcaccg gcagcggctc | 300 |
| tggcaccgac ttcaccctga caatcagcag cgtgcagccc gaggacctgg ccatctacta | 360 |
| ctgccaccag tacctgagca gccggacctt tggccagggc accaagctgg aaatcaagcg | 420 |
| gggcagcaca agcggcagcg gaaagcctgg atctggcgag ggctctacca agggccaggt | 480 |
| gcagctgcag cagcctggcg ccgaagtcgt gaaacctggc gcctccgtga agatgtcctg | 540 |
| caaggccagc ggctacacct tcaccagcta ctacatccac tggatcaagc agacccctgg | 600 |
| acagggcctg gaatgggtgg gagtgatcta ccccggcaac gacgacatca gctacaacca | 660 |
| gaagttccag ggcaaggcca ccctgaccgc cgacaagtct agcaccaccg cctacatgca | 720 |
| gctgtccagc ctgaccagcg aggacagcgc cgtgtactac tgcgccagag aagtgcggct | 780 |
| gcggtacttc gatgtgtggg gccagggaac caccgtgacc gtgtctagcg ccctgagcaa | 840 |
| cagcatcatg tacttcagcc acttcgtgcc cgtgtttctg cccgccaagc ctaccacaac | 900 |
| ccctgcccct agacctccta cccccagccc tacaatcgcc agccagcctc tgtctctgag | 960 |
| gcccgaggct tctagaccag ctgctggcgg agccgtgcac accagaggac tggacaagcc | 1020 |
| cttctgggtg ctggtggtcg tgggcggagt gctggcctgt acagcctgc tcgtgacagt | 1080 |
| ggccttcatc atctttttggg tgcgcagcaa gcggtctaga ctgctgcaca cgcgactacat | 1140 |
| gaacatgacc cccagaaggc caggccccac ccggaagcac tatcagcctt acgcccctcc | 1200 |
| cagagacttc gccgcctaca gatccaagag aggccggaag aagctgctgt acatcttcaa | 1260 |
| gcagcccttc atgcggcccg tgcagaccac ccaggaagag gacggctgta gctgccggtt | 1320 |
| cccccgaggaa gaagaagggg gctgcgagct gagagtgaag ttcagcagaa gcgccgacgc | 1380 |
| ccctgcctat cagcagggcc agaaccagct gtacaacgag ctgaacctgg cagacggga | 1440 |
| agagtacgac gtgctggaca agagaagagg ccgggaccct gagatgggcg gcaagcccag | 1500 |
| acggaagaac cctcaggaag gcctgtataa cgaactgcag aaagacaaga tggccgaggc | 1560 |

```
ctactccgag atcggaatga agggcgagcg gcggagaggc aagggacacg atggactgta    1620
ccagggcctg agcaccgcca ccaaggacac ctatgacgcc ctgcacatgc aggccctgcc    1680
ccccagatga aattcatcga cgttaactat tctag                              1715

<210> SEQ ID NO 41
<211> LENGTH: 1436
<212> TYPE: DNA
<213> ORGANISM: Homo sapiens

<400> SEQUENCE: 41
ggtgtcgtga gcggccgctg aactggccac catgtggctg cagtctctgc tgctgctggg      60
caccgtggcc tgcagcatca gcatccagat gacccagacc accagcagcc tgagcgccag     120
cctgggcgat agagtgacca tcagctgcag agccagccag gacatcagca agtacctgaa     180
ctggtatcag cagaaacccg acggcaccgt gaagctgctg atctaccaca ccagcagact     240
gcacagcggc gtgcccctct agattttccgg cagcggctcc ggcaccgact acagcctgac     300
```
```
catctccaac ctgaacagg aagatatcgc tacctacttc tgtcagcaag caacaccct       360 gccctacacc ttcggcggag gcaccaagct ggaaatcggc agcacaagcg gctctggcaa     420
gcctggatct ggcgagggct ctaccaaggg cctgcaggaa tctggccctg gactggtggc     480
ccctagccag agcctgtctg tgacctgtac cgtgtccggc gtgtccctgc ctgactatgg     540
cgtgtcctgg atcagacagc ccccagaaa gggcctggaa tggctgggag tgatctgggg     600
cagcgagaca acctactaca acagcgccct gaagtcccgg ctgaccatca tcaaggacaa     660
ctccaagagc caggtgttcc tgaagatgaa cagcctgcag accgacgaca ccgccatcta     720
ctactgcgcc aagcactact actacggcgg cagctacgcc atggactact ggggccaggg     780
cacaagcgtg accgtgtctg ccctgagcaa cagcatcatg tacttcagcc acttcgtgcc     840
cgtgtttctg cccgccaagc ctaccacaac ccctgcccct agacctccta ccccagcccc     900
tacaatcgcc agccagcctc tgtctctgag gcccgaggct tctagaccag ctgctggcgg     960
agccgtgcac accagaggac tggacaagcc cttctgggtg ctggtggtcg tgggcggagt    1020
gctggcctgt tatagcctgc tcgtgacagt ggccttcatc atcttttggg tgcgcgtgaa    1080
gttcagccgc agcgccgatg cccctgccta tcagcaggga cagaaccagc tgtacaacga    1140
gctgaacctg ggcagacggg aagagtacga cgtgctggac aagagaagag ccgggaccc    1200
```
(line 1200)
```
tgagatgggc ggcaagccca agaaagaa ccccaggaa ggcctgtata cgaactgca       1260 gaaagacaag atggccgagg cctacagcga gatcggcatg aagggcgaac ggcggagagg    1320
caagggccac gatggactgt atcagggcct gagcaccgcc accaaggaca cctatgacgc    1380
cctgcacatg caggctctgc cccctcgctg aaattcatcg acgttaacta ttctag        1436

<210> SEQ ID NO 42
<211> LENGTH: 1253
<212> TYPE: DNA
<213> ORGANISM: Homo sapiens

<400> SEQUENCE: 42
ggtgtcgtga gcggccgctg aactggccac catgtggctg cagtctctgc tgctgctggg      60
caccgtggcc tgtagcatca gcgagatcgt gctgacccag agccctggct ctctggctgt     120
gtctcctggc gagcgcgtga ccatgagctg caagagcagc cagagcgtgt tcttcagcag     180
ctcccagaag aactacctgg cctggtatca gcagatcccc ggccagagcc ccagactgct     240
gatctactgg gccagcacca gagaaagcgg cgtgcccgat agattcaccg gcagcggctc     300
```

```
tggcaccgac ttcaccctga caatcagcag cgtgcagccc gaggacctgg ccatctacta    360
ctgccaccag tacctgagca gccggacctt tggccagggc accaagctgg aaatcaagcg    420
gggcagcaca agcggcagcg aaagcctgga tctggcgag ggctctacca agggccaggt    480
gcagctgcag cagcctggcg ccgaagtcgt gaaacctggc cctccgtga agatgtcctg    540 caaggccagc ggctacacct tcaccagcta ctacatccac tggatcaagc agaccctgg    600 acagggcctg aatgggtgg gagtgatcta ccccggcaac gacgcatca gctacaacca    660 gaagttccag ggcaaggcca ccctgaccgc cgacaagtct agcaccaccg cctacatgca    720
gctgtccagc ctgaccagcg aggacagcgc cgtgtactac tgcgccagag aagtgcggct    780
gcggtacttc gatgtgtggg gccagggaac caccgtgacc gtgtctagcg ccctgagcaa    840
cagcatcatg tacttcagcc acttcgtgcc cgtgtttctg cccgccaagc ctaccacaac    900
ccctgcccct agacctccta ccccagcccc tacaatcgcc agccagcctc tgtctctgag    960
gcccgaggct tctagaccag ctgctggcgg agccgtgcac accagaggac tggacaagcc   1020
cttctgggtg ctggtggtcg tgggcggagt gctggcctgt tacagcctgc tcgtgacagt   1080
ggccttcatc atcttttggg tgcgcagcaa gcggtctaga ctgctgcaca gcgactacat   1140
gaacatgacc cccagaaggc caggccccac ccggaagcac tatcagcctt acgcccctcc   1200
cagagacttc gccgcctaca aagctgaaa ttcatcgacg ttaactattc tag           1253

<210> SEQ ID NO 43
<211> LENGTH: 1559
<212> TYPE: DNA
<213> ORGANISM: Homo sapiens

<400> SEQUENCE: 43
ggtgtcgtga gcggccgctg aactggccac catgtggctg cagtctctgc tgctgctggg     60
caccgtggcc tgcagcatca gcatccagat gacccagacc accagcagcc tgagcgccag    120
cctgggcgat agagtgacca tcagctgcag agccagccag gacatcagca gtacctgaa    180 ctggtatcag cagaaacccg acggcaccgt gaagctgctg atctaccaca ccagcagact    240
gcacagcggc gtgccctcta gattttccgg cagcggctcc ggcaccgact acagcctgac    300
catctccaac ctggaacagg aagatatcgc tacctacttc tgtcagcaag gcaacaccct    360
gccctacacc ttcggcggag gcaccaagct ggaaatcggc agcacaagcg gctctggcaa    420
gcctggatct ggcgagggct ctaccaaggg cctgcaggaa tctggccctg actggtggc    480 ccctagccag agcctgtctg tgacctgtac cgtgtccggc gtgtccctgc ctgactatgg    540
cgtgtcctgg atcagacagc cccccagaaa gggcctggaa tggctgggag tgatctgggg    600
cagcgagaca acctactaca acagcgccct gaagtcccgg ctgaccatca tcaaggacaa    660
ctccaagagc caggtgttcc tgaagatgaa cagcctgcag accgacgaca ccgccatcta    720
ctactgcgcc aagcactact actacggcgg cagctacgcc atggactact ggggccaggg    780
cacaagcgtg accgtgtctg ccctgagcaa cagcatcatg tacttcagcc acttcgtgcc    840
cgtgtttctg cccgccaagc ctaccacaac ccctgcccct agacctccta ccccagcccc    900
tacaatcgcc agccagcctc tgtctctgag gcccgaggct tctagaccag ctgctggcgg    960
agccgtgcac accagaggac tggacaagcc cttctgggtg ctggtggtcg tgggcggagt   1020
gctggcctgt tatagcctgc tcgtgacagt ggccttcatc atcttttggg tgcgcagcaa   1080
gcggagccgg ctgctgcact ccgactacat gaacatgacc cccagacggc caggccccac   1140
```

```
ccggaaacac tatcagcctt acgcccctcc cagagacttc gccgcctacc ggtccagagt   1200
gaagttcagc agatccgccg acgcccctgc ctatcagcag ggacagaacc agctgtacaa   1260
cgagctgaac ctgggcagac gggaagagta cgacgtgctg acaagagaa gaggccggga    1320 ccctgagatg gcggcaagc ccagaagaaa gaacccccag gaaggcctgt ataacgaact    1380
gcagaaagac aagatggccg aggcctacag cgagatcggc atgaagggcg aacggcggag   1440
aggcaagggc cacgatggac tgtatcaggg cctgagcacc gccaccaagg acacctatga   1500
cgccctgcac atgcaggctc tgccccctcg ctgaaattca tcgacgttaa ctattctag    1559
```

<210> SEQ ID NO 44
<211> LENGTH: 1514
<212> TYPE: DNA
<213> ORGANISM: Homo sapiens

<400> SEQUENCE: 44

```
ggtgtcgtga gcggccgctg aactggccac catgtggctg cagtctctgc tgctgctggg     60
caccgtggcc tgtagcatca gcgagatcgt gctgacccag agccctggct ctctggctgt    120
gtctcctggc gagcgcgtga ccatgagctg caagagcagc cagagcgtgt tcttcagcag    180
ctcccagaag aactacctgg cctggtatca gcagatcccc ggccagagcc ccagactgct    240
gatctactgg gccagcacca gagaaagcgg cgtgcccgat agattcaccg gcagcggctc    300
tggcaccgac ttcaccctga caatcagcag cgtgcagccc gaggacctgg ccatctacta    360
ctgccaccag tacctgagca gccggaccct tggccagggc accaagctgg aaatcaagcg    420
gggcagcaca gcggcagcg aaagcctgg atctggcgag gctctacca agggccaggt     480 gcagctgcag cagcctggcg ccgaagtcgt gaaacctggc gcctccgtga agatgtcctg    540
caaggccagc ggctacacct tcaccagcta ctacatccac tggatcaagc agacccctgg    600
acagggcctg gaatgggtgg gagtgatcta ccccggcaac gacgacatca gctacaacca    660
gaagttccag ggcaaggcca ccctgaccgc cgacaagtct agcaccaccg cctacatgca    720
gctgtccagc ctgaccagcg aggacagcgc cgtgtactac tgcgccagag aagtgcggct    780
gcggtacttc gatgtgtggg gccagggaac caccgtgacc gtgtcagca tcgaagtgat     840 gtaccccccct ccctacctgg acaacgagaa gtccaacggc accatcatcc acgtgaaggg    900
caagcacctg tgccccagcc ctctgtttcc tggccctagc aagcccttct gggtgctggt    960
ggtcgtgggc ggagtgctgg cctgttacag cctgctcgtg acagtggcct tcatcatctt   1020
ttgggtgcgc agcaagcggt ctagactgct gcacagcgac tacatgaaca tgaccccag   1080 aaggccaggc cccacccgga agcactatca gccttacgcc cctcccagag acttcgccgc   1140
ctaccggtcc agagtgaagt tcagcagaag cgccgacgcc cctgcctatc agcagggcca   1200
gaaccagctg tacaacgagc tgaacctggg cagacgggaa gagtacgacg tgctggacaa   1260
gcggagaggc agggaccctg agatgggcgg caagcccaga cggaagaacc ctcaggaagg   1320
cctgtataac gaactgcaga agacaagat ggccgaggcc tactccgaga tcggcatgaa    1380
gggcgagcgg agaagaggca agggccacga tggactgtac cagggcctga gcaccgccac   1440
caaggacacc tatgacgccc tgcacatgca ggccctgccc cccagatgaa attcatcgac   1500
gttaactatt ctag                                                     1514
```

<210> SEQ ID NO 45
<211> LENGTH: 21
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: n is a, c, g, or t

<400> SEQUENCE: 45
atcgatcgat cgtacgcgng g                                              21

<210> SEQ ID NO 46
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: n is a, c, g, or t

<400> SEQUENCE: 46
atgcatcgta catcgatcgn gg                                             22

<210> SEQ ID NO 47
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 47

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
            35
```